(12) United States Patent
Connor

(10) Patent No.: US 12,346,156 B2
(45) Date of Patent: Jul. 1, 2025

(54) WRIST-WORN DEVICE WITH A VARIABLE-SIZE DISPLAY WHICH IS EXPANDED BY UNROLLING OR SLIDING

(71) Applicant: Robert A. Connor, St. Paul, MN (US)

(72) Inventor: Robert A. Connor, St. Paul, MN (US)

(73) Assignee: Medibotics LLC, Ham Lake, MN (US)

( * ) Notice: Subject to any disclaimer, the term of this patent is extended or adjusted under 35 U.S.C. 154(b) by 36 days.

(21) Appl. No.: 18/226,213

(22) Filed: Jul. 25, 2023

(65) Prior Publication Data

US 2023/0384825 A1     Nov. 30, 2023

Related U.S. Application Data

(63) Continuation-in-part of application No. 17/871,952, filed on Jul. 24, 2022, now Pat. No. 11,747,769, which is a continuation-in-part of application No. 17/515,509, filed on Oct. 31, 2021, now abandoned, which is a continuation-in-part of application No. 16/926,748, filed on Jul. 12, 2020, now abandoned, said application No. 17/871,952 is a continuation-in-part of application No. 16/926,748, filed on Jul. 12, 2020, now abandoned, and a continuation-in-part of application No. 16/819,147, filed on Mar. 15, 2020, now Pat. No. 11,429,151, which is a continuation-in-part of application No. 16/598,514, filed on Oct. 10, 2019, now abandoned, said application No. 16/926,748 is a continuation-in-part of application No. 15/431,769, filed on Feb. 14, 2017, now abandoned, said application No. 16/598,514 is a continuation-in-part of application No. 15/294,746, filed on Oct. 16, 2016, now Pat. No. 10,627,861, said application No. 16/819,147 is a continuation-in-part of application (Continued)

(51) Int. Cl.
   *G06F 1/16*     (2006.01)
   *G06F 3/01*     (2006.01)
   *G06F 3/041*     (2006.01)

(52) U.S. Cl.
CPC ............ *G06F 1/163* (2013.01); *G06F 1/1624* (2013.01); *G06F 1/1652* (2013.01); *G06F 3/041* (2013.01); *G06F 3/017* (2013.01)

(58) Field of Classification Search
CPC ...... G04G 17/083; G04G 17/08; G04G 21/02; G04G 21/00; G06F 1/1652; G06F 3/041; G06F 1/3265; G06F 1/163; G06F 1/1641; G06F 1/1647; G06F 1/1624; G06F 3/017; A61B 5/681; A61B 5/7445
See application file for complete search history.

(56) References Cited

U.S. PATENT DOCUMENTS 6,035,035 A     3/2000   Firooz
6,970,157 B2   11/2005   Siddeeq
(Continued)

*Primary Examiner* — Yaron Cohen

(57) ABSTRACT

This invention is a device with an expandable light-emitting display which is worn on a persons' wrist and/or lower arm. The expandable display can be a flexible display which can be rolled and then expanded by unrolling it out from a housing. In an example, the flexibility of the expandable second display can be adjusted. The second display can be made flexible so that is can be rolled around a roller, but can also be made rigid for use as a touch screen in an expanded state.

2 Claims, 25 Drawing Sheets

Related U.S. Application Data

No. 15/294,746, filed on Oct. 16, 2016, now Pat. No. 10,627,861, said application No. 16/598,514 is a continuation-in-part of application No. 14/623,337, filed on Feb. 16, 2015, now Pat. No. 9,582,035, said application No. 15/294,746 is a continuation-in-part of application No. 14/623,337, filed on Feb. 16, 2015, now Pat. No. 9,582,035, said application No. 15/431,769 is a continuation-in-part of application No. 14/623,337, filed on Feb. 16, 2015, now Pat. No. 9,582,035.

(60) Provisional application No. 62/882,560, filed on Aug. 4, 2019, provisional application No. 62/876,213, filed on Jul. 19, 2019, provisional application No. 62/820,337, filed on Mar. 19, 2019, provisional application No. 62/115,691, filed on Feb. 13, 2015, provisional application No. 62/113,423, filed on Feb. 7, 2015, provisional application No. 62/111,163, filed on Feb. 3, 2015, provisional application No. 62/106,856, filed on Jan. 23, 2015, provisional application No. 62/100,217, filed on Jan. 6, 2015, provisional application No. 61/948,124, filed on Mar. 5, 2014, provisional application No. 61/944,090, filed on Feb. 25, 2014.

(56) References Cited

U.S. PATENT DOCUMENTS

| | | |
|---|---|---|
| 7,558,057 B1 * | 7/2009 | Naksen .................. G06F 1/1613 361/679.56 |
| 8,851,372 B2 | 10/2014 | Zhou et al. |
| 9,848,494 B2 | 12/2017 | Huitema et al. |
| 9,877,384 B2 | 1/2018 | Lee et al. |
| 10,152,028 B2 | 12/2018 | Kim |
| 10,216,227 B2 | 2/2019 | Jin et al. |
| 10,299,391 B2 | 5/2019 | Kim et al. |
| 10,319,263 B2 | 6/2019 | Lee et al. |
| 10,319,331 B2 | 6/2019 | Pasupathi |
| 10,517,180 B2 | 12/2019 | Choi et al. |
| 10,617,017 B2 | 4/2020 | Park et al. |
| 10,755,668 B2 | 8/2020 | Pasupathi |
| 10,802,544 B2 | 10/2020 | Kwak et al. |
| 10,820,433 B2 | 10/2020 | Cha |
| 10,827,630 B2 | 11/2020 | Kim et al. |
| 10,877,525 B2 | 12/2020 | Kang et al. |
| 10,937,393 B2 | 3/2021 | Lee et al. |
| 10,969,830 B2 | 4/2021 | In et al. |
| 11,016,532 B2 | 5/2021 | Yang |
| 11,527,179 B2 | 12/2022 | Han et al. |
| 11,576,270 B2 | 2/2023 | Rha et al. |
| 11,592,874 B1 | 2/2023 | Seger et al. |
| 11,614,777 B2 | 3/2023 | Kishimoto et al. |
| 11,647,598 B2 | 5/2023 | Zhang et al. |
| 11,699,372 B2 | 7/2023 | Lee et al. |
| 2002/0021622 A1 | 2/2002 | Baroche |
| 2009/0219788 A1 | 9/2009 | Henley |
| 2011/0187681 A1 | 8/2011 | Kim et al. |
| 2013/0044215 A1 | 2/2013 | Rothkopf |
| 2014/0239065 A1 * | 8/2014 | Zhou .................. G06F 1/1677 235/380 |
| 2015/0029227 A1 | 1/2015 | Park et al. |
| 2015/0113473 A1 | 4/2015 | Otsuka et al. |
| 2015/0338882 A1 | 11/2015 | Yun et al. |
| 2016/0239190 A1 | 8/2016 | Forutanpour et al. |
| 2016/0240154 A1 | 8/2016 | Forutanpour et al. |
| 2016/0246558 A1 | 8/2016 | Prushinskiy et al. |
| 2016/0267310 A1 | 9/2016 | Al Nasser et al. |
| 2018/0032106 A1 | 2/2018 | Yu et al. |
| 2018/0120901 A1 | 5/2018 | Jin et al. |
| 2018/0137801 A1 | 5/2018 | An |
| 2019/0196550 A1 | 6/2019 | Kim et al. |
| 2019/0229288 A1 | 7/2019 | Ahn et al. |
| 2019/0237532 A1 | 8/2019 | Ahn et al. |
| 2019/0268455 A1 | 8/2019 | Baek et al. |
| 2019/0268771 A1 | 8/2019 | Seo et al. |
| 2019/0278336 A1 | 9/2019 | Choi et al. |
| 2019/0296259 A1 | 9/2019 | Baek et al. |
| 2019/0305237 A1 | 10/2019 | Shin et al. |
| 2020/0042037 A1 | 2/2020 | Sun |
| 2021/0104582 A1 | 4/2021 | Kim et al. |
| 2021/0143333 A1 | 5/2021 | Sugitani et al. |
| 2021/0173487 A1 | 6/2021 | Ham |
| 2021/0182008 A1 | 6/2021 | Kim |
| 2021/0192989 A1 | 6/2021 | Ahn et al. |
| 2021/0201713 A1 | 7/2021 | Chung et al. |
| 2021/0208636 A1 | 7/2021 | Kim et al. |
| 2021/0216108 A1 | 7/2021 | Lee et al. |
| 2021/0217839 A1 | 7/2021 | Choi et al. |
| 2021/0226181 A1 | 7/2021 | Seo et al. |
| 2021/0303121 A1 | 9/2021 | Ku |
| 2021/0318730 A1 | 10/2021 | Lee et al. |
| 2021/0320163 A1 | 10/2021 | Bang et al. |
| 2021/0367020 A1 | 11/2021 | Bok et al. |
| 2021/0376033 A1 | 12/2021 | Chae et al. |
| 2021/0384179 A1 | 12/2021 | Bok et al. |
| 2022/0052121 A1 | 2/2022 | Jang et al. |
| 2022/0139326 A1 | 5/2022 | Bae et al. |
| 2022/0149322 A1 | 5/2022 | Kim et al. |
| 2022/0155825 A1 | 5/2022 | Kim et al. |
| 2022/0157250 A1 | 5/2022 | Kim et al. |
| 2022/0187874 A1 | 6/2022 | Chun et al. |
| 2022/0291718 A1 | 9/2022 | Park |
| 2022/0317732 A1 | 10/2022 | Lee et al. |
| 2023/0076158 A1 | 3/2023 | Li et al. |
| 2023/0132649 A1 | 5/2023 | Park |
| 2023/0169901 A1 | 6/2023 | Wu et al. |

\* cited by examiner

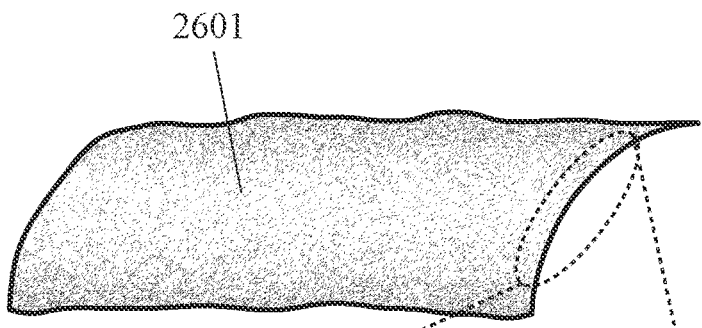
Fig. 26
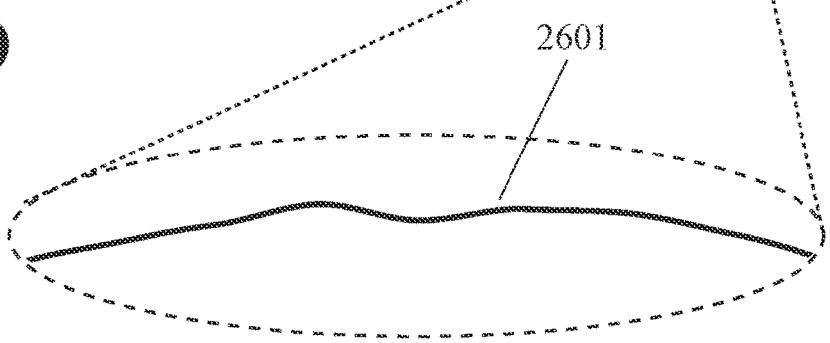
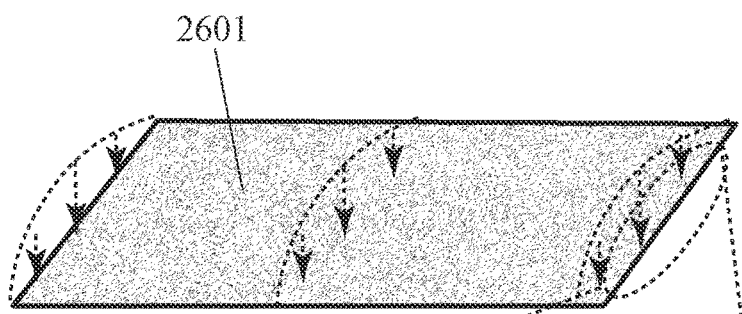
Fig. 27
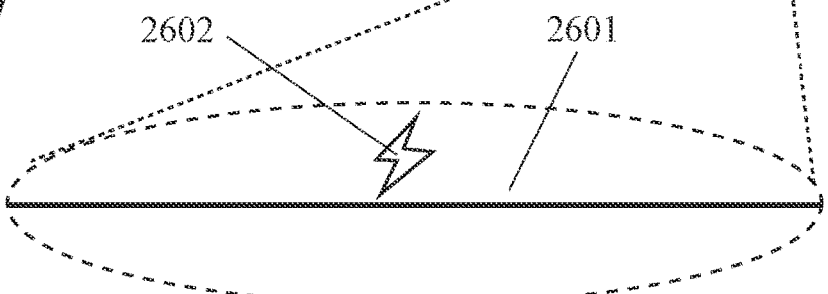

WRIST-WORN DEVICE WITH A VARIABLE-SIZE DISPLAY WHICH IS EXPANDED BY UNROLLING OR SLIDING

CROSS-REFERENCE TO RELATED APPLICATIONS

This application is a continuation in part of U.S. patent application Ser. No. 17/871,952 filed on 2022 Jul. 24. U.S. patent application Ser. No. 17/871,952 was a continuation in part of U.S. patent application Ser. No. 17/515,509 filed on 2021 Oct. 31. U.S. patent application Ser. No. 17/871,952 was a continuation in part of U.S. patent application Ser. No. 16/926,748 filed on 2020 Jul. 12. U.S. patent application Ser. No. 17/871,952 was a continuation in part of U.S. patent application Ser. No. 16/819,147 filed on 2020 Mar. 15.

U.S. patent application Ser. No. 17/515,509 was a continuation in part of U.S. patent application Ser. No. 16/926,748 filed on 2020 Jul. 12. U.S. patent application Ser. No. 16/926,748 was a continuation in part of U.S. patent application Ser. No. 15/431,769 filed on 2017 Feb. 14. U.S. patent application Ser. No. 16/926,748 claimed the priority benefit of U.S. provisional patent application 62/876,213 filed on 2019 Jul. 19. U.S. patent application Ser. No. 16/819,147 was a continuation in part of U.S. patent application Ser. No. 16/598,514 filed on 2019 Oct. 10. U.S. patent application Ser. No. 16/819,147 was a continuation in part of U.S. patent application Ser. No. 15/294,746 filed on 2016 Oct. 16 which issued as U.S. Pat. No. 10,627,861 on 2020 Apr. 21. U.S. patent application Ser. No. 16/819,147 claimed the priority benefit of U.S. provisional patent application 62/882,560 filed on 2019 Aug. 4. U.S. patent application Ser. No. 16/819,147 claimed the priority benefit of U.S. provisional patent application 62/820,337 filed on 2019 Mar. 19.

U.S. patent application Ser. No. 16/598,514 was a continuation in part of U.S. patent application Ser. No. 15/294,746 filed on 2016 Oct. 16 which issued as U.S. Pat. No. 10,627,861 on 2020 Apr. 21. U.S. patent application Ser. No. 16/598,514 was a continuation in part of U.S. patent application Ser. No. 14/623,337 filed on 2015 Feb. 16 which issued as U.S. Pat. No. 9,582,035 on 2017 Feb. 28. U.S. patent application Ser. No. 15/431,769 was a continuation in part of U.S. patent application Ser. No. 14/623,337 filed on 2015 Feb. 16 which issued as U.S. Pat. No. 9,582,035 on 2017 Feb. 28. U.S. patent application Ser. No. 15/294,746 was a continuation in part of U.S. patent application Ser. No. 14/623,337 filed on 2015 Feb. 16 which issued as U.S. Pat. No. 9,582,035 on 2017 Feb. 28.

U.S. patent application Ser. No. 14/623,337 claimed the priority benefit of U.S. provisional patent application 62/115,691 filed on 2015 Feb. 13. U.S. patent application Ser. No. 14/623,337 claimed the priority benefit of U.S. provisional patent application 62/113,423 filed on 2015 Feb. 7. U.S. patent application Ser. No. 14/623,337 claimed the priority benefit of U.S. provisional patent application 62/111,163 filed on 2015 Feb. 3. U.S. patent application Ser. No. 14/623,337 claimed the priority benefit of U.S. provisional patent application 62/106,856 filed on 2015 Jan. 23. U.S. patent application Ser. No. 14/623,337 claimed the priority benefit of U.S. provisional patent application 62/100,217 filed on 2015 Jan. 6. U.S. patent application Ser. No. 14/623,337 claimed the priority benefit of U.S. provisional patent application 61/948,124 filed on 2014 Mar. 5. U.S. patent application Ser. No. 14/623,337 claimed the priority benefit of U.S. provisional patent application 61/944,090 filed on 2014 Feb. 25.

The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to wrist-worn electronic devices with displays.

INTRODUCTION

Smart watches have several advantages over handheld mobile devices. For example, smart watches can incorporate biometric sensors and are less cumbersome than a cell phone for athletic activities. However, a significant disadvantage of conventional smart watches is their small screen size.

REVIEW OF THE RELEVANT ART

U.S. Pat. No. 6,035,035 (Firooz, Mar. 7, 2000, "Wrist Mounted Telephone Device") discloses a wrist-mounted telephone. U.S. patent application publication 20020021622 (Baroche, Feb. 21, 2002, "Multifunction Wristwatch with Electronic Device and Foldable Display Screen") discloses a wrist watch with an unfolding display. U.S. Pat. No. 6,970,157 (Siddeeq, Nov. 29, 2005, "Wearable Computing, Input, and Display Device") discloses a wearable device with a display which can be rotated from a flat position to a raised position.

U.S. Pat. No. 7,558,057 (Naksen et al., Jul. 7, 2009, "Personal Digital Device with Adjustable Interface") discloses a personal digital device with a screen with variable stiffness and size. U.S. patent application publication 20090219788 (Henley, Sep. 3, 2009, "Combination Watch and Cell Phone Foldable onto Each Other for Use Around a Wrist of a User") discloses a combination watch and phone which fold onto each other. U.S. patent application publication 20110187681 (Kim et al., Aug. 4, 2011, "Apparatus for Screen Location Control of Flexible Display") discloses an apparatus to control an image output position of a flexible display.

U.S. patent application publication 20130044215 (Rothkopf, Feb. 21, 2013, "Bi-Stable Spring with Flexible Display") discloses a wearable accessory device with a flexible display coupled to a bi-stable spring. U.S. Pat. No. 8,851,372 (Zhou et al., Oct. 7, 2014, "Wearable Personal Digital Device with Changeable Bendable Battery and Expandable Display Used As Standalone Electronic Payment Card") discloses a wearable device and methods for enlarging its display. U.S. patent application publication 20150029227 (Park et al., Jan. 29, 2015, "Wrist-Wearable Display Apparatus and Method for Controlling the Same") discloses a wrist-wearable apparatus with a hidden display which is exposed if a main display is rotated.

U.S. patent application publication 20150113473 (Otsuka et al., Apr. 23, 2015, "Electronic Device") discloses a wearable touch panel with a first display region and a second display region contiguous with and narrower than the first display region. U.S. patent application publication 20150338882 (Yun et al., Nov. 26, 2015, "Electronic Device with Foldable Display and Method of Operating the Same") discloses a method of operating an electronic device having a foldable display.

U.S. patent application publication 20160239190 (Forutanpour et al., Aug. 18, 2016, "Efficient Display of Content on Wearable Displays") discloses systems, methods, and devices for displaying information in various display regions of a wearable display device, wherein a processor may re-size an image and/or deactivate a portion of the display. U.S. patent application publication 20160240154 (Forutanpour et al., Aug. 18, 2016, "Efficient Operation of Wearable Displays") discloses systems, methods, and devices for displaying information in various display regions of a wearable display device in order to extend battery life.

U.S. patent application publication 20160246558 (Prushinskiy et al., Aug. 25, 2016, "Foldable Display") discloses a foldable display panel including first to fourth regions adjacent to each other. U.S. patent application publication 20160267310 (Al Nasser et al., Sep. 15, 2016, "Wearable Device") discloses a wearable device with a first wrist band unit extended in an opposite direction from a second wrist band unit. U.S. Pat. No. 9,848,494 (Huitema et al., Dec. 19, 2017, "Support Structures for a Flexible Electronic Component") discloses a dynamically flexible article or device, such as a wristband, an armband, a rollable e-reader, or a belt, which includes a flexible display. U.S. Pat. No. 9,877,384 (Lee et al., Jan. 23, 2018, "Display Device") discloses a display device with a flexible display panel and a housing having an outer peripheral surface around which the flexible display panel is rolled. U.S. patent application publication 20180032106 (Yu et al., Feb. 1, 2018, "Rollable Flexible Display Device") discloses a flexible display that rolls or unrolls like a scroll.

U.S. patent application publication 20180120901 (Jin et al., May 3, 2018, "Foldable Display Device and Electronic Apparatus with the Same and Control Method of the Same") and U.S. Pat. No. 10,216,227 (Jin et al., Feb. 26, 2019, "Foldable Display Device and Electronic Apparatus with the Same and Control Method of the Same") disclose a foldable display device with a first display screen, a second display screen, a third display screen, a first connector connecting the first and second screens, and a second connector connecting the second and third screens, wherein the second screen can rotate around the first connector and the third screen can rotate around the second connector.

U.S. patent application publication 20180137801 (An, May 17, 2018, "Flexible Display Device and Displaying Method of Flexible Display Device") discloses a flexible display device including a flexible display and a sensor which obtains user gaze information. U.S. Pat. No. 10,152,028 (Kim, Dec. 11, 2018, "Wristwatch Type Smart Terminal") discloses a wristwatch type smart terminal with a display which can slide or rotate on a band. U.S. Pat. No. 10,299,391 (Kim et al., May 21, 2019, "Rollable Display Device") discloses a rollable display device with a flexible display, including a main roller around which the flexible display is wound and a link drive unit for moving the flexible display.

U.S. Pat. No. 10,319,263 (Lee et al., Jun. 11, 2019, "Flexible Display") discloses a flexible display with a fixing part which has a restoring force that presses on the upper surface of the flexible display. U.S. patent Ser. No. 10/319,331 (Pasupathi, Jun. 11, 2019, "Variable Display Size for an Electronic Display Device") and 10755668 (Pasupathi, Aug. 25, 2020, "Variable Display Size for an Electronic Display Device") disclose an electronic display device configured for variable display size. U.S. patent application publication 20190196550 (Kim et al., Jun. 27, 2019, "Flexible Display Window and Electronic Device Having the Same") discloses a display device with a first portion of a screen which is exposed through a rigid portion and a second of the screen which is extended from the first portion and exposed through a flexible portion.

U.S. patent application publication 20190229288 (Ahn et al., Jul. 25, 2019, "Foldable Display Apparatus") discloses a display that is adjustable between a folded configuration and an unfolded configuration. U.S. patent application publication 20190237532 (Ahn et al., Aug. 1, 2019, "Foldable Display Device") discloses a display panel including a bending portion, and a folding unit supporting the display panel, wherein the display device is capable of being in-folded and out-folded. U.S. patent application publication 20190268455 (Baek et al., Aug. 29, 2019, "Electronic Device Including Movable Flexible Display") discloses a device with an assembly that enables varying a visible portion of a display by extending and retracting a bendable portion of the display.

U.S. patent application publication 20190268771 (Seo et al., Aug. 29, 2019, "Mobile Device of Bangle Type, Control Method Thereof, and UI Display Method") discloses a bangle-type device with a display screen which is changed based on motion. U.S. patent application publication 20190278336 (Choi et al., Sep. 12, 2019, "Electronic Device with Flexible Display and Method for Operating Same") discloses a device with a slideable flexible display. U.S. patent application publication 20190296259 (Baek et al., Sep. 26, 2019, "Electronic Device and Method of Forming Flexible Display Thereof") discloses an electronic device with a display and flexible layer disposed in a recess.

U.S. patent application publication 20190305237 (Shin et al., Oct. 3, 2019, "Electronic Device With Movable Flexible Display and Operating Method Thereof") discloses a flexible touchscreen layer movable between an open state and a closed state. U.S. Pat. No. 10,517,180 (Choi et al., Dec. 24, 2019, "Display Device and Method for Driving the Same") discloses a display device with a flexible display and a rolling driver. U.S. patent application publication 20200042037 (Sun, Feb. 6, 2020, "Wearable Display Device") discloses a wearable display device with a flexible screen and a support component supporting the flexible screen.

U.S. Pat. No. 10,617,017 (Park et al., Apr. 7, 2020, "Rollable Display") discloses a rollable display that can be rolled up and down. U.S. Pat. No. 10,802,544 (Kwak et al., Oct. 13, 2020, "Flexible Display Device and Method of Controlling Same") discloses a flexible display device with a sensor configured to detect at least one rolling characteristic in response to the display being rolled. U.S. Pat. No. 10,820,433 (Cha, Oct. 27, 2020, "Flexible Display Device") discloses a flexible display device with a folded state. U.S. Pat. No. 10,827,630 (Kim et al., Nov. 3, 2020, "Rollable Display") discloses a roller that is bonded to one end of a flexible display panel and allows the flexible display panel to be rolled. U.S. Pat. No. 10,877,525 (Kang et al., Dec. 29, 2020, "Rollable Display") discloses a rollable display, wherein a flexible display panel is rolled onto a panel guide.

U.S. Pat. No. 10,937,393 (Lee et al., Mar. 2, 2021, "Electronic Device Including Flexible Display and Content Display Method Thereof") discloses a flexible display that is rolled up and a sensor configured to detect unrolling of the flexible display. U.S. Pat. No. 10,969,830 (In et al., Apr. 6, 2021, "Flexible Display Device and Method for Compensating Image of Flexible Display Device") discloses a rollable display panel and an optical sensor to detect luminance of the rollable display panel. U.S. patent application publication 20210104582 (Kim et al., Apr. 8, 2021, "Display Apparatus and Electric Apparatus Including the Same") discloses a flexible display panel displaying an image via an upper surface.

U.S. patent application publication 20210143333 (Sugitani et al., May 13, 2021, "Display Apparatus and Method of Manufacturing the Same") discloses a display with a substrate, a conductive layer on the substrate, and an insulating pattern on the conductive layer. U.S. patent Ser. No. 11/016,532 (Yang, May 25, 2021, "Display Device and Moving Method Thereof") discloses a display device with a first roller, a second roller, and a gear coupled to the second roller. U.S. patent application publication 20210173487 (Ham, Jun. 10, 2021, "Display Apparatus") discloses a display panel and a vibration generating device which vibrates the display panel.

U.S. patent application publication 20210182008 (Kim, Jun. 17, 2021, "Display Device") discloses a display device with a roller and a rollable display whose length is adjusted by rotation of the roller. U.S. patent application publication 20210192989 (Ahn et al., Jun. 24, 2021, "Display Device and Method of Providing the Same") discloses a display device with a flexible substrate. U.S. patent application publication 20210201713 (Chung et al., Jul. 1, 2021, "Display Apparatus") discloses a display configured to be wound around first and second rolls.

U.S. patent application publication 20210208636 (Kim et al., Jul. 8, 2021, "Display Device") discloses a display panel with a protective layer. U.S. patent application publication 20210217839 (Choi et al., Jul. 15, 2021, "Display Apparatus and Method of Manufacturing the Same") discloses a display apparatus with a thin film transistor. U.S. patent application publication 20210216108 (Lee et al., Jul. 15, 2021, "Flexible Display Device") discloses a flexible display that can change an area exposed to the outside. U.S. patent application publication 20210226181 (Seo et al., Jul. 22, 2021, "Display Apparatus and Method of Manufacturing the Same") discloses a method of manufacturing a display including a thin film encapsulation layer on a surface of a flexible substrate.

U.S. patent application publication 20210303121 (Ku, Sep. 30, 2021, "Display Device") discloses a base member configured to be folded or unfolded along a folding axis and including a display area. U.S. patent application publication 20210318730 (Lee et al., Oct. 14, 2021, "Display Device") discloses a display device with a substrate, a first sensor electrode, and a second sensor electrode disposed on the substrate. U.S. patent application publication 20210320163 (Bang et al., Oct. 14, 2021, "Display Device") discloses a base with a display area including a plurality of pixels each having at least one switching element and a light-emitting element.

U.S. patent application publication 20210367020 (Bok et al., Nov. 25, 2021, "Foldable Display Device, Rollable Display Device, and Display Device") discloses a foldable display device including a front surface and a rear surface opposite the front surface, wherein the front surface includes a first area with a first transmissive portion and a second area with a second transmissive portion. U.S. patent application publication 20210376033 (Chae et al., Dec. 2, 2021, "Display Panel and Electronic Apparatus") discloses a display panel with a substrate, two pixels on the substrate, and a blocking layer.

U.S. patent application publication 20210384179 (Bok et al., Dec. 9, 2021, "Display Device") discloses a first display area including first sub-pixels to display an image and a second display area including second sub-pixels. U.S. patent application publication 20220052121 (Jang et al., Feb. 17, 2022, "Display Device") discloses a display device including a first base portion and a second base portion. U.S. patent application publication 20220139326 (Bae et al., May 5, 2022, "Display Device") discloses a display panel which displays an image during a plurality of driving frames.

U.S. patent application publication 20220149322 (Kim et al., May 12, 2022, "Display Apparatus and Method of Manufacturing the Same") discloses a display apparatus with a substrate including a polymer resin and a protective layer. U.S. patent application publication 20220155825 (Kim et al., May 19, 2022, "Display Device") discloses a display panel including an area of a constant shape and a shock absorber. U.S. patent application publication 20220157250 (Kim et al., May 19, 2022, "Scan Driver and Display Device Having the Same") discloses a scan driver of a display device including a driving circuit and a masking circuit.

U.S. patent application publication 20220187874 (Chun et al., Jun. 16, 2022, "Rollable Mobile Terminal") discloses a rollable mobile terminal with a flexible display unit and frame. U.S. patent application publication 20220291718 (Park, Sep. 15, 2022, "Flexible Display Device and Control Method Therefor") discloses a flexible display device and a control method therefor. U.S. patent application publication 20220317732 (Lee et al., Oct. 6, 2022, "Flexible Display Apparatus") discloses a flexible display apparatus with a rollable display and a polygonal-prism-shaped roller.

U.S. patent Ser. No. 11/527,179 (Han et al., Dec. 13, 2022, "Display Device") discloses a display panel and a roller around which the display panel is wound or unwound. U.S. patent Ser. No. 11/576,270 (Rha et al., Feb. 7, 2023, "Display Apparatus") discloses a housing provided with an opening at a front surface, a roller disposed within the housing, and a display which is wound around the roller. U.S. patent Ser. No. 11/592,874 (Seger et al, Feb. 28, 2023, "Touch Sensing in a Flexible/Foldable Touch Screen Display") discloses a device having a flexible touch screen display configured to display images in at least a first touch area and a second touch area.

U.S. patent application publication 20230076158 (Li et al., Mar. 9, 2023, "Self-Adaptive Display Aspect Ratio Adjuster and Gesture on Rolling Devices") discloses a device and method for optimizing the size of visual content on a rollable display device. U.S. patent Ser. No. 11/614,777 (Kishimoto et al., Mar. 28, 2023, "Electronic Apparatus and Method for Manufacturing the Same") discloses a display panel having non-folding areas and a folding area between the non-folding areas. U.S. patent application publication 20230132649 (Park, May 4, 2023, "Display Device and Method of Manufacturing the Same") discloses a display device with a substrate having a bent portion and a bending protective layer.

U.S. patent Ser. No. 11/647,598 (Zhang et al., May 9, 2023, "Display Apparatus") discloses a device with a flexible display screen, a fixator, a rotation rod, and an armrest. U.S. patent application publication 20230169901 (Wu et al., Jun. 1, 2023, "Display Panel and Display Device") discloses a rollable display panel with a display region and a non-display region surrounding the display region. U.S. patent Ser. No. 11/699,372 (Lee et al., Jul. 11, 2023, "Electronic Device Including a Flexible Display with Variable Region and Method of Heating the Variable Region of the Flexible Display") discloses an operating method of an electronic device that includes measuring an external temperature via a sensor.

SUMMARY OF THE INVENTION

Smart watches have several advantages over handheld mobile devices. For example, smart watches can incorporate biometric sensors and are less cumbersome than a cell phone for athletic activities. However, a significant disadvantage of conventional smart watches is their small screen size. This invention addresses this problem. Disclosed herein are designs for innovative smart watches with variable-configuration displays which provide the wearer with an expanded display when needed.

This invention is a device with an expandable light-emitting display which is worn on a persons' wrist and/or lower arm. This device can include two displays: a non-expanding first display which is on the dorsal portion of the device; and an expandable second display which is moved from a lateral portion of the device to the dorsal portion before being expanded for use.

The expandable second display can be a flexible display which can be rolled and then expanded by unrolling it out from a housing. In an example, the flexibility of the expandable second display can be adjusted. The second display can be made flexible so that it can be rolled around a roller, but can also be made rigid for use as a touch screen in an expanded state. The expandable second display can comprise a plurality of flexibly-connected segments. When the segments are pulled together, they interlock with each other and make the display more rigid. When the segments are pulled apart, they unlock from each other and make the display more flexible.

In an example, this invention can be embodied in a stand-alone wrist-worn device. In another example, this invention can be embodied in an accessory which is removably-attached to an existing smart watch or other wrist-worn device.

BRIEF DESCRIPTION OF THE FIGURES

FIGS. 26 and 27 show a display made with an electroactive polymer, wherein application of electrical energy to the electroactive polymer makes the display flatter (and more rigid).

DETAILED DESCRIPTION OF THE FIGURES

Figure 1:
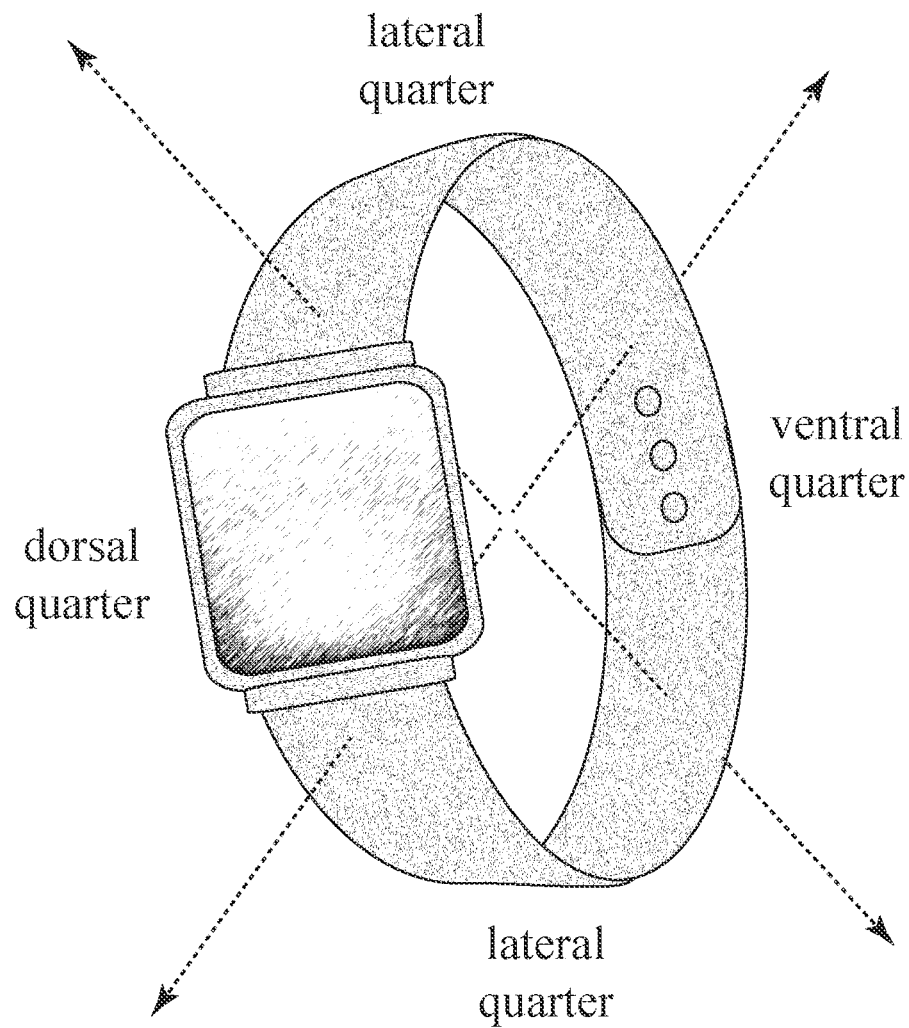
FIG. 1 shows a generic smart watch and the locations of dorsal, ventral, and lateral portions of the watch.

Before discussing specific figures and examples of this invention, it is useful to provide a locational framework which defines terms such as "dorsal" and "ventral" when applied to a person's wrist and/or lower arm. This framework is useful for specifying the locations of components in the wearable devices disclosed herein. In the medical field, the dorsal and ventral sides of a person's wrist and/or lower arm are well-defined. The dorsal side of a person's wrist corresponds to what is more-generally known as the same side as the "back" of a person's hand. The ventral side of a person's wrist corresponds to what is more-generally known as the same side as the "palm" of the person's hand.

For this disclosure, we conceptually divide the circumference of a person's wrist (or lower arm or forearm) into four quarters. This conceptual division results in: (1) a dorsal quarter, which is the quarter of the circumference of a wrist which is centered on the center of the dorsal side of the wrist; (2) the ventral quarter, which is the quarter of the circumference of the wrist which is centered on the center of the ventral side of the wrist; (3) a first lateral quarter, which is between the dorsal quarter and the ventral quarter; and (4) a second lateral quarter, which is between the dorsal quarter and the ventral quarter, and also opposite the first lateral quarter.

The dorsal portion of a wrist-worn device is the portion of the device which is worn over the dorsal quarter of the wrist. Most people wear a conventional watch with the watch housing on the dorsal portion of the watch which is over the dorsal quarter of the circumference of the wrist. The ventral portion of a wrist-worn device is worn on the ventral quarter of the wrist. For a conventional watch with a band which holds the watch housing on the wrist, the ends of the watch band generally meet (e.g. are connected with a buckle or other mechanism) on the ventral portion of the device over the ventral quarter of the wrist. If a wrist-worn device is embodied as a bracelet rather than a smart watch, then the ventral portion of the device need not completely span the ventral quarter or completely encircle the wrist.

In an example, a wearable device with an expandable display can comprise: (a) a wearable device which is configured to be worn around at least three-quarters of the circumference of a person's wrist (or lower arm or forearm), wherein a dorsal portion of the device is configured to be worn on a dorsal quarter of the circumference of the person's wrist, wherein a ventral portion of the device is configured to be worn on at least part of the ventral quarter of the circumference of the person's wrist, wherein a first lateral portion of the device is configured to be worn on a first lateral quarter of the circumference of the person's wrist between the dorsal quarter and the ventral quarter, wherein a second lateral portion of the device is configured to be worn on a second lateral quarter of the circumference of the person's wrist between the dorsal quarter and the ventral quarter, wherein the second lateral quarter is opposite the first lateral quarter; (b) a first light-emitting display on the wearable device, wherein the portion of the device on which the greatest percentage of the first light-emitting display is located is the dorsal portion; and (c) a second light-emitting display on the wearable device, wherein the second light-emitting display has a first configuration in which the portion of the device on which the greatest percentage of the second light-emitting display is located is the first lateral portion or the second lateral portion and the second light-emitting display is a first size, and wherein the second light-emitting display has a second configuration in which the portion of the device on which the greatest percentage of the second light-emitting display is located is the dorsal portion and the second light-emitting display is a second size, and wherein the second size is greater than the first size.

In an example, a device with an expandable display can be worn on a person's wrist (or lower arm or forearm). In an example, a device can be embodied in a form selected from the group consisting of: smart watch, wrist band, fitness band, bracelet, arm band, bangle, cuff, glucose monitor, identification band, sleeve, wearable phone, and wrist watch. In an example, this device can have two displays. In an example, a first display can be located on the dorsal portion of the device. In an example, an expandable second display can flip, pivot, and/or rotate from a lateral portion of the device to the dorsal portion of the device. In an example, a first display can be located on the ventral portion of the device and an expandable second display can flip, pivot, and/or rotate from a lateral portion of the device to the ventral portion of the device. In an alternative example, both first and second displays can be on the dorsal portion of a device. In an alternative example, a first display can remain on the dorsal portion of a device and an expandable second display can remain on a lateral portion of the device.

In an example, a first display can first display an image, wherein an image is understood to broadly encompass any picture, text, or other visual content. In an example, a first display can comprise an array of light emitters which collectively first display a digital image. In an example, a first display can comprise a plurality (e.g. an array or matrix) of light-emitting elements which collectively first display an image (e.g. text, picture, or other visual content). In an example, a first display can be a computer first display and/or screen. In an example, a first display can be a holographic first display. In an example, a first display can comprise light-sensing elements as well as light-emitting elements. In an example, a first display can be a touch screen (e.g. a touch and/or gesture responsive first display). In an example, a flexible first display can serve a human-to-computer input function (e.g. touch screen) in addition to a computer-to-human out function (e.g. image first display).

In an example, a first display can be an Active Matrix Organic Light Emitting Diode (AMOLED) Display. In an example, a first display can be selected from the group consisting of: Active Matrix Organic Light Emitting Diode (AMOLED) Display, Electrophoretic Display (EPD), Phosphorescent OLED (PHOLED) Display, Tunable LED Display, Monochromatic LED (MLED) Display, Surface Conductive Electron Emitter Display (SED), Encapsulated LED Display, Direct-Lit LED Display, Field Emission Display (FED), Interferometric Modulator Display (IMOD), Light Emitting Diode Zep Elyn (LED Zepelyn) Display, Electroluminescent Conductive Polymer Display (ECPD), Light Emitting Diode (LED) Display, Liquid Crystal Display (LCD), Micro-LED Display, Quantum Dot Display (QDD), Plasma Display (PD), Electroluminescent Display (ELD), Electronic Paper (E-Paper) Display, Carbon Nanotubes Display (CND), Holographic Display, Quantum Dot LED (QLED) Display, Electro-Wetting Display (EWD), Super-Luminescent Light Emitting Diode (SLED) Display, Edge-Lit LED (ELED) Display, Electrochromic Display (ECD), Organic Light Emitting Diode (OLED) Display, Thin Film Transistor LCD (TFT LCD) Display, Digital Microshutter Display (DMS), Mini-LED Display, e-ink display (E-ink), and Resonant Cavity Light Emitting Diode (RCLED) Display.

In an example, a first display can be on the dorsal portion of a device, which is over the dorsal quarter of the circumference of a person's wrist. This corresponds to the way in which most people wear a smart watch, with the watch housing worn on the dorsal side of their wrist. In an example, a first display can be entirely within a dorsal portion of a device. In an example, a first display can be entirely over the dorsal quarter of the circumference of a person's wrist.

In an example, a first display can be larger than the dorsal portion of a device, but still be centered on the dorsal portion. In an example, the portion of a device (among the four portions dorsal, ventral, first lateral, and second lateral) on which the greatest percentage of a first light-emitting display is located can be the dorsal portion. In an example, a first display can be centered on the center of the dorsal portion. In an example, a first display can be located entirely on the dorsal portion of the device. In an example, a first display can be so large that it covers more than just the dorsal quarter of a device. In an example, at least 75% of a first display can be on the dorsal portion of the device.

In an example, a first display can be rigid and flat, like a display on a traditional smart watch. In an example, a first display can be non-expandable, non-flexible, non-bendable, and non-rollable. In an example, a first display can have a static size; its size does not change over time. In an example, a first display can have a static location; it does not move relative to the rest of the device. In an example, a first display can have a shape which is selected from the group consisting of: polygonal, square, square with rounded vertexes, rectangle, rectangle with rounded vertexes, hexagonal, convex, and circular. In an example, a first display can serve as the primary display for a device when a second display is in a first configuration. In an example, a first display can be covered by a second display when the second display is in a second configuration.

In an example, a device can have a second display in addition to a first display. In an example, a second display can be expandable. In an example, a second display can be expanded from a first configuration with a first size to a second configuration with a second size, wherein the second size is greater than the first size. In an example, the second size can be at least twice the first size. In an example, a second display can be flexible. In an example, a second display can be rollable. In an example, a second display can be bent, curved, and/or folded. In an example, a second display can be bendable so that it can be rolled or unrolled without damage to the display. In an example, a second display can be bendable so that it can be folded or unfolded without damage to the display.

In an example, a second display can first display an image, wherein an image is understood to broadly encompass any picture, text, or other visual content. In an example, a flexible second display can comprise an array of light emitters which collectively first display a digital image. In an example, a second display can comprise a plurality (e.g. an array or matrix) of light-emitting elements which collectively second display an image (e.g. text, picture, or other visual content). In an example, a second display can be a computer second display and/or screen. In an example, a second display can be a holographic second display. In an example, a second display can comprise light-sensing elements as well as light-emitting elements. In an example, a second display can be a touch screen (e.g. a touch and/or gesture responsive second display). In an example, a flexible second display can serve a human-to-computer input function (e.g. touch screen) in addition to a computer-to-human out function (e.g. image second display).

In an example, a second display can be an Active Matrix Organic Light Emitting Diode (AMOLED) Display. In an example, a second display can be selected from the group consisting of: Active Matrix Organic Light Emitting Diode (AMOLED) Display, Electrophoretic Display (EPD), Phosphorescent OLED (PHOLED) Display, Tunable LED Display, Monochromatic LED (MLED) Display, Surface Conductive Electron Emitter Display (SED), Encapsulated LED Display, Direct-Lit LED Display, Field Emission Display (FED), Interferometric Modulator Display (IMOD), Light Emitting Diode Zep Elin (LED Zep Elin) Display, Electroluminescent Conductive Polymer Display (ECPD), Light Emitting Diode (LED) Display, Liquid Crystal Display (LCD), Micro-LED Display, Quantum Dot Display (QDD), Plasma Display (PD), Electroluminescent Display (ELD), Electronic Paper (E-Paper) Display, Carbon Nanotubes Display (CND), Holographic Display, Quantum Dot LED (QLED) Display, Electro-Wetting Display (EWD), Super-Luminescent Light Emitting Diode (SLED) Display, Edge-Lit LED (ELED) Display, Electrochromic Display (ECD), Organic Light Emitting Diode (OLED) Display, Thin Film Transistor LCD (TFT LCD) Display, Digital Microshutter Display (DMS), Mini-LED Display, e-ink display (E-ink), and Resonant Cavity Light Emitting Diode (RCLED) Display.

In an example, a second display can be flipped, pivoted, and/or rotated from a first location to a second location on a wrist-worn device. In an example, a second display can be pivoted from a primarily lateral location to a primarily dorsal location on a wrist-worn device. In an example, a second display can be rotated from a primarily lateral location to a primarily dorsal location on a wrist-worn device and then expanded. In an example, a second display can be flipped from a primarily lateral location to a primarily dorsal location on a wrist-worn device. In an example, a second display can be moved from one portion of a device to another portion of the device before being rotated and expanded.

In an example, when a second display is in a first configuration, then the portion of the device among the four portions (dorsal, ventral, first lateral, and second lateral) on which the greatest percentage of the second light-emitting display is located is a lateral portion. In an example, when a second display is in a first configuration, then a second display can be located primarily on the lateral portion of the device. In an example, when a second display is in a first configuration, then at least 75% of a second display can be located on the lateral portion of the device. In an example, when a second display is in a first configuration, then at least 50% of a second display can be located on the lateral portion of the device. In an example, when a second display is in a first configuration, then a second display can be centered on the center of the lateral portion of the device.

In an example, when a second display is in a second configuration, then the portion of the device among the four portions (dorsal, ventral, first lateral, and second lateral) on which the greatest percentage of the second light-emitting display is located is a dorsal portion. In an example, when a second display is in a second configuration, then a second display can be located primarily on the dorsal portion of the device. In an example, when a second display is in a second configuration, then at least 75% of a second display can be located on the dorsal portion of the device. In an example, when a second display is in a second configuration, then at least 50% of a second display can be located on the dorsal portion of the device. In an example, when a second display is in a second configuration, then a second display can be centered on the center of the dorsal portion of the device.

In an alternative example, a second display can be on a ventral portion of the device in both its first and second configurations. In an example, a second display can be on a lateral portion of the device in both its first and second configurations. In an example, a second display can be on a dorsal portion of a device in both its first and second configurations. In an example, both first and second displays can be primarily on the dorsal portion of the device. In an example, a second display can be located entirely on the dorsal portion of the device.

In an example, a second display can be within a housing when the display is in its first (non-expanded) configuration. In an example, this housing can be larger than the closest side of a first display. In an example, this housing can have a longitudinal axis which is parallel to the plane of the circumference of the device. In an example, this housing can have a longitudinal axis which is parallel to the plane of the circumference of the device. In an example, a housing that contains the second display can be on one side of a first device. In another example, this housing can have a longitudinal axis which is perpendicular to the plane of the circumference of the device.

In an example, (a layer of) a flexible display can be made with one or more materials selected from the group consisting of: Amorphous Silicon (AS), Benzocyclobutene (BCB), Calcium Fluoride (CF), carbon nanotubes, Cellulose Acetate Propionate (CAP), Cellulose Triacetate (CAT), Epoxy, Fiber Reinforced Plastic (FRP), Fluorine-Doped Quartz Substrate, Graphene, Indium Tin Oxide (ITO), Polyacrylate (PA), Polyarylate (PAR), Polycarbonate (PC), Polycrystalline Silicon (PS), Polydarton (PD), Polyether Ether Ketone (PEEK), Polyether Imide (PI), Polyether Sulfone (PES), Polyetherimide (PEI), Polyethylene Naphthalate (PEN), Polyethylene Terephthalate (PET), Polyimide (PI), Polyphenylene Sulfide (PPS), Polysilicon, Shape Memory Material, Triacetate Cellulose (TAC), and Urethane.

In an example, a second display can be rollable. In an example, a second display can be rolled (e.g. rolled, wound, coiled, spiraled, and/or scrolled) or unrolled (e.g. unrolled, unwound, and/or uncoiled, un-spiraled, and/or unscrolled) without damage to the display. In an example, a flexible second display can be expanded (e.g. expanded, extended, lengthened, and/or widened) by being unrolled (e.g. unrolled, unwound, and/or uncoiled, un-spiraled, and/or unscrolled) from a roller (e.g. roller, spool, cylinder, rod, or pin).

In an example, a second display can be rolled (e.g. rolled, wound, coiled, spiraled, and/or scrolled) around a roller (e.g. roller, spool, cylinder, rod, or pin) and also unrolled (e.g. unrolled, unwound, and/or uncoiled, un-spiraled, and/or unscrolled) from the roller (e.g. roller, spool, cylinder, rod, or pin) without damage to the display. In an example, a second display can be rolled (e.g. rolled, wound, coiled, spiraled, and/or scrolled) around a roller (e.g. roller, spool, cylinder, rod, or pin) and contained in the housing in a first configuration. In an example, a second display can be unrolled (e.g. unrolled, unwound, and/or uncoiled, un-spiraled, and/or unscrolled) from a roller (e.g. roller, spool, cylinder, rod, or pin) and extend out from the housing in a second configuration.

In an example, a second display can be rolled (e.g. rolled, wound, coiled, spiraled, and/or scrolled) around a roller (e.g. roller, spool, cylinder, rod, or pin) in the housing in a first unexpanded configuration and unrolled (e.g. unrolled, unwound, and/or uncoiled, un-spiraled, and/or unscrolled) from that roller (e.g. roller, spool, cylinder, rod, or pin) in a second expanded (e.g. expanded, extended, lengthened, and/or widened) configuration.

In an example, a flexible second display can be expanded (e.g. expanded, extended, lengthened, and/or widened) from its unexpanded first configuration to its second expanded (e.g. expanded, extended, lengthened, and/or widened) configuration as it is unrolled (e.g. unrolled, unwound, and/or uncoiled, un-spiraled, and/or unscrolled) from a roller (e.g. roller, spool, cylinder, rod, or pin). In an example, an expandable display can be a flexible display which is unrolled (e.g. unrolled, unwound, and/or uncoiled, un-spiraled, and/or unscrolled) from its first unexpanded configuration to its second expanded (e.g. expanded, extended, lengthened, and/or widened) configuration.

In an example, the outward-facing and/or visible size of a second display can be reduced by rolling (one end of) the display around a roller (e.g. roller, spool, cylinder, rod, or pin). In an example, the outward-facing and/or visible surface area of a second display can be reduced by rolling (one end of) the display around a roller (e.g. roller, spool, cylinder, rod, or pin). In an example, the outward-facing and/or visible size of a second display can be increased by unrolling (one end of) the display from around the roller (e.g. roller, spool, cylinder, rod, or pin). In an example, the outward-facing and/or visible surface area of a second display can be increased by unrolling (one end of) the display from around the roller (e.g. roller, spool, cylinder, rod, or pin).

In an example, a flexible second display can be looped around one or more rollers, wherein looping means that the display curves and/or bends partially around the circumference of the roller but not around the entire circumference of the roller. In an example, a flexible second display can be looped around one or more rollers, wherein looping means that the display curves and/or bends partially around the circumference of the roller but does not roll (e.g. roll, coil, wind, or spiral) completely around the circumference of the roller.

In an example, a flexible second display which loops around a roller can have a first (unexpanded) configuration in which the display overlaps itself to a first extent and a second (expanded) configuration in which the display overlaps itself to a second extent. In an example, the second extent can be less than the first extent. In an example, when the second display moves into the second (expanded) configuration, the visible portion of the display which extends out from a housing can be increased.

In an example, a flexible second display which loops around a roller can loop around a roller, wherein an upper portion of the display is above the center of the roller and the a lower portion of the display is below the center of the roller. When the rolled is rotated, then the relative amounts of the display in the upper and lower portions change. In an example, when the amount of the display in the upper portion is increased, then the visible portion of the display increases. In an example, the second display extends outward as the side of the lower portion of the display loops upward, around the roller, and becomes part of the upper portion of the display. In an alternative example, when the amount of the display in the power portion is increased, then the visible portion of the display increases.

In an example, a flexible second display can be looped around two rollers. In an example, a flexible second display can be looped around and between two rollers. In an example, a flexible second display can be looped around and between three or more rollers in a back and forth, serpentine and/or zig-zag manner. In an example, changing the distance between two or more rollers can extend (e.g. expand) the visible portion of the display.

In an example, one end (or side) of a flexible display can be attached to a roller and the display can be rolled around the roller as the roller is rotated. In an example, a device can have two rollers, wherein two opposite ends (or sides) of a flexible display can be attached to and rolled around those two rollers, respectively. In an example, one side of a flexible display can be rolled to decrease the visible size of the display and can be unrolled from the roller to increase the visible size of the display. In an example, this roller can be inside the housing.

In an example, a roller around which a second display is rolled can have a circular cross-sectional shape. In an example, a roller around which a second display is rolled can have an elliptical or oval cross-sectional shape. In an example, a roller around which a second display is rolled can have a polygonal (e.g. square or hexagonal) cross-sectional shape. In an example, a roller around which a second display is rolled, coiled, and/or wound can have a radially-asymmetric cross-sectional shape.

In an example, a roller can have a cog and/or gear shape. In an example, a roller can be embodied in a cogwheel and/or gear. In an example, a roller (e.g. roller, spool, cylinder, rod, or pin) around which a second display is rolled (e.g. rolled, coiled, wound, spiraled, and/or scrolled) can have a cogwheel, gear, and/or sun-burst cross-sectional shape. In an example, a roller around which a second display is rolled, coiled, and/or wound can have an involute curve tooth cross-sectional shape. In an example, a roller can have teeth (e.g. teeth, notches, gears, and/or protrusions) which engage the display as the display is rolled around or unrolled from the roller. In an example, the edges of an expandable display can have teeth or openings are engaged by one or more gears and/or cogs on a roller. In an example, the perimeter of an expandable display can have teeth or openings are engaged by a gear-shaped or cogwheel-shaped roller.

In an example, protrusions or recesses on a display can interdigitate (e.g. interdigitate, engage, and/or mesh) with the recesses or protrusions on a roller. In an example, a roller (e.g. roller, spool, cylinder, rod, or pin) can comprise a gear which engages protrusions or recesses (e.g. teeth, ridges, notches, or undulations) on the lower surface of a second display. In an example, the edges of an expandable second display can have teeth or openings are engaged by a gear-shaped roller to pull the display around a roller or push the display away from the roller.

In an example, a roller can have teeth, cogs, and/or gears which engage a flexible display, thereby pulling the display around the roller as the display is being rolled or pushing the display off the roller as the display is being unrolled. In an example, the lower surface and/or the lateral sides of the second display can have protrusions or recesses (e.g. teeth, ridges, notches, or undulations) and the roller (e.g. roller, spool, cylinder, rod, or pin) around which the display is rolled, coiled, and/or wound can have recesses or protrusions (e.g. teeth, ridges, notches, or undulations) which are geometrically complementary to those of the display.

In an example, a flexible display can pass (e.g. be threaded, slid, and/or compressed) between two parallel guide rollers. In an example, a flexible display can pass between two guide rollers before it is being rolled (e.g. rolled, coiled, and/or wound) around a primary roller. In an example, a flexible display can pass between two guide rollers as it is being unrolled (e.g. unrolled, uncoiled, and/or unwound) from the primary roller. In an example, two guide rollers can rotate in opposite directions (e.g. one clockwise and the other counter-clockwise) as a display passes between them. In an example, guide rollers can help the display to roll evenly onto (or off from) the primary roller.

In an example, guide rollers can help to maintain proper tension on a display. In an example, guide rollers can help to flatten a display. In an example, guide rollers can push together connected segments which comprise the display so that these segments interlock with each other and the display becomes more rigid. In an example, guide rollers can have teeth (e.g. teeth, notches, cogs, and/or protrusions) which engage the display as the display passes between them. In an example, guide rollers can be shaped like (and/or function as) cogwheels and/or gears. In an example, guide rollers can be rotated automatically by one or more electromagnetic actuators to actively pull the display as it passes between them.

In an example, a wearable device can be expanded by a roller mechanism. This roller mechanism can include a spring to maintain tension on the display. In an example, a roller mechanism can include a spring or other tension member which is attached to a guide roller, in addition to a primary roller. In an example, a spring-bound guide roller can maintain tension on the display as the display is rolled or unrolled.

In an example, a roller can be rotated by an actuator and/or miniature motor. In an example, a roller can be engaged and rotated by an actuator and/or miniature motor through gears and/or cogs. In an example, a roller can be engaged and rotated by an actuator and/or miniature motor by a drive belt. In an example, a roller can be rotated automatically by one or more electromagnetic actuators to actively engage (e.g. push or pull) a display.

In an example, the rotational speed of a roller can be varied and/or adjusted. In an example, the rotational speed of a roller can increase in proportion to the amount of the flexible display which is rolled (e.g. rolled, coiled, wound, scrolled, and/or spiraled) around the roller. In an example, the rotational speed of a roller can start out slower and then increase as more of the flexible display is rolled (e.g. rolled, coiled, wound, scrolled, and/or spiraled) around the roller. In an example, the rotational speed of a roller can start out faster and then decrease as more of the flexible display is rolled (e.g. rolled, coiled, wound, scrolled, and/or spiraled) around the roller. In an example, the rotational speed of a roller can start out slower as one end of a flexible display is started to be rolled (e.g. rolled, coiled, wound, scrolled, and/or spiraled) around the roller, can become faster as the middle of the display is rolled, and then be slower again are the display nears being completely rolled.

In an example, a device can have a roller located on one side of a flexible display. In an example, a flexible display can be rolled around a single roller. In an example, a flexible display can be rolled around two or more rollers. In an example, a device can have two roller mechanisms on opposite sides of a flexible display. In an example, a device can have two rollers around which a flexible display is rolled. In an example, a device can have two rollers around which two sides of a flexible display are rolled. In an example, a device can have two rollers, one on each side of the flexible display. In an example, the two rollers can be parallel to each other.

In an example, the distance between the two rollers can be changed. In an example, the two rollers can be moved farther apart from each other when the flexible display is expanded in two opposite directions. In an example, two rollers can rotate in opposite (e.g. clockwise vs. counter-clockwise) directions as a flexible display is expanded. In an example, one side of the flexible display can be rolled around a first roller and the opposite side of the flexible display can be rolled around a second roller. In an example, the flexible display can be expanded in a first direction by being unrolled from the first roller and expanded in a second direction by being unrolled from the second roller.

In an example, a flexible display can be looped back and forth between two or more rollers, forming three portions: a first (upper) portion which extends out from a first (upper) roller, a second (middle) portion which spans between the first (upper) roller and the second (lower) roller, and a third (lower) portion which spans extends out from the third (lower) roller. In an example, these three portions of the flexible display can be parallel to each other. In an example, as the two or more rollers are moved closer together, the first (upper) portion is increased.

In an example, when the distance the two or more rollers is decreased, then the portion of the flexible display which is looped between them decreases and the flexible display extends outward from the roller mechanism. In an example, when the distance the two or more rollers is increased, then the portion of the flexible display which is looped between them increases and the flexible display is drawn into the roller mechanism. In an example, the (outward-facing) size of a flexible display can be increased by decreasing the distance between two or more rollers around which a flexible display is looped.

In an example, a flexible display can be rolled around a first roller and looped around a second roller. In an example, a flexible display can be rolled, coiled, and/or wound around a first roller (e.g. roller, spool, cylinder, rod, or pin) and looped around (e.g. bent around part of the circumference of) a second roller (e.g. roller, spool, cylinder, rod, or pin). In an example, a flexible display can overlap itself to a first extent in a non-expanded configuration and overlap itself to a second extent in an expanded configuration, wherein the second extent is less than the first extent.

In an example, a second display can have a rectangular shape. In an example, a second display can have an arcuate (e.g. curved) rectangular shape. In an example, a second display can have a shape which is selected from the group consisting of: polygonal, square, square with rounded vertexes, rectangle, rectangle with rounded vertexes, hexagonal, convex, and circular.

In an example, a second display can be arcuate in a first (unexpanded) configuration and flat in a second (expanded) configuration. In an example, a second display can be flat in its expanded configuration. In an example, a second display can be flexible so that it can change between being flat (e.g. planar) and arcuate (e.g. curved) without the display being damaged. In an example, a second display can be flexible so that it can change between flat, concave, and convex shapes. In an example, a second display can be longitudinally-concave in its first configuration and longitudinally-flat in its second configuration. In an example, a second display can be longitudinally-convex in its first configuration and longitudinally-flat in its second configuration.

In an example, a second display can have an arcuate shape which is substantially parallel to the arcuate shape of a lateral portion of the device when the second display is in its first configuration. In an example, a second display in its first configuration can be arcuate. In an example, a second display can be convex in a first (unexpanded) configuration and concave in a second (expanded) configuration. In an example, the second display in its first configuration can curve around the person's wrist. In an example, the shape of a second display in its first configuration can be a section of cylinder which is substantially parallel to the surface of a person's wrist.

In an example, a second display can have a rectangular shape in its expanded configuration. In an example, a second display can have a rounded rectangular shape (e.g. rectangle with rounded vertexes) in its expanded configuration. In an example, a second display can have a square (or square with rounded vertexes) shape in its first (unexpanded) configuration and a rectangular (or rectangular with rounded vertexes) shape in its second (expanded) configuration. In an example, a second display can have a square (or square with rounded vertexes) shape in its first (unexpanded) configuration and a rectangular (or rectangular with rounded vertexes) shape in its second (expanded) configuration, wherein a narrow side of the rectangle is equal in length to a side of the square. In an example, a second display can have a square (or square with rounded vertexes) shape with a first size in its first (unexpanded) configuration and a square (or square with rounded vertexes) shape with a second size in its second (expanded) configuration, wherein the second size is at least twice as large as the first size.

In an example, a second display, even in its first configuration, can be larger than a first display. In an example, a second display can have the same width as a first display, along an axis which is perpendicular to the plane of the circumference of the device, but have a length which is at least 50% greater than the length of a first display, along an axis which is parallel to the plane of the circumference of the device. In an example, a second display can span between 20% and 40% of the circumference of a person's wrist and/or lower arm in its first configuration. In an example, the size of a second display in its second configuration can be between 150% and 300% of the size of the second display in its first configuration. In an example, the size of a second display in its second configuration can be at least twice the size of the second display in its first configuration.

In an example, an image-displaying surface of a second display can face inward (toward the surface the person's wrist) in a first configuration and can face outward (away from the surface of the person's wrist) after the display has been flipped, pivoted, and/or rotated from the first configuration into a second configuration. In an example, an image-displaying surface of a second display can face inward (facing away from and not being visible to the user) in a first configuration and can face outward (facing toward and being visible to the user) after the display has been flipped, pivoted, and/or rotated from the first configuration into a second configuration.

In an example, the edges of an expandable display can have teeth or openings are engaged by a cog and/or gear shaped roller. In an example, the edges of an expandable display can have teeth or openings are engaged by a cog and/or gear shaped roller to pull the display around the roller or push the display away from the roller. In an example, the lower surface and/or the lateral sides of a second display can have protrusions or recesses (e.g. teeth, ridges, notches, or undulations) and a roller (e.g. roller, spool, cylinder, rod, or pin) around which the display is rolled, coiled, and/or wound can have recesses or protrusions (e.g. teeth, ridges, notches, or undulations) which are geometrically complementary to those of the display. In an example, the protrusions or recesses on a second display can interdigitate (e.g. interdigitate, engage, and/or mesh) with the recesses or protrusions on the roller.

In an example, a second display can be flipped from a first location to a second location on a wrist-worn device. In an example, a second display can be flipped from a first location to a second location on a wrist-worn device and then expanded. In an example, a second display can be flipped from a primarily lateral location to a primarily dorsal location on a wrist-worn device and then expanded. In an example, a second display can be changed from its first configuration to its second configuration by being flipped (e.g. flipped, pivoted, folded, and/or rotated) from a location primarily along a lateral portion of a wrist-worn device to cover the first display and then expanded away from the plane of the circumference of the device.

In an example, a second display can be changed from its first configuration to its second configuration by being flipped (e.g. flipped, pivoted, folded, and/or rotated) from a location primarily along a lateral portion of a wrist-worn device to a location primarily along the dorsal portion of the wrist-worn device and then expanded away from the plane of the circumference of the device. In an example, a second display can be pivoted from a first location to a second location on a wrist-worn device and then expanded. In an example, a second display can be rotated from a first location to a second location on a wrist-worn device and then expanded.

In an example, a second display can be flipped, rotated, and/or pivoted. In an example, a second display can be flipped, rotated, and/or pivoted before it is expanded. In another example, a second display can be expanded before being flipped, rotated, and/or pivoted. In an example, a second display can be rotated around its center before being expanded. In an example, a second display can be rotated around its central cross-sectional axis before being expanded. In an example, a second display can be rotated 90 degrees before being expanded. In an example, a second display can be rotated between 40 and 140 degrees before being expanded. In an example, a second display can be rotated around a non-central axis. In an example, a second display can be rotated around one of its sides or vertexes before it is expanded. In an example, a second display can be rotated (e.g. rotated or pivoted) around an edge or vertex of the second display.

In an example, a second display can have a longitudinal axis which is orthogonal to the plane of the circumference of the device in a first configuration and can have a longitudinal axis which is parallel to the plane of the circumference of the device in the second configuration. In an example, a second display can have a longitudinal axis which is parallel to the plane of the circumference of the device in a first configuration and can have a longitudinal axis which is orthogonal to the plane of the circumference of the device in the second configuration. In an example, a longitudinal axis of a second display can be rotated from a first configuration which is parallel to the plane of the circumference of a device to a second configuration which is perpendicular to that plane. In an example, a longitudinal axis of a second display can be rotated from a first configuration which is perpendicular to the plane of the circumference of a device to a second configuration which is parallel to that plane.

In an example, a second display can be changed from its first configuration to its second configuration in two steps. In an example, a second display can be moved relative to the rest of a wrist-worn device in a first step and then it can be expanded in a second step. In an example, a second display can be changed from its first configuration to its second configuration by being moved relative to the rest of a wrist-worn device and then expanded. In an example, a second display can be changed from its first configuration to its second configuration by being moved from around the circumference (e.g. from one quarter portion to another) of a wrist-worn device and then expanded away from the plane of the circumference of the device. In an example, a second display can be changed from its first configuration to its second configuration by being moved from a location primarily along a lateral portion of a wrist-worn device to a location primarily along the dorsal portion of the wrist-worn device before the second display is expanded away from the plane of the circumference of the device.

In an example, a second display can be expanded first and then moved relative to the rest of a wrist-worn device. In an example, a second display can be changed from its first configuration to its second configuration by being expanded and then moved relative to the rest of a wrist-worn device. In an example, a second display can be changed from its first configuration to its second configuration by being expanded away from the plane of the circumference of the device and then moved from around the circumference (e.g. from one quarter portion to another) of a wrist-worn device. In an example, a second display can be changed from its first configuration to its second configuration by being expanded away from the plane of the circumference of the device and then moved from a location primarily along a lateral portion of a wrist-worn device to a location primarily along the dorsal portion of the wrist-worn device.

In an example, a second display can be changed from its first configuration to its second configuration by being slid (e.g. slid or shifted along the circumference of the wrist-worn device) from a location primarily along a lateral portion of a wrist-worn device to a location primarily along the dorsal portion of the wrist-worn device and then expanded away from the plane of the circumference of the device. In an example, a second display can slide around part of the circumference of a device along tracks (e.g. tracks, channels, or grooves). In an example, a device can have two parallel tracks along which a second display slides. In an example, a second display can have protrusions (e.g. prongs, knobs, bulbs, hooks, or balls) which protrude into the tracks, holding the second display snuggly on the device as the display slides around part of the circumference of the device. In an example, the display can be manually slid along the tracks. In an example, the display can be automatically slid along the tracks by an electromagnetic actuator.

In an example, a second display can be manually moved from its first configuration to its second configuration. In an example, a second display can be manually flipped, pulled, pushed, pressed, and/or slid from, its first configuration to its second configuration by the person wearing the device. In an example, a second display can be manually expanded when user pulls a side (or end) of the display which is opposite to a roller (e.g. roller, spool, cylinder, rod, or pin) around which the display is rolled, wound, and/or coiled. In an example, a second display can be selectively and reversibly locked into its first configuration or its second configuration by the person wearing the device.

In another example, a second display can be automatically moved from its first configuration to its second configuration by one or more actuators. In an example, a second display can be automatically expanded when an actuator rotates a roller (e.g. roller, spool, cylinder, rod, or pin) around which the display is rolled, wound, and/or coiled, thereby unrolling, unwinding, and/or uncoiling the display.

In an example, one end (or side) of a second display can be permanently attached to the rest of the device by a hinge and/or movable joint. In an example, a dorsal-facing end (or side) of a second display can be permanently attached to the rest of the device by a hinge and/or movable joint. In an example, this hinge and/or movable joint can be orthogonal to the plane of the circumference of the wearable device. In an example, this hinge and/or movable joint can be perpendicular to the circumference of the wearable device. In an example, the hinge and/or moveable joint can be on the dorsal portion of the device (over the dorsal quarter of the person's wrist).

In an example, an end of a second display which is not attached to a hinge and/or movable joint can move toward in a dorsal direction as the display is changed from its first configuration to its second configuration. In an example, an end of a second display which is not attached to a hinge and/or movable joint can move toward in a dorsal direction as the display as one step of a second display changing from its first configuration to its second configuration.

In an example, a wearable device can comprise a hinge and/or movable joint around which a second display flips, pivots, folds, and/or rotates as a second display is changed from its first configuration to its second configuration, or vice versa. In an example, a wearable device can comprise a hinge and/or movable joint around which a second display flips, pivots, and/or rotates in one step of a second display changing from its first configuration to its second configuration, or vice versa.

In an example, the ventral-facing end of a second display can be reversibly attached to (or detached from) the rest of the device by a snap, clip, clasp, magnet, hook-and-loop fabric, hook, pin, or buckle. In an example, the ventral-facing end of a second display can be (detached and) moved away from the rest of the device in order to flip, pivot, and/or rotate a second display from its first configuration to its second configuration.

In an example a ventral side (or end) of second display can be releasably-connected to the rest of the device (e.g. by a snap, clip, magnet, pin, hook, or hook-and-loop fabric), wherein it is connected in the first configuration and disconnected in the second configuration. In an example, a dorsal side (or end) of a second display can be connected to the rest of the device by one or more hinges and/or moveable joints, around which a second display flips, pivots, and/or rotates from its first configuration to its second configuration.

In an example, a second display can comprise a plurality of flexibly-connected segments. In an example, a second display can comprise a plurality of flexibly-connected hexagonal segments. In an example, a second display can comprise a plurality of rectangular segments which are flexibly connected along their longitudinal (longer) sides. In an example, a second display can comprise a plurality of parallel rectangular segments which are flexibly connected along their longitudinal (longer) sides. When the segments are sufficiently small relative to the overall second display, the overall second display can be relatively flexible, bendable, and rollable. In an example, a second display can comprise between 20 and 60 flexibly-connected segments. In an example, a second display can comprise between 50 and 100 flexibly-connected segments.

In an example, a second display can comprise a plurality of adjustably-connected segments with interdigitated protrusions and recesses. In an example, a second display can comprise a plurality of adjustably-connected tongue-and-groove segments with interdigitated protrusions and recesses. In an example, a second display can comprise a plurality of adjustable-connected segments (e.g. tongue-and-groove segments) which enable the flexibility and/or bendability of the second display to be adjusted. In an example, a second display can comprise a plurality of adjustable-connected segments (e.g. tongue-and-groove segments) with interdigitated protrusions and recesses so that the flexibility and/or bendability of the second display can be adjusted.

In an example, a second display can comprise a plurality of rectangular adjustably-connected tongue-and-groove segments with interdigitated protrusions and recesses so that the flexibility of the second display can be adjusted. In an example, a second display can have a layer which comprises a plurality of flexibly-connected rigid segments which interlock when they are drawn closer to each other, thereby making the second display more rigid. In an example, a second display can have a layer which comprises a plurality of flexibly-connected tongue-and-groove segments which interlock when they are drawn closer to each other, thereby making the second display more rigid.

In an example, segments in a plurality of adjustably-connected segments can be shaped like tongue-and-groove floor boards, wherein a protrusion on a side of a first segment fits into a recess on a side of an adjacent second segment when the two segments are pushed (or pulled) close together. Unlike floor boards which are pushed together (e.g. by the lateral force of a hammer) into a permanently-interdigitated configuration, segments in a second display can be reversibly pulled (or pushed) closer together or father apart. When these segments are pulled (or pushed) closer together, they interlock and the display becomes more rigid.

In an example, the flexibility and/or rigidity of the second display can be changed. In an example, the second display can be made more flexible to facilitate moving it from its first configuration to its second configuration, but can then be made more rigid to facilitate a stable, flat image (and/or its use as a touch screen). In an example, a second display can further comprise (a layer of) a plurality of narrow rigid connected sections, wherein the second display becomes more flexible (less rigid) when the sections are more loosely connected to each other and the second display becomes more rigid (less flexible) when the sections are more tightly connected to each other. In an example, the degree to which sections are loosely or tightly connected to each other can be adjusted.

In an example, the spacing between flexibly-connected segments comprising a display can be changed (e.g. adjusted) in order to change (e.g. adjust) the flexibility and/or rigidity of the display. In an example, a second display can comprise a plurality of adjustably-connected segments so that the flexibility of the second display can be adjusted. In an example, a second display can have a layer of adjustably-connected segments so that the flexibility of the second display can be adjusted. In an example, when flexibly-connected segments are farther apart from each other, then the display becomes more flexible, less rigid, more bendable, and/or more rollable, but when flexibly-connected segments are closer together, then the display becomes less flexible, more rigid, less bendable, and/or less rollable.

In an example, a (bottom) layer of a second display can comprise a plurality of connected "tongue-and-groove" segments which interlocking protrusions and recesses which fit into each other when they are pulled tightly together. In an example, a second display can comprise a plurality of adjustable-connected segments (e.g. tongue-and-groove segments) so that it can be rolled, coiled, and/or wound around a roller (e.g. roller, spool, cylinder, rod, or pin). In an example, narrow rigid connected sections can have "tongue-and-grove" shapes, wherein a protrusion on an end of section fits into a recess on an end of a neighboring section when the sections are pulled close together.

In an flexibly-connected segments can be connected to each other by filaments, wires, cables, chains, springs, strings, and/or threads. In an example, these segments can be connected by filaments, wires, and/or strings, wherein increasing the tension (and/or decreasing the length) of the filaments, wires, and/or strings pulls the segments closer together and decreasing the tension (and/or increasing the length) of the filaments, wires, and/or strings moves the segments farther apart.

In an example, spacing between the segments can be adjusted by adjusting the tension of the filaments, wires, cables, chains, springs, strings, and/or threads. In an example, the degree to which sections are loosely or tightly connected to each other can be adjusting the tension of one or more filaments, wires, or strings which connect the sections to each other. In an example, the flexibility of a display which comprises a plurality of flexibly-connected segments can be adjusted by adjusting the tension of filaments, wires, cables, chains, springs, strings, and/or threads which connect the flexibly-connected segments. When these segments are pulled (or pushed) farther apart, they detach from each other and the display becomes more flexible.

In an example, the tension of longitudinal elements which connect the segments can be decreased so that a second display becomes more flexible in order to be rolled, coiled, and/or wound around a roller (e.g. roller, spool, cylinder, rod, or pin). In an example, the tension of longitudinal elements which connect the segments can be increased relaxed so that a second display becomes more rigid in order to display a flat image and serve as a touch screen. In this manner, a second display be flexible for changing configuration (including possibly changing curvature), but can be made into a relatively flat, rigid surface for use as a flat, rigid touch screen in its expanded configuration.

In an example, a second display can comprise a plurality of parallel flexibly-connected segments. In an example, a second display can comprise a plurality of parallel flexibly-connected segments which are connected by hinges and/or moveable joints. In an example, a second display can comprise a plurality of chain-linked segments. In an example, a second display can comprise a plurality of flexibly-connected segments with rectangular cross-sectional shapes. In an example, a second display can comprise a plurality of flexibly-connected segments with trapezoidal cross-sectional shapes. In an example, a second display can comprise a plurality of flexibly-connected segments with keystone-shaped cross-sections.

In an example, an expandable flexible display can comprise a plurality of flexibly-connected segments with varying widths. In an example, an expandable flexible display can comprise a plurality of flexibly-connected segments, wherein segments which are closer to the end (or side) of the display which is attached to a roller have a first average width, wherein segments which are farther from the end (or side) of the display which is attached to a roller have a second average width, and wherein the second average width is greater than the first average width. In an example, an expandable flexible display can comprise a plurality of flexibly-connected segments, wherein segments which are closer to the end (or side) of the display which is attached to a roller have a first average width, wherein segments which are farther from the end (or side) of the display which is attached to a roller have a second average width, and wherein the second average width is less than the first average width.

There are advantages and disadvantages to a having a wearable display be flexible. Advantages of having a wearable display be flexible include: being able to change the shape of the display so that it can be more easily moved from one location on the device to another location on the wearable device; and being able to roll or unroll the display. Disadvantages of having a wearable be flexible include: distortion of images on an uneven (e.g. uneven, wavy, non-flat) surface; and lack of uniform resistance for use of the display as a touch screen.

Having a display whose degree of flexibility can be selectively adjusted can provide the advantages of having a wearable display be flexible without the disadvantages thereof. In an example, a second display can be made (temporarily) flexible at a first time so that its shape can be changed, so that it can be moved from one location on a device to another location on the device, and/or so that it can be expanded. In an example, the flexibility of a second display can be adjusted so that it can be made more flexible (to transition from one shape to another). In an example, a second display can be made (temporarily) rigid at a second time so that its shape is fixed, so that it stays flat, and/or so that it can be used as a touch screen. In an example, a second display can be made less flexible (so that it can be stabilized in a selected shape for use as a touch screen).

In order to provide the advantages of having a wearable display be flexible without the disadvantages thereof, a wearable device can have a display whose flexibility can be changed (e.g. adjusted). In an example, the flexibility of a second display can be adjusted so that the display can be made more flexible (so that its shape can be changed) or can made be less flexible (so that it can serve as a touch screen). In an example, the flexibility of a second display can be adjusted so that it can be made more flexible (to transition from one shape to another) or can be made less flexible (so that it can be stabilized in a selected shape for use as a touch screen). In an example, a second display can comprise a plurality of adjustably-connected segments with interdigitated protrusions and recesses so that the flexibility of the second display can be adjusted. In an example, a second display can comprise a plurality of adjustably-connected tongue-and-groove segments with interdigitated protrusions and recesses so that the flexibility of the second display can be adjusted.

In an example, a second display can comprise a plurality of adjustable-connected segments (e.g. tongue-and-groove segments) which enable the bendability of the second display to be adjusted. In an example, a second display can comprise a plurality of adjustable-connected segments (e.g. tongue-and-groove segments) with interdigitated protrusions and recesses so that the bendability of the second display can be adjusted. In an example, a second display can comprise a plurality of adjustably-connected segments with interdigitated protrusions and recesses so that the flexibility of the second display can be adjusted.

In an example, a second display can comprise a plurality of adjustably-connected tongue-and-groove segments with interdigitated protrusions and recesses so that the flexibility of the second display can be adjusted. In an example, a second display can comprise a plurality of adjustable-connected segments (e.g. tongue-and-groove segments) which enable the bendability of the second display to be adjusted. In an example, a second display can comprise a plurality of adjustable-connected segments (e.g. tongue-and-groove segments) with interdigitated protrusions and recesses so that the bendability of the second display can be adjusted.

In an example, the bendability of a second display can be adjusted so that it becomes more bendable (so that its shape can be changed) or less bendable (so that it can serve as a touch screen). In an example, the bendability of a second display can be adjusted so that it becomes more bendable (to transition from one shape to another) or less bendable (so that it can be stabilized in a selected shape). In an example, the flexibility of a second display can be adjusted so that it can be made more flexible (to transition from an unexpanded size to an expanded size) and can be made less flexible (so that it can be stabilized in an expanded size for use as a touch screen).

In an example, a second display can made with an electroactive polymer. In an example, the flexibility of the second display can be adjusted by application of electrical (and/or electromagnetic) energy to the polymer. In an example, a second display can comprise a layer made with an electroactive polymer so that the flexibility of the second display can be adjusted by application of electrical (and/or electromagnetic) energy to the polymer. In an example, this layer can become more flexible when electrical energy is applied to it. In an example, this layer can become more rigid when electrical energy is applied to it. In an example, a second display can have a layer which is made with shape memory material. In an example, applying electrical energy to the shape memory material can make the second display more flexible. In an example, applying electrical energy to the shape memory material can make the second display more rigid.

In an example, a (layer of a) second display can be made with an ionic electroactive polymer, wherein applying electric energy and/or an electromagnetic field to the ionic electroactive polymer changes the flexibility and/or shape of the second display. In an example, a (layer of a) second display can be made with an ionic polymer-metal composite (IPMC), wherein applying electric energy and/or an electromagnetic field to the ionic polymer-metal composite (IPMC) changes the flexibility and/or shape of the second display. In an example, a (layer of a) second display can be made with polyvinylidene fluoride (PVDF), wherein applying electric energy and/or an electromagnetic field to the polyvinylidene fluoride (PVDF) changes the flexibility and/or shape of the second display.

In an example, the flexibility of the second display can be adjusted by application of electrical (and/or electromagnetic) energy to the polymer. In an example, a second display can comprise a layer made with an electroactive polymer so that the flexibility of the second display can be adjusted by application of electrical (and/or electromagnetic) energy to the polymer. In an example, this layer can become more flexible when electrical energy is applied to it. In an example, this layer can become more rigid when electrical energy is applied to it. In an example, a second display can have a layer which is made with shape memory material. In an example, applying electrical energy to the shape memory material can make the second display more flexible. In an example, applying electrical energy to the shape memory material can make the second display more rigid.

In an example, a second display can comprise at least four layers. A (top) first layer can be a flexible protective layer. A second layer can comprise an array and/or matrix of light-emitters. A third layer can comprise a plurality of electroconductive pathways which provide power to the light-emitters. A (bottom) fourth layer can comprise a plurality of flexibly-connected segments, wherein changing the spacing between the segments changes the overall flexibility and/or rigidity of the second display. The fourth layer can be made less rigid, more flexible, and more arcuate to facilitate changing the configuration of the second display, but can also be made more rigid, less flexible, and more flat to facilitate use of the second display as a touch screen.

In an example, a first layer of a second display can be a flexible but scratch-resistant polymer layer of a second display. In an example, this layer of a second display can be made with acrylonitrile butadiene styrene or high-density polyethylene. In an example, a second layer of a second display can comprise an array of light-emitting elements selected from the group consisting of: Light Emitting Diode (LED), Direct-Lit LED, Edge-Lit LED (ELED), Encapsulated LED, Micro-LED, Mini-LED, Monochromatic LED (MLED), Organic Light Emitting Diode (OLED), Quantum Dot LED (QLED), Resonant Cavity Light Emitting Diode (RCLED), Super-Luminescent Light Emitting Diode (SLED), and Tunable LED. In an example, a third layer of a second display can comprise flexible electroconductive pathways and/or circuits. In an example, these pathways and/or circuits can be made with a flexible polymer which has been doped and/or impregnated with electroconductive material.

In an example, a (bottom) fourth layer of a second display can comprise material whose rigidity, flexibility, and/or shape is affected by the application of electrical energy. In an example, a fourth layer can become more rigid, less flexible, and/or more flat when electrical energy is applied to it. Alternative, a fourth layer can become less rigid, more flexible, and/or more arcuate when electrical energy is applied to it. In an example, a fourth layer can be made from an electroactive polymer (EAP). In an example, a fourth layer can be made from shape-memory material.

In an example, a fourth layer can comprise a plurality of flexibly-connected segments. In an example, changing the spacing between segments in the fourth layer changes the overall flexibility and/or rigidity of the second display. The fourth layer can be made less rigid, more flexible, and more arcuate to facilitate changing the configuration of the second display, but can also be made more rigid, less flexible, and more flat to facilitate use of the second display as a touch screen.

In an example, a fourth layer of a second display can comprise a plurality of connected "tongue-and-groove" segments which interlocking protrusions and recesses which fit into each other when they are pulled tightly together. In an example, the "tongue-and-groove" segments can be connected by filaments, wires, or strings. When the tension of the filaments, wires, or strings is decreased, then the fourth layer (and the whole second display) becomes less rigid, more flexible, and more arcuate. When the tension of the filaments, wires, or strings is increased, then the fourth layer (and the whole second display) becomes more rigid, less flexible, and more flat.

In an example, a display can comprise at least three layers. A (top) first layer can be a flexible protective layer. A second layer can comprise an array and/or matrix of light-emitters and electroconductive pathways which provide power to the light-emitters. A third layer can comprise a plurality of flexibly-connected segments, wherein changing the spacing between the segments changes the overall flexibility and/or rigidity of the display. The third layer can be made less rigid, more flexible, and more arcuate to facilitate changing the configuration of the display, but can also be made more rigid, less flexible, and more flat to facilitate use of the display as a touch screen.

In an example, a layer of a second display can comprise material whose rigidity, flexibility, and/or shape is affected by the application of electrical energy. In an example, this layer can become more rigid, less flexible, and/or more flat when electrical energy is applied to it. In an alternative example, this layer can become less rigid, more flexible, and/or more arcuate when electrical energy is applied to it. In an example, a layer can be made from an electroactive polymer (EAP). In an example, a layer can be made from shape-memory material.

In an example, one layer of a second display can comprise a thin film layer. In an example, one layer of a second display can comprise a thin film transistor (TFT) layer. In an example, a second display can comprise a thin film transistor (TFT) array. In an example, a second display can comprise a thin film transistor (TFT) array to which light emitters are electrically connected. In an example, a TFT array can be made with silicon. In an example, one layer of a second display can comprise a flexible printed circuit board.

In an example, an expandable display can comprise a plurality of scissor-motion articulated elements which are inter-connected by movable joints. In an example, an expandable display can comprise a plurality of zigzag-shaped articulated elements which are inter-connected by movable joints.

In an example, a second display can comprise a plurality of sliding and/or telescoping sections. In an example, one or more sections can slide out from under one or more other sections to change a display from its first (unexpanded) configuration to its second (expanded) configuration. In an example, two or more display sections can be rigid and separate from each other, wherein the second display is expanded by sliding one rigid section out from underneath the other rigid section. In an example, a second display can comprise a plurality of sections, wherein the sections are not coplanar in a first (unexpanded) configuration and are coplanar in a second (expanded) configuration.

In an example, at least 75% of the surface areas of the second and third sections are not hidden under the first section in a second (expanded) configuration, wherein the second section is moved in a first direction from the first configuration to the second configuration, wherein the third section is moved in a second direction from the first configuration to the second configuration, and wherein the second direction is opposite the first direction. In an example, in a second (expanded) configuration, the sections of a second display can be coplanar. In an example, two display sections can be non-coplanar and overlapping in a first configuration and can be coplanar and non-overlapping in a second configuration.

In an example, a second display can comprise a plurality of telescoping sections, wherein the telescoping sections overlap to a first extent in a first (unexpanded) configuration, overlap to a second extent in a second (expanded) configuration, and wherein the second extent is less than the first extent. In an example, in a first (unexpanded) configuration, the sections of a second display can be substantially parallel to each other and non-coplanar. In an example, a second display can be comprise three sections which overlap each other to a first extent in a first (unexpanded) configuration and overlap each other to a second extend in a second (expanded) configuration, wherein the second extent is less than the first extent.

In an example, a second display can be comprise three sections, wherein a first section is on top of second and third sections in a first (unexpanded) configuration and wherein the second and third section slide out from under the first section in a second (expanded) configuration. In an example, one display section can be slid outward from underneath another display section. In an example, a second display can be expanded (e.g. expanded, extended, lengthened, and/or widened) by reducing the degree of overlap between two or more display sections which together comprise the second display.

In an example, a second display can comprise a plurality of movable sections connected by hinges and/or moveable joints, wherein the sections have a first configuration in which the sections are parallel (but not coplanar) to each other and a second configuration in which the sections are coplanar. In an example, a second display can be comprise three sections, wherein the majority of the surface areas of second and third sections are underneath a first section in a first (unexpanded) configuration and wherein the majority of the surface areas of the second and third sections are not underneath the first section in a second (expanded) configuration. In an example, a second display can comprise a plurality of movable sections which can be moved from a first configuration in which the sections are parallel (but not coplanar) to each other to a second configuration in which the sections are coplanar.

In an example, a second display can have a plurality of axes and be expanded (from its first configuration to its second configuration) in the direction of just one of its axes. In an example, a second display can have a plurality of axes and be expanded only in a direction which is parallel to its shortest axis. In an example, a second display can have a plurality of axes and be expanded only in the direction which is parallel to its longest axis. In an example, a second display can be expanded (from its first configuration to its second configuration) in a direction which is orthogonal to the plane of the circumference of the device and/or the person's wrist. In an example, a second display can be expanded (from its first configuration to its second configuration) in a direction which is parallel to the plane of the circumference of the device. In an example, a second display can be expanded (from its first configuration to its second configuration) in a direction which is parallel to the plane of the circumference of the device and tangential to the circumference of the device.

In an example, a second display can be expanded in one direction. If this device were to be worn on a person's left wrist and/or lower arm, then the direction of expansion of the second display can be: away from the plane of the circumference of the device, toward the person's elbow, and onto the dorsal surface of the person's lower arm. In an example, the direction of expansion of the second display can be in the opposite direction: away from the plane of the circumference of the device, away from the person's elbow, and onto the back of the person's hand.

In an example, a second display can be expanded in two directions. In an example, a second display can be expanded in two opposite directions. In an example, a second display can be expanded in a first direction (from a person's wrist toward their elbow) and also expanded in a second opposite direction (from the person's wrist toward their fingers). In an example, a second display can be expanded in two directions which are both orthogonal to the plane of the circumference of the device. In an example, a second display can be expanded in two opposite directions which are both orthogonal to the plane of the circumference of the device.

In an example, a second display can be expanded in two directions which are both parallel to the plane of the circumference of the device. In an example, a second display can be expanded in two opposite directions which are both parallel to the plane of the circumference of the device. In an example, a second display can be expanded in two directions which are both orthogonal to the plane of the circumference of the device. In an example, a second display can be expanded in two opposite directions which are both orthogonal to the plane of the circumference of the device.

In an example, a second display could be expanded in two opposite directions: (1) expansion away from the plane of the circumference of the device, toward the person's elbow, and onto the dorsal surface of the person's lower arm; and also (2) expansion away from the plane of the circumference of the device, away from the person's elbow, and onto the back of the person's hand.

In an example, a device with a flexible display can further comprise an inertial motion sensor. In an example, a device with a flexible display can further comprise an accelerometer and a gyroscope. In an example, a device with a flexible display can further comprise a strain, stretch, and/or angle sensor. In an example, a device with a flexible display can further comprise a light sensor. In an example, a device with a flexible display can further comprise a visible light sensor. In an example, a device with a flexible display can further comprise an infrared light sensor. In an example, a device with a flexible display can further comprise a pressure sensor. In an example, a device with a flexible display can further comprise a capacitive sensor.

In an example, an expandable display device can be an accessory to a conventional smart watch (or other wrist-worn device). In an example, an expandable display device can be a modular attachment to a conventional smart watch. In an example, the invention is embodied in a separate device with an expandable display which is removably-attached to a conventional smart watch which already has a display. This provides an expandable second display for a conventional smart watch, without having to entirely replace the conventional smart watch. In an example, an attachment mechanism can attach a housing to the band of a conventional smart watch.

In an example, an expandable display device which is removably-attached to an existing smart watch (or other wrist-worn technology) can comprise: an expandable display; a housing; and an attachment mechanism; wherein the expandable display is retracted into the housing in a first (unexpanded) configuration and is extended out from the housing in a second (expanded) configuration, wherein the attachment mechanism removably-attaches the housing to a smart watch (or other wrist-worn technology) which has a non-expandable display.

In an example an attachment mechanism can be a band which encircles some or all of a person's wrist. In an example, the plane of the circumference of this band can be substantially parallel to the plane of the circumference of the band of the smart watch. In an, an attachment mechanism can be a band which encircles a person's wrist, wherein the band has two openings through which the band of the smart watch is inserted, pulled, and/or threaded. In an example, an attachment mechanism which attaches a housing to a conventional smart watch can be selected from the group consisting of: buckle, clamp, clasp, clip, hook, hook and loop fabric, magnet, pin, plug, and strap.

In an example, this device can be a modular attachment which is attached to the band of a conventional smart watch by an attachment mechanism selected from the group consisting of: buckle, clamp, clasp, clip, hook, hook and loop fabric, magnet, opening through which smart watch band is inserted, pin, plug, and strap. In an example, there can be two or more openings in an attachment mechanism through which the band of a conventional smart watch is inserted, pulled, and/or threaded, thereby attaching this device to the conventional smart watch.

In an example, this device can further comprise a battery, a data processor, and a wireless data transmitter and/or receiver. In an example, this device can further comprise other components selected from the group consisting of: battery, data processor, electromagnetic actuator, infrared light sensor, laser, microphone, motion sensor, one or more buttons, speaker, spectroscopy sensor, visible light sensor, watch crown, wireless data receiver, and wireless data transmitter.

In an example, a wearable device with an expandable display can comprise: (a) a wearable device which is configured to be worn around at least three-quarters of the circumference of a person's wrist and/or lower arm, wherein a dorsal portion of the device is configured to be worn on a dorsal quarter of the circumference of the person's wrist, wherein a ventral portion of the device is configured to be worn on at least part of the ventral quarter of the circumference of the person's wrist, wherein a first lateral portion of the device is configured to be worn on a first lateral quarter of the circumference of the person's wrist between the dorsal quarter and the ventral quarter, wherein a second lateral portion of the device is configured to be worn on a second lateral quarter of the circumference of the person's wrist between the dorsal quarter and the ventral quarter, wherein the second lateral quarter is opposite the first lateral quarter; (b) a first light-emitting display on the wearable device, wherein the portion of the device on which the greatest percentage of the first light-emitting display is located is the dorsal portion; and (c) a second light-emitting display on the wearable device, wherein the second light-emitting display has a first configuration in which the portion of the device on which the greatest percentage of the second light-emitting display is located is the first lateral portion or the second lateral portion and the second light-emitting display is a first size, and wherein the second light-emitting display has a second configuration in which the portion of the device on which the greatest percentage of the second light-emitting display is located is the dorsal portion and the second light-emitting display is a second size, and wherein the second size is greater than the first size.

In an example, the second light-emitting display can be flipped, pivoted, and/or rotated from being primarily on a lateral portion of the device to being primarily on a dorsal portion of the device when the second light-emitting display is changed from the first configuration to the second configuration. In an example, an image-displaying surface of the second light-emitting display can face inward toward the person's wrist in the first configuration and face outward away from the person's wrist in the second configuration.

In another example, the second light-emitting display can be slid and/or shifted along the circumference of the device from being primarily on a lateral portion of the device to being primarily on a dorsal portion of the device when the second light-emitting display is changed from the first configuration to the second configuration. In an example, the second light-emitting display can have a longitudinal axis which is parallel to the plane of the circumference of the device in the first configuration and have a longitudinal axis which is orthogonal to the plane of the circumference of the device in the second configuration.

In an example, a device can further comprise a roller, wherein the second light-emitting display is unrolled from the roller when the second light-emitting display is changed from the first configuration to the second configuration. In an example, the roller can have teeth, notches, gears, and/or protrusions which engage the second light-emitting display. In another example, the second light-emitting display can be looped around a roller, wherein looping means that the display curves and/or bends partially around the circumference of a roller, but not around the entire circumference of the roller. In an example, the second light-emitting display can be looped around two or more rollers, wherein looping means that the display curves and/or bends partially around the circumference of a roller, but not around the entire circumference of the roller.

In an example, the second light-emitting display can further comprise a plurality of flexibly-connected segments. In an example, the plurality of flexibly-connected segments can have interdigitated protrusions and recesses. In an example, the second light-emitting display can become more flexible when the flexibly-connected sections are more-loosely and/or less-closely connected to each other and the second display becomes more rigid when the flexibly-connected sections are more-tightly and/or more-closely connected to each other. In an example, the flexibly-connected segments can be connected to each other by filaments, wires, cables, chains, springs, strings, and/or threads. In an example, changing the tensions and/or lengths of the filaments, wires, cables, chains, springs, strings, and/or threads can change the spacing between the flexibly-connected segments which changes the flexibility and/or rigidity of the second light-emitting display.

In an example, the second light-emitting display can be made with an electroactive polymer. In an example, applying electrical energy and/or electromagnetic energy to the electroactive polymer can change the flexibility and/or rigidity of the second light-emitting display.

In an example, an expandable display device which is removably-attached as an accessory to a wrist-worn device can comprise: an expandable display; a housing; and an attachment mechanism, wherein the expandable display is retracted into the housing in a first configuration and is extended out from the housing in a second configuration, and wherein the attachment mechanism removably-attaches the housing to a wrist-worn device which has a non-expandable display. In an example, the attachment mechanism can be a band which is configured to encircle a person's wrist. In an example, the attachment mechanism can be selected from the group consisting of: buckle, clamp, clasp, clip, hook, hook and loop fabric, magnet, pin, plug, and strap. In an example, the attachment mechanism can comprise one or more openings on the device through which part of the wrist-worn device is inserted. Relevant device variations discussed in this introductory section can be applied to the example shown in FIGS. 2 through 45 which follow.

FIG. 1 shows an oblique side view of a generic (e.g. prior art) smart watch in order to illustrate the locations of the dorsal, ventral, lateral quarters around the circumference of the watch when the watch housing is worn on the dorsal side of a person's wrist. This figure also shows the locations of four portions of the device relative to these four quarters of the circumference of a wrist. For example, in this figure the watch housing is primarily located on the dorsal portion of the device (over the dorsal quarter of the wrist). These four portions serve as a locational framework which will be used in examples of the invention in subsequent figures in order to more-clearly specify the locations of device components.

Figure 2:
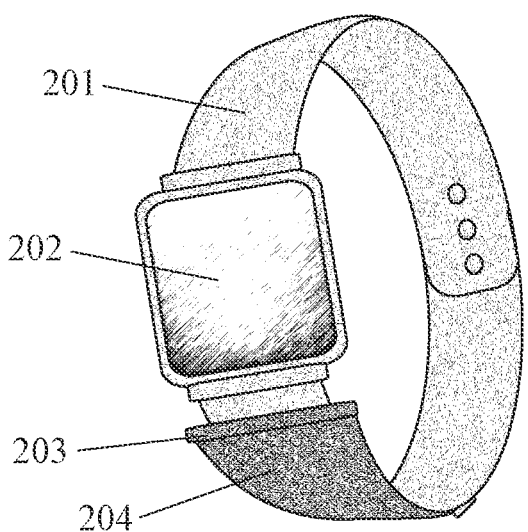
FIGS. 2 through 4 show three sequential views of a wearable device with a display which flips onto the dorsal portion of the device and is then expanded.
Figure 3:
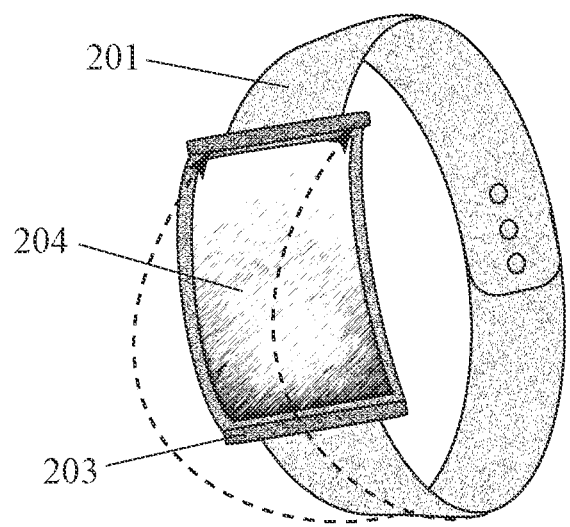
Figure 4:
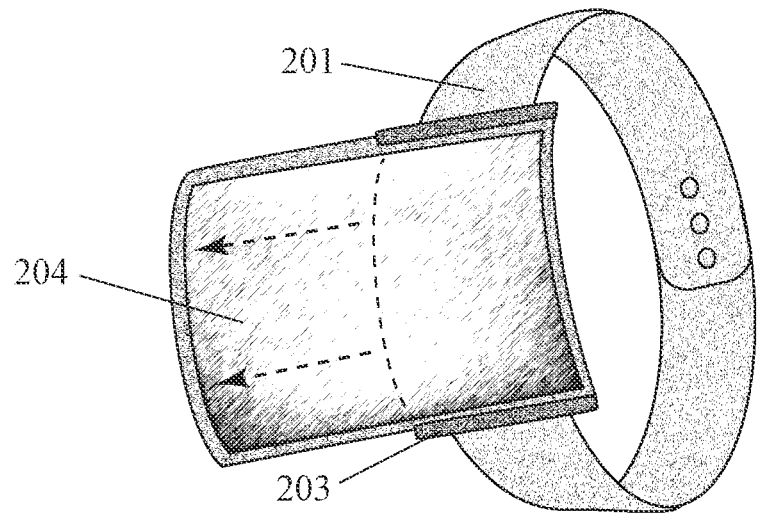

FIGS. 2 through 4 show an example of how this invention can be embodied in a wearable device with an expandable display. FIGS. 2 through 4 show three oblique side views, at three different times, of an example of a wearable device with an expandable display comprising: (a) a wearable device which is configured to be worn around at least three-quarters of the circumference of a person's wrist and/or lower arm, wherein a dorsal portion of the device is configured to be worn on a dorsal quarter of the circumference of the person's wrist and/or lower arm, wherein a ventral portion of the device is configured to be worn on at least part of the ventral quarter of the circumference of the person's wrist and/or lower arm, wherein a first lateral portion of the device is configured to be worn on a first lateral quarter of the circumference of the person's wrist and/or lower arm between the dorsal quarter and the ventral quarter, wherein a second lateral portion of the device is configured to be worn on a second lateral quarter of the circumference of the person's wrist and/or lower arm between the dorsal quarter and the ventral quarter, wherein the second lateral quarter is opposite the first lateral quarter; (b) a first light-emitting display on the wearable device, wherein the portion of the device on which the greatest percentage of the first light-emitting display is located is the dorsal portion; and (c) a second light-emitting display on the wearable device, wherein the second light-emitting display has a first configuration in which the portion of the device on which the greatest percentage of the second light-emitting display is located is the first lateral portion or the second lateral portion and the second light-emitting display is a first size, and wherein the second light-emitting display has a second configuration in which the portion of the device on which the greatest percentage of the second light-emitting display is located is the dorsal portion and the second light-emitting display is a second size, and wherein the second size is greater than the first size.

With respect to specific components, FIGS. 2 through 4 show three oblique side views, at three different times, of a wearable device with an expandable display comprising: (a) a wearable device 201 which is configured to be worn around at least three-quarters of the circumference of a person's wrist and/or lower arm, wherein a dorsal portion of the device is configured to be worn on a dorsal quarter of the circumference of the person's wrist and/or lower arm, wherein a ventral portion of the device is configured to be worn on at least part of the ventral quarter of the circumference of the person's wrist and/or lower arm, wherein a first lateral portion of the device is configured to be worn on a first lateral quarter of the circumference of the person's wrist and/or lower arm between the dorsal quarter and the ventral quarter, wherein a second lateral portion of the device is configured to be worn on a second lateral quarter of the circumference of the person's wrist and/or lower arm between the dorsal quarter and the ventral quarter, wherein the second lateral quarter is opposite the first lateral quarter; (b) a first light-emitting display 202 on the wearable device, wherein the portion of the device on which the greatest percentage of the first light-emitting display is located is the dorsal portion; and (c) a second light-emitting display 204 on the wearable device, wherein the second light-emitting display has a first configuration in which the portion of the device on which the greatest percentage of the second light-emitting display is located is the first lateral portion or the second lateral portion and the second light-emitting display is a first size, and wherein the second light-emitting display has a second configuration in which the portion of the device on which the greatest percentage of the second light-emitting display is located is the dorsal portion and the second light-emitting display is a second size, and wherein the second size is greater than the first size. This example also includes a hinge and/or movable joint 203 around which the second display is flipped, pivoted, and/or rotated from the first configuration to the second configuration.

FIGS. 2 through 4 show this device at three different times. FIG. 2 shows this device at a first time when the second display is in its first configuration. At this first time, the second display is unexpanded and is located on a lateral portion of the device. FIG. 3 shows this device at a second time. At this second time, the second display has been flipped, pivoted, and/or rotated around the hinge and/or joint, but is not yet expanded. FIG. 4 shows this device at a third time when the device is in its second configuration. At this third time, the second display has been flipped, pivoted, and/or rotated around the hinge and/or joint and has also been expanded.

In this example, a wearable device with an expandable display is embodied in the form of a smart watch. In various examples, a wearable device with an expandable display can be embodied in a form selected from the group consisting of: smart watch, fitness band, wristband, sleeve or cuff, bracelet or bangle, arm band, glucose monitor, identification band, and wearable phone. In this example, a first display is located on the dorsal portion of the device and the second display flips, pivots, and/or rotates from a lateral portion of the device to the dorsal portion of the device. In an alternative example, a first display can be located on the ventral portion of the device and the second display can flip, pivot, and/or rotate from a lateral portion of the device to the ventral portion of the device.

In an example, a first display can display an image (e.g. text, picture, or other visual content). In an example, a first display can comprise a plurality (e.g. an array or matrix) of light-emitting elements which collectively display an image (e.g. text, picture, or other visual content). In an example, a first display can display a digital image. In an example, a first display can be a computer display and/or screen. In an example, a first display can be a holographic display. In an example, a first display can be a touch screen (e.g. a touch and/or gesture responsive display). In an example, a first display can comprise light-sensing elements as well as light-emitting elements.

In an example, a first display can display an image (e.g. text, picture, or other visual content) via a plurality (e.g. an array or matrix) of light-emitting elements. In an example, light-emitting elements in a plurality of light-emitting elements can be selected from the group consisting of: Light Emitting Diode (LED), Direct-Lit LED, Edge-Lit LED (ELED), Encapsulated LED, Micro-LED, Mini-LED, Monochromatic LED (MLED), Organic Light Emitting Diode (OLED), Quantum Dot LED (QLED), Resonant Cavity Light Emitting Diode (RCLED), Super-Luminescent Light Emitting Diode (SLED), and Tunable LED.

In an example, a first display can be rigid and flat, like a display on a traditional smart watch. In an example, a first display can be non-expandable, non-flexible, non-bendable, and non-rollable. In an example, a first display can have a static size. Its size does not change over time. In an example, a first display can have a static location. It does not move relative to the rest of the device. In an example, a first display can have a shape which is selected from the group consisting of: polygonal, square, square with rounded vertexes, rectangle, rectangle with rounded vertexes, hexagonal, convex, and circular. In an example, a first display can serve as the primary display for a device when a second display is in a first configuration. In an example, a first display can be covered by a second display when the second display is in the second configuration.

In an example, a first display can be on the dorsal portion of a device and over dorsal quarter of the circumference of a person's wrist and/or lower arm. This corresponds to the way in which most people wear a smart watch, with the watch housing worn on the dorsal side of their wrist. In an example, a first display can be entirely within a dorsal portion of a device. In an example, a first display can be entirely on the dorsal quarter of the circumference of a person's wrist and/or lower arm.

In an example, a first display can be larger than the dorsal portion of a device, but still be centered on the dorsal portion. In an example, the portion of a device (among the four portions dorsal, ventral, first lateral, and second lateral) on which the greatest percentage of a first light-emitting display is located can be the dorsal portion. In an example, a first display can be centered on the center of the dorsal portion. In an example, a first display can be located entirely on the dorsal portion of the device. In an example, a first display can be so large that it covers more than just the dorsal quarter of a device. In an example, at least 75% of a first display can be on the dorsal portion of the device.

In an example, a device can include a second display in addition to a first display. In an example, a second display can be flexible, bendable, and/or rollable. In an example, a second display can be flexible, bendable, and/or rollable so that it can transition between unexpanded and expanded configurations without the display being damaged. In an example, a second display can be flexible so that it can change between being flat (e.g. planar) and arcuate (e.g. curved) without the display being damaged. In an example, a second display can be flexible so that it can change between flat, concave, and convex shapes. In an example, a second display can be flexible so that it can change between flat, concave, or convex configurations.

In an example, a second display can be manually moved from its first configuration to its second configuration. In an example, a second display can be manually flipped, pulled, pushed, pressed, and/or slid from, its first configuration to its second configuration by the person wearing the device. Alternatively, a second display can be automatically moved from its first configuration to its second configuration by one or more actuators. Alternatively, a second display can be automatically moved from its first configuration to its second configuration by one or more electromagnetic actuators. In an example, a second display can be selectively and reversibly locked into its first configuration or its second configuration by the person wearing the device.

There are advantages and disadvantages to a having a wearable display be flexible. Advantages of having a wearable display be flexible include: being able to change the shape of the display as it is moved from one location to another on a wearable device; and being able to expand the display by unrolling, unfolding, and/or unbending the display. Disadvantages of having a wearable be flexible include: distortion of images on an uneven (e.g. non-flat) surface; and lack of uniform resistance for use of the display as a touch screen.

In order to provide the advantages of having a wearable display be flexible without the disadvantages thereof, a wearable device can have a display whose flexibility can be changed (e.g. adjusted). In an example, the flexibility of a second display can be adjusted so that the display can be made more flexible (so that its shape can be changed) or can made be less flexible (so that it can serve as a touch screen). In an example, the flexibility of a second display can be adjusted so that it can be made more flexible (to transition from one shape to another) or can be made less flexible (so that it can be stabilized in a selected shape for use as a touch screen). In an example, the flexibility of a second display can be adjusted so that it can be made more flexible (to transition from an unexpanded size to an expanded size) and can be made less flexible (so that it can be stabilized in an expanded size for use as a touch screen).

In an example, a second display can comprise a plurality of flexibly-connected segments. When the segments are sufficiently small relative to the overall display, the overall display can be relatively flexible, bendable, and rollable. In an example, a display can comprise between 20 and 60 flexibly-connected segments. In an example, a display can comprise between 50 and 100 flexibly-connected segments. In an example, a second display can comprise a plurality of rectangular segments which are flexibly connected along their longitudinal (longer) sides. In an example, a second display can comprise a plurality of parallel rectangular segments which are flexibly connected along their longitudinal (longer) sides. In an example, a second display can comprise a plurality of flexibly-connected hexagonal segments.

In an example, the spacing between flexibly-connected segments comprising a display can be changed (e.g. adjusted) in order to change (e.g. adjust) the flexibility and/or rigidity of the display. In an example, a second display can comprise a plurality of adjustably-connected segments so that the flexibility of the second display can be adjusted. In an example, a second display can have a layer of adjustably-connected segments so that the flexibility of the second display can be adjusted. In an example, when flexibly-connected segments are farther apart from each other, then the display becomes more flexible, less rigid, more bendable, and/or more rollable, but when flexibly-connected segments are closer together, then the display becomes less flexible, more rigid, less bendable, and/or less rollable.

In an flexibly-connected segments can be connected to each other by filaments, wires, cables, chains, springs, strings, and/or threads. In an example, spacing between the segments can be adjusted by adjusting the tension of the filaments, wires, cables, chains, springs, strings, and/or threads. In an example, the flexibility of a display which comprises a plurality of flexibly-connected segments can be adjusted by adjusting the tension of filaments, wires, cables, chains, springs, strings, and/or threads which connect the flexibly-connected segments.

In an example, a second display can comprise a plurality of adjustably-connected segments with interdigitated protrusions and recesses so that the flexibility of the second display can be adjusted. In an example, a second display can comprise a plurality of adjustably-connected tongue-and-groove segments with interdigitated protrusions and recesses so that the flexibility of the second display can be adjusted.

In an example, a second display can comprise a plurality of rectangular adjustably-connected tongue-and-groove segments with interdigitated protrusions and recesses so that the flexibility of the second display can be adjusted.

In an example, segments in a plurality of adjustably-connected segments can be shaped like tongue-and-groove floor boards, wherein a protrusion on a side of a first segment fits into a recess on a side of an adjacent second segment when the two segments are pushed (or pulled) close together. Unlike floor boards which are pushed together (e.g. by the lateral force of a hammer) into a permanently-interdigitated configuration, segments in a second display can be reversibly pulled (or pushed) closer together or father apart. When these segments are pulled (or pushed) closer together, they interlock and the display becomes more rigid. When these segments are pulled (or pushed) farther apart, they detach from each other and the display becomes more flexible. In an example, these segments can be connected by filaments, wires, and/or strings, wherein increasing the tension (and/or decreasing the length) of the filaments, wires, and/or strings pulls the segments closer together and decreasing the tension (and/or increasing the length) of the filaments, wires, and/or strings moves the segments farther apart.

In an example, a second display can made with an electroactive polymer. In an example, the flexibility of the second display can be adjusted by application of electrical (and/or electromagnetic) energy to the polymer. In an example, a second display can comprise a layer made with an electroactive polymer so that the flexibility of the second display can be adjusted by application of electrical (and/or electromagnetic) energy to the polymer. In an example, this layer can become more flexible when electrical energy is applied to it. Alternatively, this layer can become more rigid when electrical energy is applied to it. In an example, a second display can have a layer which is made with shape memory material. In an example, applying electrical energy to the shape memory material can make the display more flexible. Alternatively, applying electrical energy to the shape memory material can make the display more rigid.

In an example, a second display can be flexible. In an example, a second display can be bent and unbent without damage to the display. In an example, a second display can be bendable so that it can be folded or unfolded without damage to the display. In an example, a second display can be bendable so that it can be rolled or unrolled without damage to the display. In an example, the bendability of a second display can be adjusted so that it becomes more bendable (so that its shape can be changed) or less bendable (so that it can serve as a touch screen). In an example, the bendability of a second display can be adjusted so that it becomes more bendable (to transition from one shape to another) or less bendable (so that it can be stabilized in a selected shape).

In an example, a second display can comprise a plurality of adjustable-connected segments (e.g. tongue-and-groove segments) which enable the bendability of the second display to be adjusted. In an example, a second display can comprise a plurality of adjustable-connected segments (e.g. tongue-and-groove segments) with interdigitated protrusions and recesses so that the bendability of the second display can be adjusted. In an example, a second display can made with an electroactive polymer so that the bendability of the second display can be adjusted by application of electrical (and/or electromagnetic) energy.

In an example, a second display can be rollable. In an example, a second display can be rolled, coiled, and/or wound without damage to the display. In an example, a second display can be wound or unwound around a roller (e.g. roller, spool, cylinder, rod, or pin) without damage to the display. In an example, a second display can be rolled, coiled, and/or wound around a roller (e.g. roller, spool, cylinder, rod, or pin) (and also unrolled, uncoiled, and/or unwound from the roller (e.g. roller, spool, cylinder, rod, or pin) without damage to the display. In an example, a second display can be rolled, coiled, and/or wound (e.g. around a roller (e.g. roller, spool, cylinder, rod, or pin) into an unexpanded configuration and unrolled, uncoiled, and/or unwound (e.g. from the roller (e.g. roller, spool, cylinder, rod, or pin) into an expanded configuration.

In an example, a device can have a single roller mechanism comprising a roller (e.g. roller, spool, cylinder, rod, or pin) on one side of a flexible display. In an example, this side of the display can be rolled (e.g. rolled, coiled, and/or wound) around this roller or unrolled (e.g. unrolled, uncoiled, and/or unwound) from this roller. In an example, a device can have two roller mechanisms on opposite sides of a flexible display. In an example, each side of the display can be rolled (e.g. rolled, coiled, and/or wound) around one of the two rollers roller or unrolled (e.g. unrolled, uncoiled, and/or unwound) from that roller. In an example, rollers in two different roller mechanisms can rotate in opposite directions (e.g. one clockwise and one counter-clockwise) as a flexible display is expanded.

In an example, a second display can comprise a plurality of adjustable-connected segments (e.g. tongue-and-groove segments) so that it can be rolled, coiled, and/or wound around a roller (e.g. roller, spool, cylinder, rod, or pin). In an example, the tension of longitudinal elements which connect the segments can be decreased so that the second display becomes more flexible in order to be rolled, coiled, and/or wound around a roller (e.g. roller, spool, cylinder, rod, or pin). In an example, the tension of longitudinal elements which connect the segments can be increased relaxed so that the second display becomes more rigid in order to display a flat image and serve as a touch screen.

In an example, the (outward-facing) size of a second display can be reduced by rolling, coiling, and/or winding (e.g. one side of) the display around a roller (e.g. roller, spool, cylinder, rod, or pin). In an example, the (outward-facing) size of the second display can be increased by unrolling, uncoiling, and/or unwinding (e.g. one side of) the display from around the roller (e.g. roller, spool, cylinder, rod, or pin). In an example, the visible surface area of a second display can be reduced by rolling, coiling, and/or winding (e.g. one side of) the display around a roller (e.g. roller, spool, cylinder, rod, or pin). In an example, the visible surface area of the second display can be increased by unrolling, uncoiling, and/or unwinding (e.g. one side of) the display from around the roller (e.g. roller, spool, cylinder, rod, or pin).

In an example, the lower surface and/or the lateral sides of the second display can have protrusions or recesses (e.g. teeth, ridges, notches, or undulations) and a roller (e.g. roller, spool, cylinder, rod, or pin) around which the display is rolled, coiled, and/or wound can have recesses or protrusions (e.g. teeth, ridges, notches, or undulations) which are geometrically complementary to those of the display. In an example, the protrusions or recesses on the display can interdigitate (e.g. interdigitate, engage, and/or mesh) with the recesses or protrusions on the roller. In an example, a roller (e.g. roller, spool, cylinder, rod, or pin) can comprise a gear which engages protrusions or recesses (e.g. teeth, ridges, notches, or undulations) on the lower surface of a second display.

In an example, a second display can be rolled, coiled, and/or wound around a single roller (e.g. roller, spool, cylinder, rod, or pin). In an example, a second display can be rolled, coiled, and/or wound around two or more rollers (e.g. rollers, spools, cylinders, rods, or pins). In an example, the distance between the two rollers (e.g. rollers, spools, cylinders, rods, or pins) can be changed. In an example, the (outward-facing) size of a second display can be increased by decreasing the distance between the two rollers (e.g. rollers, spools, cylinders, rods, or pins) around which a second display is looped. In an example, a second display can be rolled, coiled, and/or wound around a first roller (e.g. roller, spool, cylinder, rod, or pin) and looped around (e.g. bent around part of the circumference of) a second roller (e.g. roller, spool, cylinder, rod, or pin).

In an example, a second display can display an image (e.g. text, picture, or other visual content). In an example, a second display can comprise a plurality (e.g. an array or matrix) of light-emitting elements which collectively display an image (e.g. text, picture, or other visual content). In an example, a second display can display a digital image. In an example, a second display can be a computer display and/or screen. In an example, a second display can be a holographic display. In an example, a second display can be a touch screen (e.g. a touch and/or gesture responsive display). In an example, a second display can comprise light-sensing elements as well as light-emitting elements.

In an example, a second display can display an image (e.g. text, picture, or other visual content) via a plurality (e.g. an array or matrix) of light-emitting elements. In an example, light-emitting elements in a plurality of light-emitting elements can be selected from the group consisting of: Light Emitting Diode (LED), Direct-Lit LED, Edge-Lit LED (ELED), Encapsulated LED, Micro-LED, Mini-LED, Monochromatic LED (MLED), Organic Light Emitting Diode (OLED), Light Emitting Diode Zep Elin (LED Zep Elin), Quantum Dot LED (QLED), Resonant Cavity Light Emitting Diode (RCLED), Super-Luminescent Light Emitting Diode (SLED), and Tunable LED.

In an example, a second display can be changed from its first configuration to its second configuration in two steps. In an example, a second display can be moved relative to the rest of a wrist-worn device in a first step and then it can be expanded in a second step. In an example, a second display can be changed from its first configuration to its second configuration by being moved relative to the rest of a wrist-worn device and then expanded. In an example, a second display can be changed from its first configuration to its second configuration by being moved from around the circumference (e.g. from one quarter portion to another) of a wrist-worn device and then expanded away from the plane of the circumference of the device. In an example, a second display can be changed from its first configuration to its second configuration by being moved from a location primarily along a lateral portion of a wrist-worn device to a location primarily along the dorsal portion of the wrist-worn device before the second display is expanded away from the plane of the circumference of the device.

In an example, a second display can be changed from its first configuration to its second configuration by being flipped (e.g. flipped, pivoted, folded, and/or rotated) from a location primarily along a lateral portion of a wrist-worn device to a location primarily along the dorsal portion of the wrist-worn device and then expanded away from the plane of the circumference of the device. In an example, a second display can be changed from its first configuration to its second configuration by being slid (e.g. slid or shifted along the circumference of the wrist-worn device) from a location primarily along a lateral portion of a wrist-worn device to a location primarily along the dorsal portion of the wrist-worn device and then expanded away from the plane of the circumference of the device.

In an example, a second display can be changed from its first configuration to its second configuration by being flipped (e.g. flipped, pivoted, folded, and/or rotated) from a location primarily along a lateral portion of a wrist-worn device to cover the first display and then expanded away from the plane of the circumference of the device. In an example, a second display can be changed from its first configuration to its second configuration by being slid (e.g. slid or shifted along the circumference of the wrist-worn device) from a location primarily along a lateral portion of a wrist-worn device to cover the first display and then expanded away from the plane of the circumference of the device.

Alternatively, a second display can be expanded first and then moved relative to the rest of a wrist-worn device. In an example, a second display can be changed from its first configuration to its second configuration by being expanded and then moved relative to the rest of a wrist-worn device. In an example, a second display can be changed from its first configuration to its second configuration by being expanded away from the plane of the circumference of the device and then moved from around the circumference (e.g. from one quarter portion to another) of a wrist-worn device. In an example, a second display can be changed from its first configuration to its second configuration by being expanded away from the plane of the circumference of the device and then moved from a location primarily along a lateral portion of a wrist-worn device to a location primarily along the dorsal portion of the wrist-worn device.

In an example, a second display can be changed from its first configuration to its second configuration by being expanded away from the plane of the circumference of the device and then flipped (e.g. flipped, pivoted, folded, and/or rotated) from a location primarily along a lateral portion of a wrist-worn device to a location primarily along the dorsal portion of the wrist-worn device. In an example, a second display can be changed from its first configuration to its second configuration by being expanded away from the plane of the circumference of the device and then slid (e.g. slid or shifted along the circumference of the wrist-worn device) from a location primarily along a lateral portion of a wrist-worn device to a location primarily along the dorsal portion of the wrist-worn device.

In an example, a second display can be changed from its first configuration to its second configuration by being expanded away from the plane of the circumference of the device and the flipped (e.g. flipped, pivoted, folded, and/or rotated) from a location primarily along a lateral portion of a wrist-worn device to cover the first display. In an example, a second display can be changed from its first configuration to its second configuration by being expanded away from the plane of the circumference of the device and then slid (e.g. slid or shifted along the circumference of the wrist-worn device) from a location primarily along a lateral portion of a wrist-worn device to cover the first display.

In an example, a second display can be moved relative to the rest of a wrist-worn device on which it is located. In an example, a second display can be flipped from a first location to a second location on a wrist-worn device. In an example, a second display can be pivoted from a first location to a second location on a wrist-worn device. In an example, a second display can be rotated from a first location to a second location on a wrist-worn device. In an example, a second display can be flipped from a primarily lateral location to a primarily dorsal location on a wrist-worn device. In an example, a second display can be pivoted from a primarily lateral location to a primarily dorsal location on a wrist-worn device. In an example, a second display can be rotated from a primarily lateral location to a primarily dorsal location on a wrist-worn device.

In an example, a second display can be moved relative to the rest of a wrist-worn device on which it is located. In an example, a second display can be flipped from a first location to a second location on a wrist-worn device and then expanded. In an example, a second display can be pivoted from a first location to a second location on a wrist-worn device and then expanded. In an example, a second display can be rotated from a first location to a second location on a wrist-worn device and then expanded. In an example, a second display can be flipped from a primarily lateral location to a primarily dorsal location on a wrist-worn device and then expanded. In an example, a second display can be pivoted from a primarily lateral location to a primarily dorsal location on a wrist-worn device and then expanded. In an example, a second display can be rotated from a primarily lateral location to a primarily dorsal location on a wrist-worn device and then expanded.

In an example, a second display can be moved from a first configuration to a second configuration, or vice versa. In an example, when a second display is in a first configuration, the portion of the device among the four portions (dorsal, ventral, first lateral, and second lateral) on which the greatest percentage of the second light-emitting display is located is a lateral portion. In an example, a second display can be located entirely on the lateral portion of the device. In an example, when a second display is in a first configuration, a second display can be located primarily on the lateral portion of the device. In an example, when a second display is in a first configuration, at least 75% of a second display can be located on the lateral portion of the device. In an example, when a second display is in a first configuration, at least 50% of a second display can be located on the lateral portion of the device. In an example, when a second display is in a first configuration, a second display can be centered on the center of the lateral portion of the device.

In an example, when a second display is in a second configuration, the portion of the device among the four portions (dorsal, ventral, first lateral, and second lateral) on which the greatest percentage of the second light-emitting display is located is a dorsal portion. In an example, a second display can be located entirely on the dorsal portion of the device. In an example, when a second display is in a second configuration, a second display can be located primarily on the dorsal portion of the device. In an example, when a second display is in a second configuration, at least 75% of a second display can be located on the dorsal portion of the device. In an example, when a second display is in a second configuration, at least 50% of a second display can be located on the dorsal portion of the device. In an example, when a second display is in a second configuration, a second display can be centered on the center of the dorsal portion of the device.

In an example, a second display, even in its first configuration, can be larger than a first display. In an example, a second display can have the same width as a first display, along an axis which is perpendicular to the plane of the circumference of the device, but have a length which is at least 50% greater than the length of a first display, along an axis which is parallel to the plane of the circumference of the device. In an example, a second display can span between 20% and 40% of the circumference of a person's wrist and/or lower arm in its first configuration. In an example, a second display can have a rectangular shape. In an example, a second display can have an arcuate (e.g. curved) rectangular shape In an example, a wearable device can further comprise a hinge and/or movable joint around which a second display flips, pivots, folds, and/or rotates as the second display is changed from its first configuration to its second configuration, or vice versa. In an example, a wearable device can further comprise a hinge and/or movable joint around which a second display flips, pivots, and/or rotates in one step of the second display changing from its first configuration to its second configuration, or vice versa. In an example, this hinge and/or movable joint can be perpendicular to the circumference of the wearable device. In an example, this hinge and/or movable joint can be orthogonal to the plane of the circumference of the wearable device. In an example, an end of the second display which is not attached to the hinge and/or movable joint can move toward in a dorsal direction as the second display is changed from its first configuration to its second configuration. In an example, an end of the second display which is not attached to the hinge and/or movable joint can move toward in a dorsal direction as the second display in one step of the second display changing from its first configuration to its second configuration.

In an example, the image-displaying surface of a second display can face inward (toward the surface the person's wrist) in the first configuration and can face outward (away from the surface of the person's wrist) after the display has been flipped, pivoted, and/or rotated from the first configuration into the second configuration. In an example, the image-displaying surface of a second display can face inward (facing away from and not being visible to the user) in the first configuration and can face outward (facing toward and being visible to the user) after the display has been flipped, pivoted, and/or rotated from the first configuration into the second configuration.

In an example, a dorsal side (or end) of a second display can be connected to the rest of the device by one or more hinges and/or moveable joints, around which the second display flips, pivots, and/or rotates from its first configuration to its second configuration. In an example a ventral side (or end) of second display can be releasably-connected to the rest of the device (e.g. by a snap, clip, magnet, pin, hook, or hook-and-loop fabric), wherein it is connected in the first configuration and disconnected in the second configuration.

In an example, a second display can be flexible, bendable, and/or rollable. In an example, a second display can be expandable. In an example, a second display can have a variable size which changes over time. In an example, a second display can be expanded from a first configuration with a first size to a second configuration with a second size, wherein the second size is greater than the first size. In an example, the second size can be at least twice the first size. In an example, a second display can have two configurations. In an example, a second display can be expanded in its second configuration relative to its first configuration. In an example, the size of a second display in its second configuration can be between 150% and 300% of the size of the second display in its first configuration. In an example, the size of a second display in its second configuration can be at least twice the size of the second display in its first configuration.

In an example, a second display can have a square (or square with rounded vertexes) shape in its first (unexpanded) configuration and a rectangular (or rectangular with rounded vertexes) shape in its second (expanded) configuration. In an example, a second display can have a square (or square with rounded vertexes) shape in its first (unexpanded) configuration and a rectangular (or rectangular with rounded vertexes) shape in its second (expanded) configuration, wherein a narrow side of the rectangle is equal in length to a side of the square. In an example, a second display can have a square (or square with rounded vertexes) shape with a first size in its first (unexpanded) configuration and a square (or square with rounded vertexes) shape with a second size in its second (expanded) configuration, wherein the second size is at least twice as large as the first size.

In an example, a second display can have an arcuate shape which is substantially parallel to the arcuate shape of a lateral portion of the device when the second display is in its first configuration. In an example, the shape of a second display in its first configuration can be a section of cylinder which is substantially parallel to the surface of a person's wrist. In an example, a second display can be longitudinally-concave in its first configuration and longitudinally-flat in its second configuration. In an example, a second display can be longitudinally-convex in its first configuration and longitudinally-flat in its second configuration.

In an example, a second display can have a plurality of axes and be expanded (from its first configuration to its second configuration) in the direction of just one of its axes. In an example, a second display can have a plurality of axes and be expanded only in a direction which is parallel to its shortest axis. Alternatively, a second display can have a plurality of axes and be expanded only in the direction which is parallel to its longest axis. In an example, a second display can be expanded (from its first configuration to its second configuration) in a direction which is orthogonal to the plane of the circumference of the device and/or the person's wrist. Alternatively, a second display can be expanded (from its first configuration to its second configuration) in a direction which is parallel to the plane of the circumference of the device. In an example, a second display can be expanded (from its first configuration to its second configuration) in a direction which is parallel to the plane of the circumference of the device and tangential to the circumference of the device.

In the example shown in FIG. 4, a second display is expanded in one direction. If this device were to be worn on a person's left wrist and/or lower arm, then the direction of expansion of the second display would be: away from the plane of the circumference of the device, toward the person's elbow, and onto the dorsal surface of the person's lower arm. In an alternative example, the direction of expansion of the second display can be in the opposite direction: away from the plane of the circumference of the device, away from the person's elbow, and onto the back of the person's hand. In another example, a second display could be expanded in two opposite directions: (1) expansion away from the plane of the circumference of the device, toward the person's elbow, and onto the dorsal surface of the person's lower arm; and also (2) expansion away from the plane of the circumference of the device, away from the person's elbow, and onto the back of the person's hand.

In an example, a flexible second display can be expanded (e.g. expanded, extended, lengthened, and/or widened) being unrolled (e.g. unrolled, unwound, and/or uncoiled) from a roller (e.g. roller, spool, cylinder, rod, or pin). In an example, a flexible second display can be expanded from its (unexpanded) first configuration to its second (expanded) configuration as it is unrolled (e.g. unrolled, unwound, and/or uncoiled) from a roller (e.g. roller, spool, cylinder, rod, or pin). In an example, a flexible second display can be manually expanded when user pulls a side (or end) of the display which is opposite to a roller (e.g. roller, spool, cylinder, rod, or pin) around which the display is rolled, wound, and/or coiled. In an example, a flexible second display can be automatically expanded when an actuator rotates a roller (e.g. roller, spool, cylinder, rod, or pin) around which the display is rolled, wound, and/or coiled, thereby unrolling, unwinding, and/or uncoiling the display.

In an example, a second display can be expanded (e.g. expanded, extended, lengthened, and/or widened) by reducing the degree of overlap between two or more display sections which together comprise the second display. In an example, one display section can be slid outward from underneath another display section. In an example, two display sections can be non-coplanar and overlapping in a first configuration and can be coplanar and non-overlapping in a second configuration. In an example, two or more display sections can be rigid and separate from each other, wherein the second display is expanded by sliding one rigid section out from underneath the other rigid section. Alternatively, two or more display sections can be flexible, continuous with each other around a rotating roller (e.g. roller, spool, cylinder, rod, or pin), wherein the size of the upper (visible) section is increased and the size of the lower (non-visible) section is decreased by rotating the roller (e.g. roller, spool, cylinder, rod, or pin).

In an example, the flexibility and/or rigidity of the second display can be changed. In an example, the second display can be made more flexible to facilitate moving it from its first configuration to its second configuration, but can then be made more rigid to facilitate a stable, flat image (and/or its use as a touch screen). In an example, a second display can further comprise (a layer of) a plurality of narrow rigid connected sections, wherein the second display becomes more flexible (less rigid) when the sections are more loosely connected to each other and the second display becomes more rigid (less flexible) when the sections are more tightly connected to each other. In an example, the degree to which sections are loosely or tightly connected to each other can be adjusted. In an example, the degree to which sections are loosely or tightly connected to each other can be adjusting the tension of one or more filaments, wires, or strings which connect the sections to each other. In an example, narrow rigid connected sections can have "tongue-and-grove" shapes, wherein a protrusion on an end of section fits into a recess on an end of a neighboring section when the sections are pulled close together. In this manner, the second display be flexible for changing configuration (including possibly changing curvature), but can be made into a relatively flat, rigid surface for use as a flat, rigid touch screen in its expanded configuration.

In an example, a second display can comprise at least four layers. A (top) first layer can be a flexible protective layer. A second layer can comprise an array and/or matrix of light-emitters. A third layer can comprise a plurality of electroconductive pathways which provide power to the light-emitters. A (bottom) fourth layer can comprise a plurality of flexibly-connected segments, wherein changing the spacing between the segments changes the overall flexibility and/or rigidity of the display. The fourth layer can be made less rigid, more flexible, and more arcuate to facilitate changing the configuration of the display, but can also be made more rigid, less flexible, and more flat to facilitate use of the display as a touch screen.

In an example, a (bottom) fourth layer of a second display can comprise a plurality of connected "tongue-and-groove" segments which interlocking protrusions and recesses which fit into each other when they are pulled tightly together. In an example, the "tongue-and-groove" segments can be connected by filaments, wires, or strings. When the tension of the filaments, wires, or strings is decreased, then the fourth layer (and the whole display) becomes less rigid, more flexible, and more arcuate. When the tension of the filaments, wires, or strings is increased, then the fourth layer (and the whole display) becomes more rigid, less flexible, and more flat.

In another example, a (bottom) fourth layer of a second display can comprise material whose rigidity, flexibility, and/or shape is affected by the application of electrical energy. In an example, a fourth layer can become more rigid, less flexible, and/or more flat when electrical energy is applied to it. Alternative, a fourth layer can become less rigid, more flexible, and/or more arcuate when electrical energy is applied to it. In an example, a fourth layer can be made from an electroactive polymer (EAP). In an example, a fourth layer can be made from shape-memory material.

In an example, a second display can comprise at least three layers. A (top) first layer can be a flexible protective layer. A second layer can comprise an array and/or matrix of light-emitters and electroconductive pathways which provide power to the light-emitters. A third layer can comprise a plurality of flexibly-connected segments, wherein changing the spacing between the segments changes the overall flexibility and/or rigidity of the display. The third layer can be made less rigid, more flexible, and more arcuate to facilitate changing the configuration of the display, but can also be made more rigid, less flexible, and more flat to facilitate use of the display as a touch screen.

In an example, this device can further comprise a battery, a data processor, and a wireless data transmitter and/or receiver. In an example, this device can further comprise other components selected from the group consisting of: battery, data processor, electromagnetic actuator, infrared light sensor, laser, microphone, motion sensor, one or more buttons, speaker, spectroscopy sensor, visible light sensor, watch crown, wireless data receiver, and wireless data transmitter. Relevant device variations discussed elsewhere in this disclosure or in priority-linked disclosures can be applied to the example shown in this figure.

Figure 5:
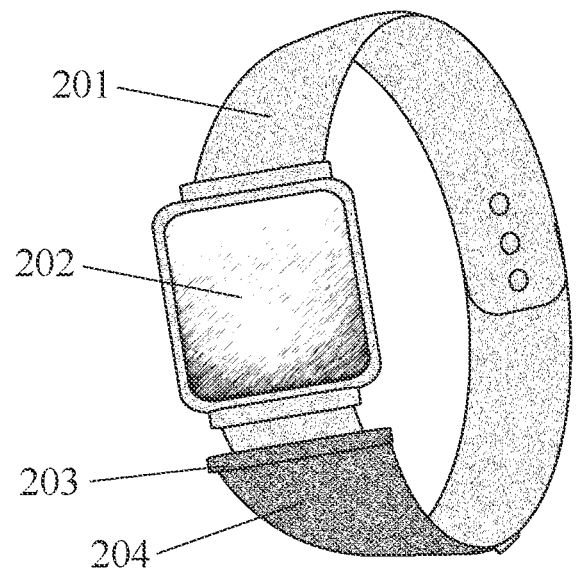
FIG. 5 shows a cross-sectional side view of the device shown in FIG. 2.
Figure 5:
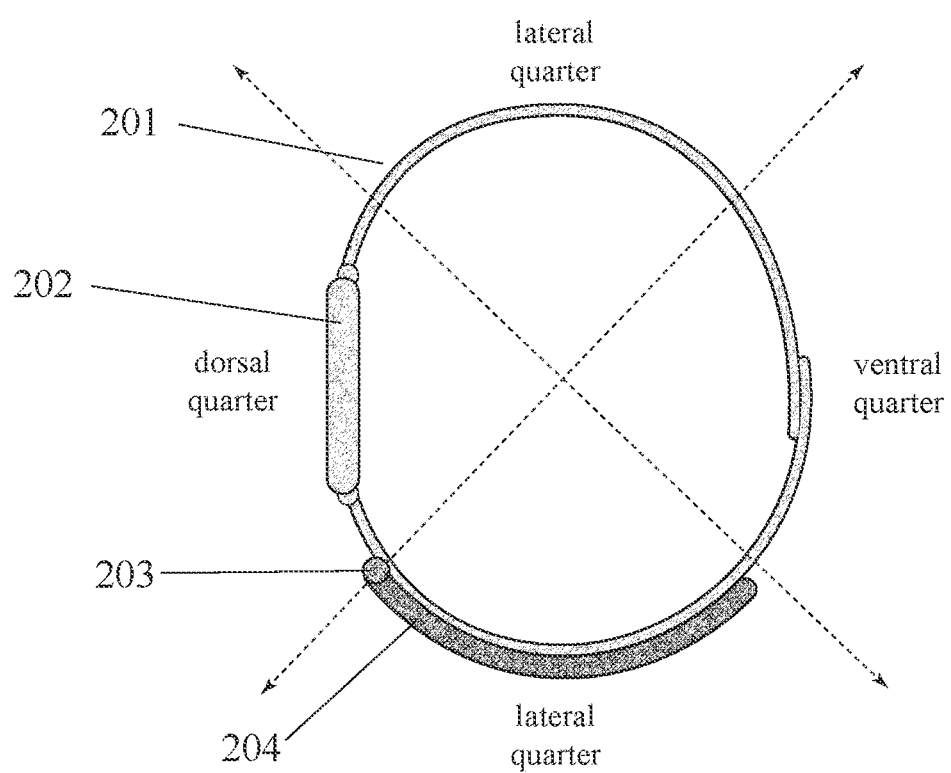

FIG. 5 shows a different view of the device which was first shown in FIG. 2. The upper portion of FIG. 5 repeats the view which was shown in FIG. 2. The lower portion of FIG. 5 provides an additional cross-sectional side view of this device. In these figures, the second display is in its first configuration. It is unexpanded and is located on a lateral portion of the device.

With respect to specific components, FIG. 5 shows a wearable device with an expandable display in a first configuration comprising: (a) a wearable device 201 which is configured to be worn around at least three-quarters of the circumference of a person's wrist and/or lower arm, wherein a dorsal portion of the device is configured to be worn on a dorsal quarter of the circumference of the person's wrist and/or lower arm, wherein a ventral portion of the device is configured to be worn on at least part of the ventral quarter of the circumference of the person's wrist and/or lower arm, wherein a first lateral portion of the device is configured to be worn on a first lateral quarter of the circumference of the person's wrist and/or lower arm between the dorsal quarter and the ventral quarter, wherein a second lateral portion of the device is configured to be worn on a second lateral quarter of the circumference of the person's wrist and/or lower arm between the dorsal quarter and the ventral quarter, wherein the second lateral quarter is opposite the first lateral quarter; (b) a first light-emitting display 202 on the wearable device, wherein the portion of the device on which the greatest percentage of the first light-emitting display is located is the dorsal portion; and (c) a second light-emitting display 204 on the wearable device, wherein the second light-emitting display has a first configuration (shown here) in which the portion of the device on which the greatest percentage of the second light-emitting display is located is the first lateral portion or the second lateral portion and the second light-emitting display is a first size, and wherein the second light-emitting display has a second configuration in which the portion of the device on which the greatest percentage of the second light-emitting display is located is the dorsal portion and the second light-emitting display is a second size, and wherein the second size is greater than the first size. This example also includes a hinge and/or movable joint 203 around which the second display is flipped, pivoted, and/or rotated from the first configuration to the second configuration.

The lower portion of FIG. 5 shows an example of how the second display in its first configuration can curve around a lateral portion of the device. In this example, the second display in its first configuration is substantially parallel to the inner surface of the device (and also the surface of the person's wrist). In an example, the imaging side of the second display in its first configuration faces inward toward the person's wrist and is not visible to the person. In another example, both sides of the second display can show images, so that the second display shows a visible image in this first configuration as well as in the second configuration.

In this example, a second display in its first configuration is arcuate. In this example, the second display in its first configuration curves around the person's wrist. In this example, the dorsal-facing end of the second display is permanently attached to the rest of the device by a hinge and/or movable joint. In this example, the ventral-facing end of the second display can be (detached and) moved away from the rest of the device in order to flip, pivot, and/or rotate the second display from its first configuration to its second configuration. In an example, the ventral-facing end of the second display can be reversibly attached to (or detached from) the rest of the device by a snap, clip, clasp, magnet, hook-and-loop fabric, hook, pin, or buckle.

In this example, the hinge and/or moveable joint is on the dorsal portion of the device (over the dorsal quarter of the person's wrist). In this example, the second display spans between 75% and 90% of the lateral portion of the device (over the lateral quarter of the person's wrist). In another example, the second display can span the entire lateral portion of the device. In this example, the second display is primarily on the lateral portion of the device in the first configuration, but the dorsal-facing end the second display also extends over the dorsal portion of the device even in the first configuration. Relevant device variations discussed elsewhere in this disclosure or in priority-linked disclosures can be applied to the example shown in this figure.

Figure 6:
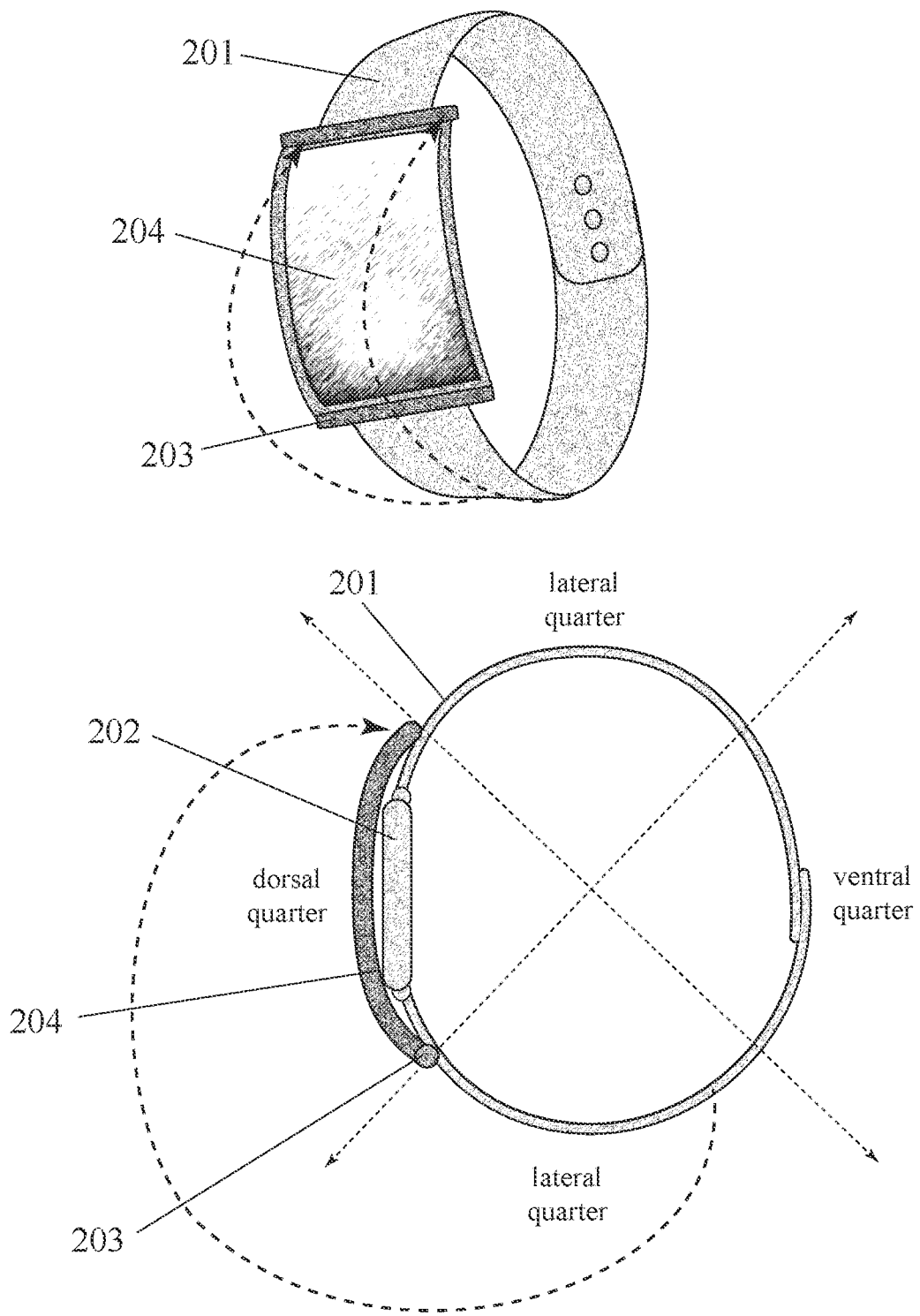
FIG. 6 shows a cross-sectional side view of the device shown in FIG. 3.

FIG. 6 shows a different view of the device which was first shown in FIG. 3. The upper portion of FIG. 6 repeats the view which was shown in FIG. 3. The lower portion of FIG. 6 provides an additional cross-sectional side view of this device. In these figures, the second display has been flipped, pivoted, and/or rotated around the hinge and/or joint, but has not yet been expanded.

With respect to specific components, FIG. 6 shows a wearable device with an expandable display in a first configuration comprising: (a) a wearable device 201 which is configured to be worn around at least three-quarters of the circumference of a person's wrist and/or lower arm, wherein a dorsal portion of the device is configured to be worn on a dorsal quarter of the circumference of the person's wrist and/or lower arm, wherein a ventral portion of the device is configured to be worn on at least part of the ventral quarter of the circumference of the person's wrist and/or lower arm, wherein a first lateral portion of the device is configured to be worn on a first lateral quarter of the circumference of the person's wrist and/or lower arm between the dorsal quarter and the ventral quarter, wherein a second lateral portion of the device is configured to be worn on a second lateral quarter of the circumference of the person's wrist and/or lower arm between the dorsal quarter and the ventral quarter, wherein the second lateral quarter is opposite the first lateral quarter; (b) a first light-emitting display 202 on the wearable device, wherein the portion of the device on which the greatest percentage of the first light-emitting display is located is the dorsal portion; and (c) a second light-emitting display 204 on the wearable device, wherein the second light-emitting display has a first configuration in which the portion of the device on which the greatest percentage of the second light-emitting display is located is the first lateral portion or the second lateral portion and the second light-emitting display is a first size, and wherein the second light-emitting display has a second configuration in which the portion of the device on which the greatest percentage of the second light-emitting display is located is the dorsal portion and the second light-emitting display is a second size, and wherein the second size is greater than the first size.

This example also includes a hinge and/or movable joint 203 around which the second display is flipped, pivoted, and/or rotated from the first configuration to the second configuration. In this figure, the second display has been flipped, pivoted, and/or rotated around the hinge and/or moveable joint to a location which is primarily on the dorsal portion of the device (over the dorsal quarter of the person's wrist). In this example, one end of the second display remains connected to the rest of the device via the hinge and/or joint and the other end of the second display moves away from the device, and then back toward the device in an arc in space. In an example, this end of the second display can be reversibly (re)attached to the device when the second display is in its second configuration by a snap, clip, clasp, magnet, hook-and-loop fabric, hook, pin, or buckle.

In this example, the second display covers the first display when the second display is in its second configuration. In an example, a second display in its second configuration can span the entire dorsal portion of the device (over the entire dorsal quarter of the person's wrist). In an example, a second display in its second configuration can not only span the entire dorsal portion of the device, but also partly extend onto one or both lateral portions of the device. Relevant device variations discussed elsewhere in this disclosure or in priority-linked disclosures can be applied to the example shown in this figure.

Figure 7:
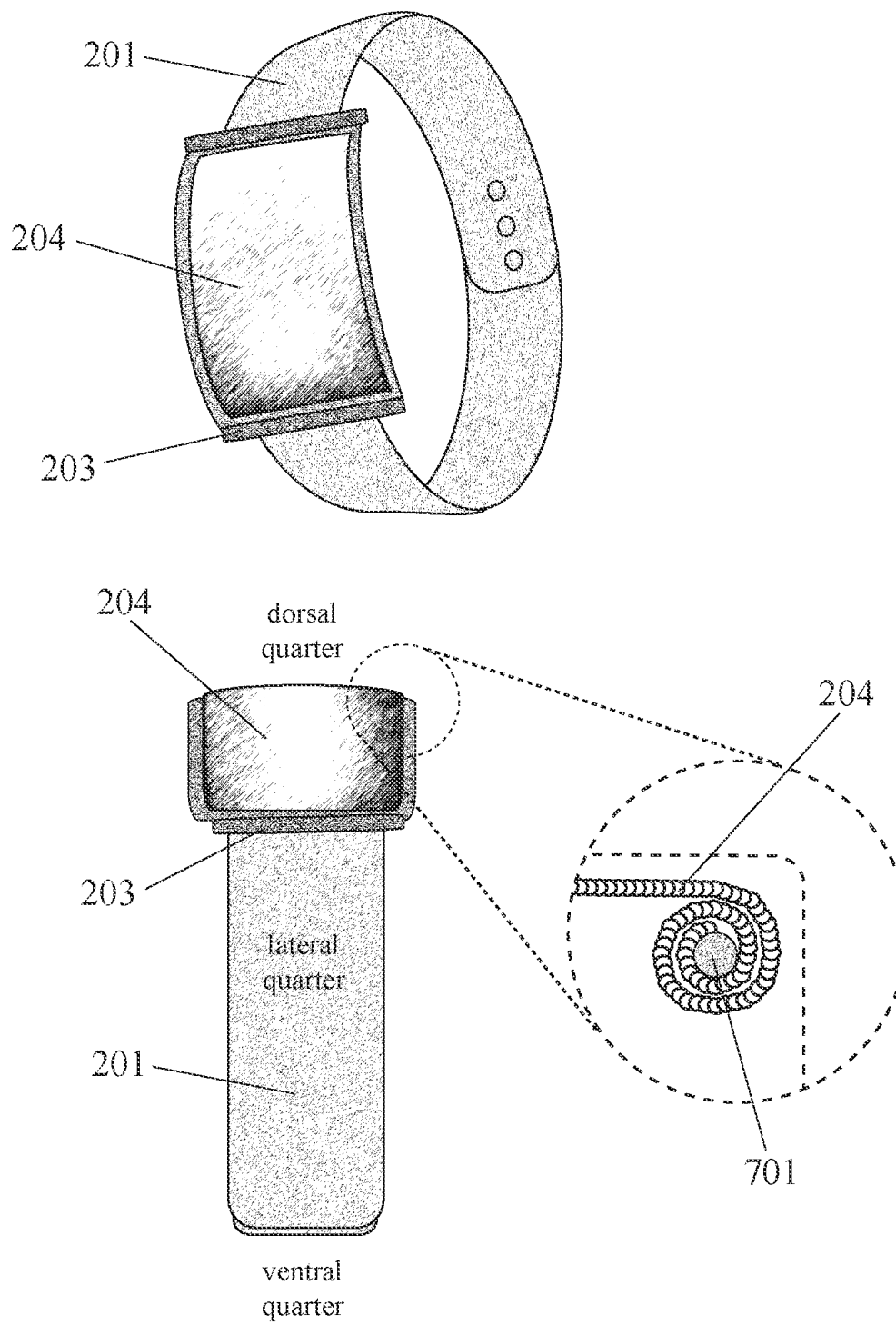
FIGS. 7 and 8 show two sequential cross-sectional side views of a rollable display embodiment of the device shown in FIGS. 3 and 4, including close-up cross-sectional views of a roller around which the display is rolled.
Figure 8:
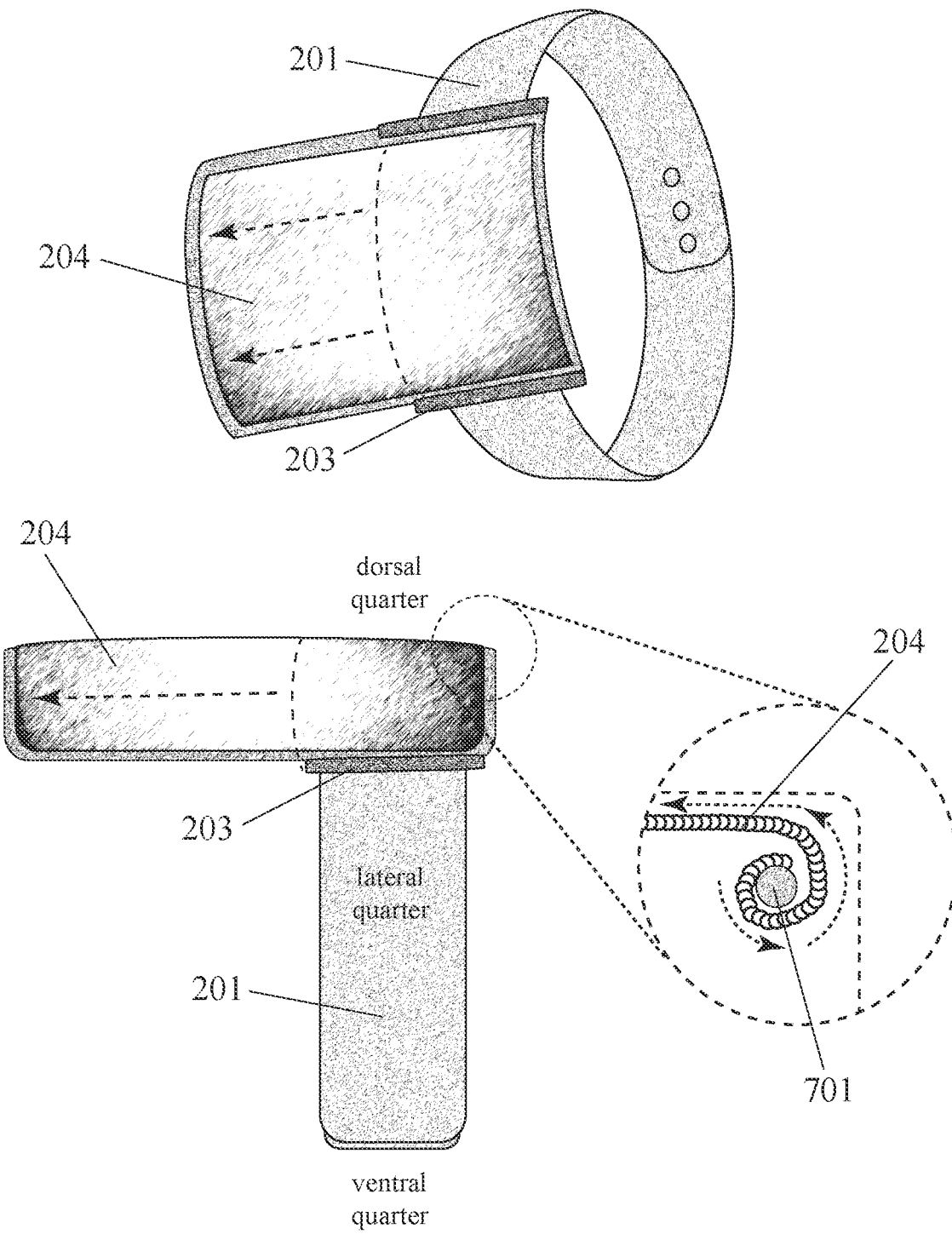

FIGS. 7 and 8 show details (and close-up cross-sectional views) concerning one mechanism by which the second device can be expanded. In this example, the expansion mechanism is unrolling. The visible size of the second display is smaller when the display is wound around a roller (e.g. roller, spool, cylinder, rod, or pin) and the visible size of the second display is larger when it is unwound from the roller. The upper portions of FIGS. 7 and 8 repeat the views of this device which were introduced in FIGS. 3 and 4. The lower portions of FIGS. 7 and 8 provide additional side views of the device, including close-up cross-sectional views (in dotted line circles) of a roller (e.g. roller, spool, cylinder, rod, or pin) 701 around which the second display is rolled in an unexpanded configuration and from which the second display is unrolled in an expanded configuration.

FIGS. 7 and 8 show additional close-up cross-sectional views of one possible mechanism for expansion of the second display. In this example, the mechanism for expansion of the second display is rolling or unrolling. In this example, the device includes a roller (e.g. roller, spool, cylinder, rod, or pin) around which one side of the second display is rolled (e.g. rolled, coiled, and/or wound) into a non-expanded configuration and from which the second display is unrolled (e.g. unrolled, uncoiled, and/or unwound) into expanded configuration.

In FIG. 7, the second display has been flipped, pivoted, and/or rotated around the hinge and/or joint, but has not yet been expanded by unrolling (e.g. unrolling, uncoiling, and/or unwinding). In FIG. 8, the second display has been expanded by unrolling (e.g. unrolling, uncoiling, and/or unwinding). The upper portions of FIGS. 7 and 8 repeat the oblique side views of this device which were shown in FIGS. 3 and 4. The lower portions of FIGS. 7 and 8 provide additional side views of the device, including close-up cross-sectional views (in a dotted line circle) of a roller (e.g. roller, spool, cylinder, rod, or pin) 701 around which one side of the second display is either rolled or unrolled.

In addition to roller 701, FIGS. 7 and 8 show a wearable device with an expandable display in a first configuration comprising: (a) a wearable device 201 which is configured to be worn around at least three-quarters of the circumference of a person's wrist and/or lower arm, wherein a dorsal portion of the device is configured to be worn on a dorsal quarter of the circumference of the person's wrist and/or lower arm, wherein a ventral portion of the device is configured to be worn on at least part of the ventral quarter of the circumference of the person's wrist and/or lower arm, wherein a first lateral portion of the device is configured to be worn on a first lateral quarter of the circumference of the person's wrist and/or lower arm between the dorsal quarter and the ventral quarter, wherein a second lateral portion of the device is configured to be worn on a second lateral quarter of the circumference of the person's wrist and/or lower arm between the dorsal quarter and the ventral quarter, wherein the second lateral quarter is opposite the first lateral quarter; (b) a first light-emitting display 202 on the wearable device, wherein the portion of the device on which the greatest percentage of the first light-emitting display is located is the dorsal portion; and (c) a second light-emitting display 204 on the wearable device, wherein the second light-emitting display has a first configuration in which the portion of the device on which the greatest percentage of the second light-emitting display is located is the first lateral portion or the second lateral portion and the second light-emitting display is a first size, and wherein the second light-emitting display has a second configuration in which the portion of the device on which the greatest percentage of the second light-emitting display is located is the dorsal portion and the second light-emitting display is a second size, and wherein the second size is greater than the first size. This example also includes a hinge and/or movable joint 203 around which the second display is flipped, pivoted, and/or rotated from the first configuration to the second configuration.

In this example, the second display is rollable. In this example, the second display can be rolled, coiled, and/or wound without damage to the display. In this example, the second display can be wound or unwound around a roller (e.g. roller, spool, cylinder, rod, or pin) without damage to the display. In an example, a second display can be rolled, coiled, and/or wound around a roller (e.g. roller, spool, cylinder, rod, or pin) and also unrolled, uncoiled, and/or unwound from the roller (e.g. roller, spool, cylinder, rod, or pin) without damage to the display. In an example, a second display can be rolled, coiled, and/or wound around a roller (e.g. roller, spool, cylinder, rod, or pin) into an unexpanded configuration and unrolled, uncoiled, and/or unwound from the roller (e.g. roller, spool, cylinder, rod, or pin) into an expanded configuration.

In an example, the (outward-facing) size of a second display can be reduced by rolling, coiling, and/or winding (e.g. one end of) the display around a roller (e.g. roller, spool, cylinder, rod, or pin). In an example, the (outward-facing) size of the second display can be increased by unrolling, uncoiling, and/or unwinding (e.g. one end of) the display from around the roller (e.g. roller, spool, cylinder, rod, or pin). In an example, the visible surface area of a second display can be reduced by rolling, coiling, and/or winding (e.g. one end of) the display around a roller (e.g. roller, spool, cylinder, rod, or pin). In an example, the visible surface area of the second display can be increased by unrolling, uncoiling, and/or unwinding (e.g. one end of) the display from around the roller (e.g. roller, spool, cylinder, rod, or pin).

In an example, the lower surface and/or the lateral sides of the second display can have protrusions or recesses (e.g. teeth, ridges, notches, or undulations) and the roller (e.g. roller, spool, cylinder, rod, or pin) around which the display is rolled, coiled, and/or wound can have recesses or protrusions (e.g. teeth, ridges, notches, or undulations) which are geometrically complementary to those of the display. In an example, the protrusions or recesses on the display can interdigitate (e.g. interdigitate, engage, and/or mesh) with the recesses or protrusions on the roller. In an example, a roller (e.g. roller, spool, cylinder, rod, or pin) can comprise a gear which engages protrusions or recesses (e.g. teeth, ridges, notches, or undulations) on the lower surface of a second display.

In an example, a roller (e.g. roller, spool, cylinder, rod, or pin) around which a second display is rolled, coiled, and/or wound can have a circular cross-sectional shape. In an example, a roller (e.g. roller, spool, cylinder, rod, or pin) around which a second display is rolled, coiled, and/or wound can have an elliptical or oval cross-sectional shape. In an example, a roller (e.g. roller, spool, cylinder, rod, or pin) around which a second display is rolled, coiled, and/or wound can have a polygonal (e.g. hexagonal) cross-sectional shape.

In an example, a roller (e.g. roller, spool, cylinder, rod, or pin) around which a second display is rolled, coiled, and/or wound can have a gear or sun-burst cross-sectional shape. In an example, a roller (e.g. roller, spool, cylinder, rod, or pin) around which a second display is rolled, coiled, and/or wound can have an involute curve tooth cross-sectional shape. In an example, a roller (e.g. roller, spool, cylinder, rod, or pin) around which a second display is rolled, coiled, and/or wound can have a radially-asymmetric cross-sectional shape.

In an example, a second display can be rolled, coiled, and/or wound around a single roller (e.g. roller, spool, cylinder, rod, or pin). In an example, a second display can be rolled, coiled, and/or wound around two or more rollers (e.g. rollers, spools, cylinders, rods, or pins). In an example, the distance between the two rollers (e.g. rollers, spools, cylinders, rods, or pins) can be changed. In an example, the (outward-facing) size of a second display can be increased by decreasing the distance between the two rollers (e.g. rollers, spools, cylinders, rods, or pins) around which a second display is looped. In an example, a second display can be rolled, coiled, and/or wound around a first roller (e.g. roller, spool, cylinder, rod, or pin) and looped around (e.g. bent around part of the circumference of) a second roller (e.g. roller, spool, cylinder, rod, or pin).

In an example, a flexible second display can be expanded (e.g. expanded, extended, lengthened, and/or widened) being unrolled (e.g. unrolled, unwound, and/or uncoiled) from a roller (e.g. roller, spool, cylinder, rod, or pin). In an example, a flexible second display can be expanded from its (unexpanded) first configuration to its second (expanded) configuration as it is unrolled (e.g. unrolled, unwound, and/or uncoiled) from a roller (e.g. roller, spool, cylinder, rod, or pin). In an example, a flexible second display can be manually expanded when user pulls a side (or end) of the display which is opposite to a roller (e.g. roller, spool, cylinder, rod, or pin) around which the display is rolled, wound, and/or coiled. In an example, a flexible second display can be automatically expanded when an actuator rotates a roller (e.g. roller, spool, cylinder, rod, or pin) around which the display is rolled, wound, and/or coiled, thereby unrolling, unwinding, and/or uncoiling the display. Relevant device variations discussed elsewhere in this disclosure or in priority-linked disclosures can be applied to the example shown in this figure.

Figure 9:
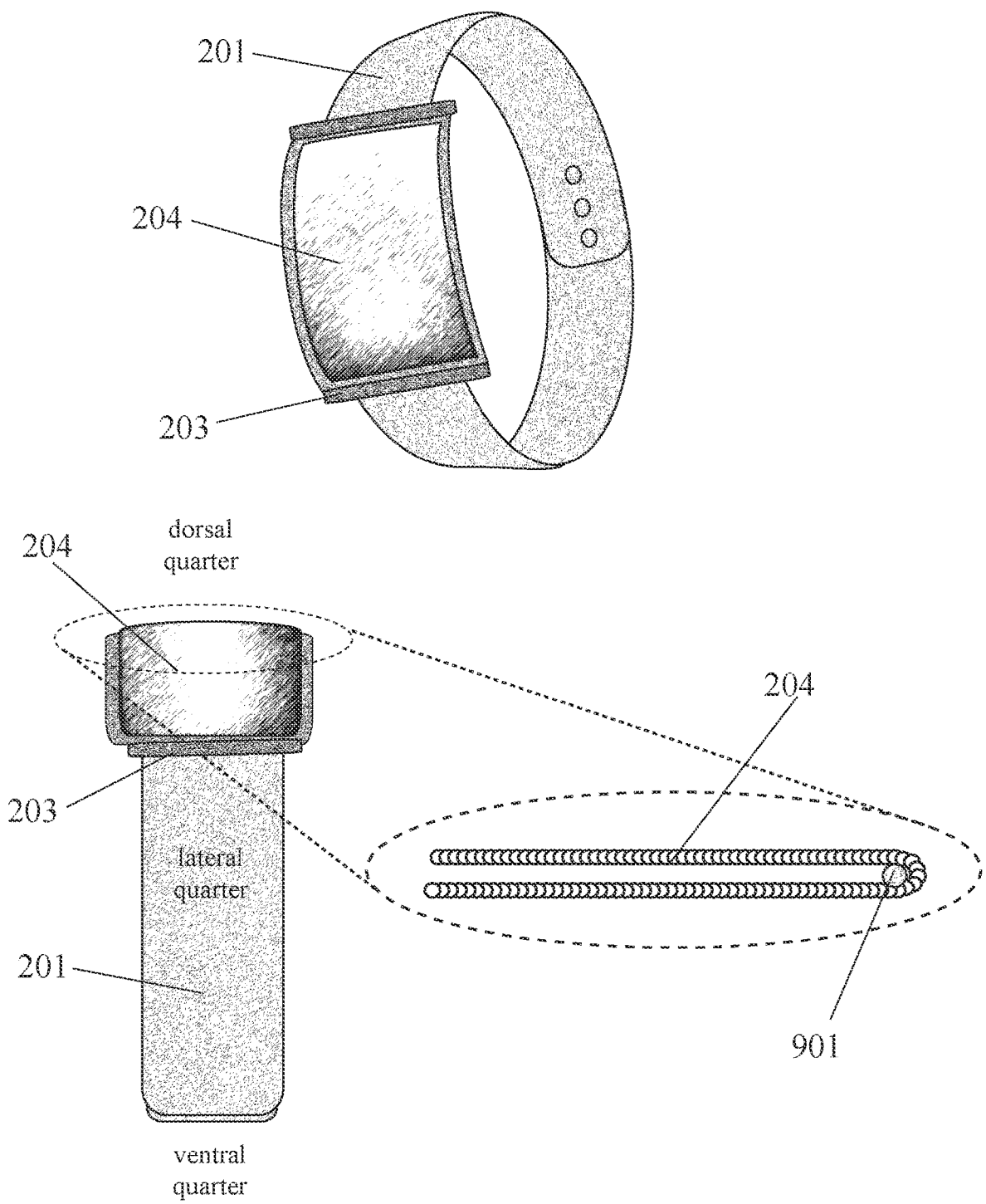
FIGS. 9 and 10 show two sequential cross-sectional side views of a looping display embodiment of the device shown in FIGS. 3 and 4, including close-up cross-sectional views of a roller around which thehe display is looped.
Figure 10:
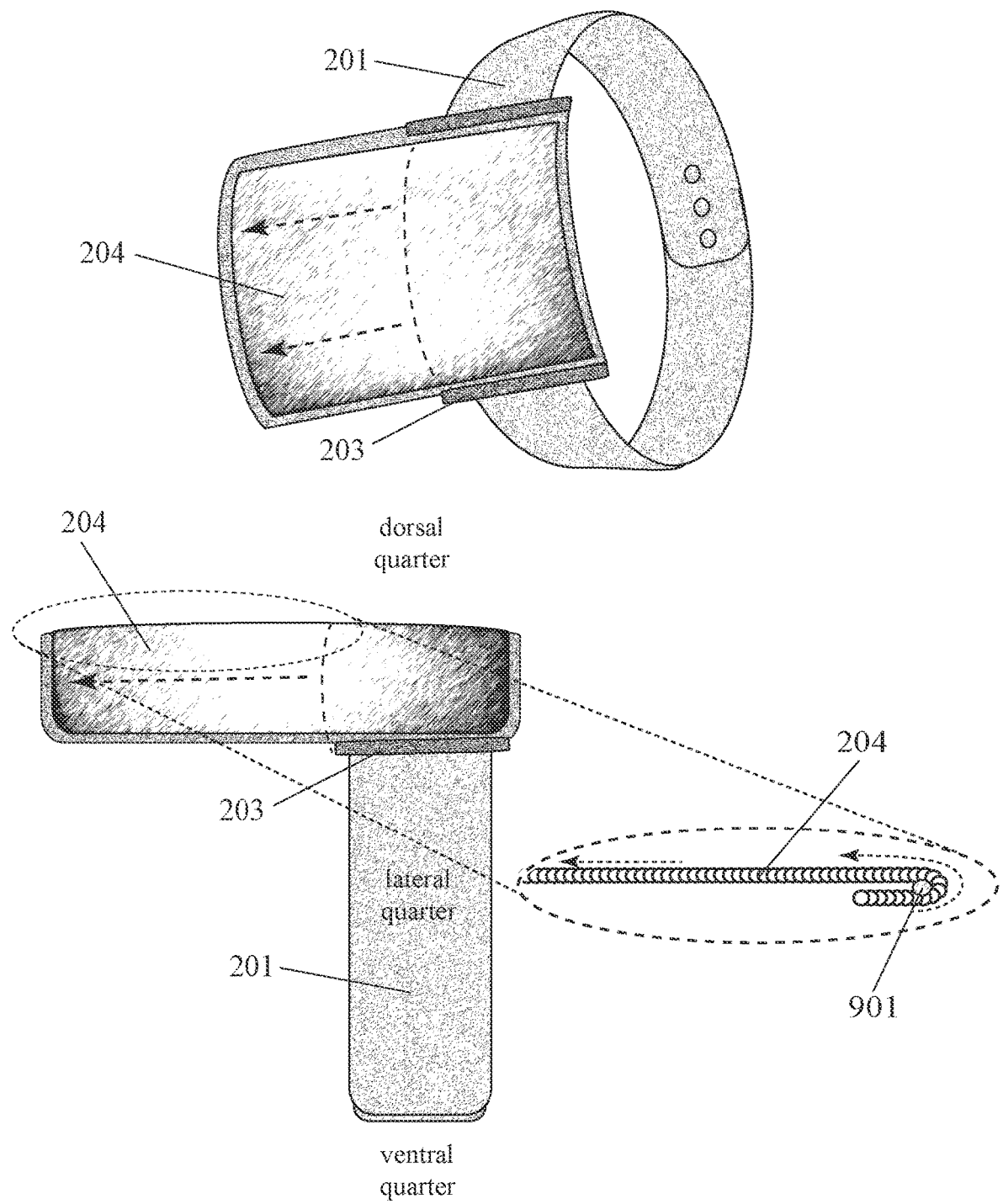

FIGS. 9 and 10 show details (and close-up cross-sectional views) of another possible mechanism by which a second device can be expanded. In this example, the expansion mechanism is called "un-looping". In this disclosure, the terms "looping" and "un-looping" refer to bending and moving a display around part (although not all) of the circumference of a roller. "Looping" is defined as movement of a display around a roller in a direction which increases the extent to which the display overlaps itself "Un-looping" is defined as movement of the display around the roller in the opposite direction which decreases the extent to which the display overlaps itself. Looping is shown in the close-up dotted-line portion of FIG. 9. Un-looping is shown in the close-up dotted-line portion of FIG. 10.

In FIG. 9, the visible size of the second display is smaller as the display loops a roller and overlaps itself to a greater extent. In FIG. 10, the visible size of the second display is larger as the display un-loops from the roller and overlaps itself to a lesser extent. The upper portions of FIGS. 9 and 10 repeat the views of this device which were introduced in FIGS. 3 and 4. The lower portions of FIGS. 9 and 10 provide additional side views of the device, including close-up cross-sectional views (in dotted line circles) of a roller (e.g. roller, spool, cylinder, rod, or pin) 901 around which the second display is looped.

In addition to roller 901, FIGS. 9 and 10 show a wearable device with an expandable display in a first configuration comprising: (a) a wearable device 201 which is configured to be worn around at least three-quarters of the circumference of a person's wrist and/or lower arm, wherein a dorsal portion of the device is configured to be worn on a dorsal quarter of the circumference of the person's wrist and/or lower arm, wherein a ventral portion of the device is configured to be worn on at least part of the ventral quarter of the circumference of the person's wrist and/or lower arm, wherein a first lateral portion of the device is configured to be worn on a first lateral quarter of the circumference of the person's wrist and/or lower arm between the dorsal quarter and the ventral quarter, wherein a second lateral portion of the device is configured to be worn on a second lateral quarter of the circumference of the person's wrist and/or lower arm between the dorsal quarter and the ventral quarter, wherein the second lateral quarter is opposite the first lateral quarter; (b) a first light-emitting display 202 on the wearable device, wherein the portion of the device on which the greatest percentage of the first light-emitting display is located is the dorsal portion; and (c) a second light-emitting display 204 on the wearable device, wherein the second light-emitting display has a first configuration in which the portion of the device on which the greatest percentage of the second light-emitting display is located is the first lateral portion or the second lateral portion and the second light-emitting display is a first size, and wherein the second light-emitting display has a second configuration in which the portion of the device on which the greatest percentage of the second light-emitting display is located is the dorsal portion and the second light-emitting display is a second size, and wherein the second size is greater than the first size. This example also includes a hinge and/or movable joint 203 around which the second display is flipped, pivoted, and/or rotated from the first configuration to the second configuration.

In this example, the second display is looped partially around the roller, but not coiled or wound entirely around the roller. In this example, the second display overlaps itself to a first extent in a non-expanded configuration and overlaps itself to a second extent in an expanded configuration, wherein the second extent is less than the first extent. In this example, the second display extends outward as the side of the lower portion of the display loops upward, around the roller, and becomes part of the upper portion of the display.

In FIG. 9, the second display has been flipped, pivoted, and/or rotated around the hinge and/or joint, but not yet been expanded. In FIG. 9, the display overlaps itself to greater extent. In FIG. 10, the second display has been expanded by having its upper portion un-loop outward from the roller. In FIG. 10, the display overlaps itself to a lesser extent. The upper portions of FIGS. 9 and 10 repeat the oblique side views of this device which were shown in FIGS. 3 and 4. The lower portions of FIGS. 9 and 10 provide additional side views of the device, including dotted line circles which frame close-up cross-sectional views of the roller and overlapping portions of the second display. Relevant device variations discussed elsewhere in this disclosure or in priority-linked disclosures can be applied to the example shown in this figure.

Figure 11:
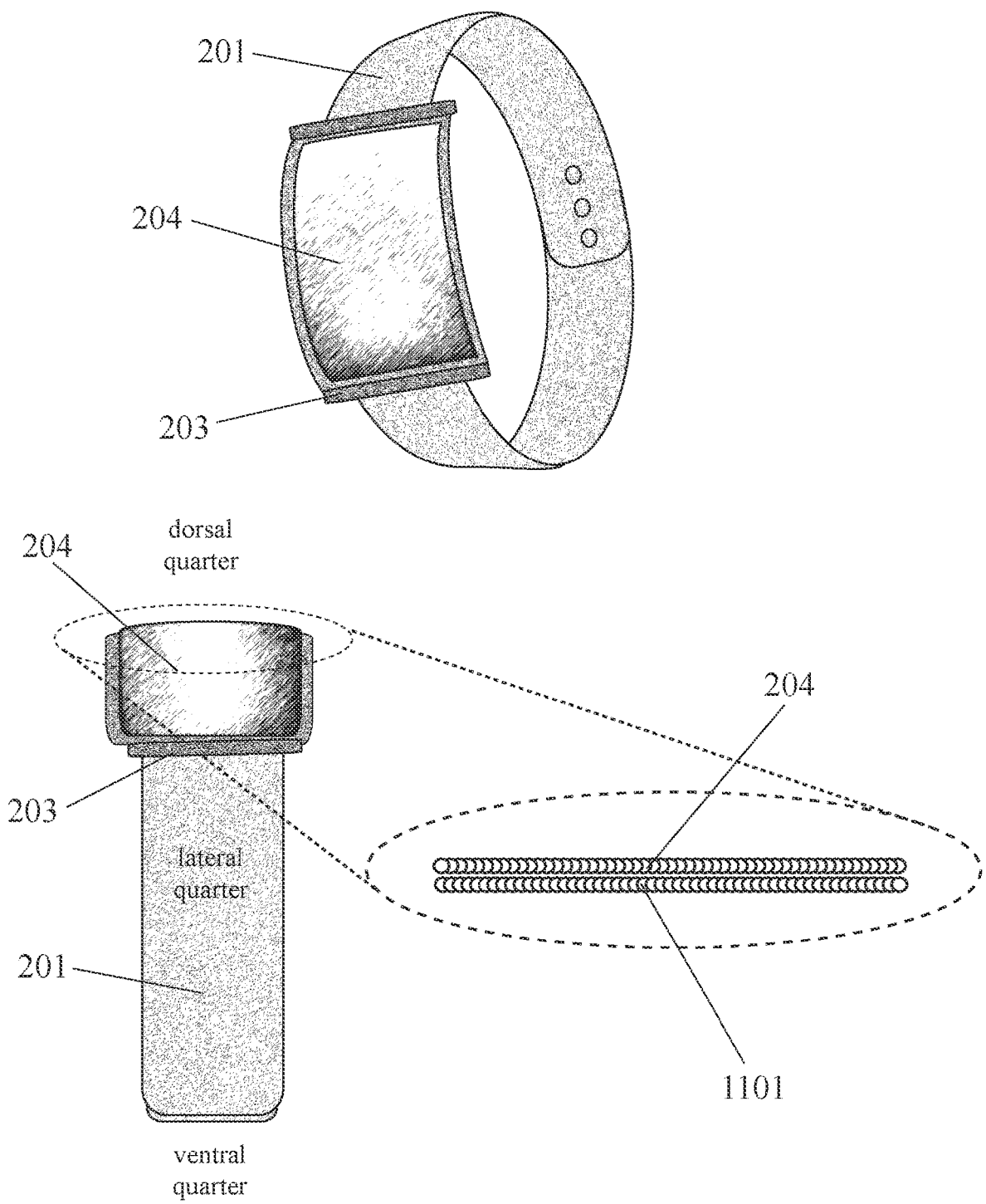
FIGS. 11 and 12 show two sequential cross-sectional side views of a sliding and/or telescoping display embodiment of the device shown in FIGS. 3 and 4, including close-up cross-sectional views of sliding and/or telescoping display sections.
Figure 12:
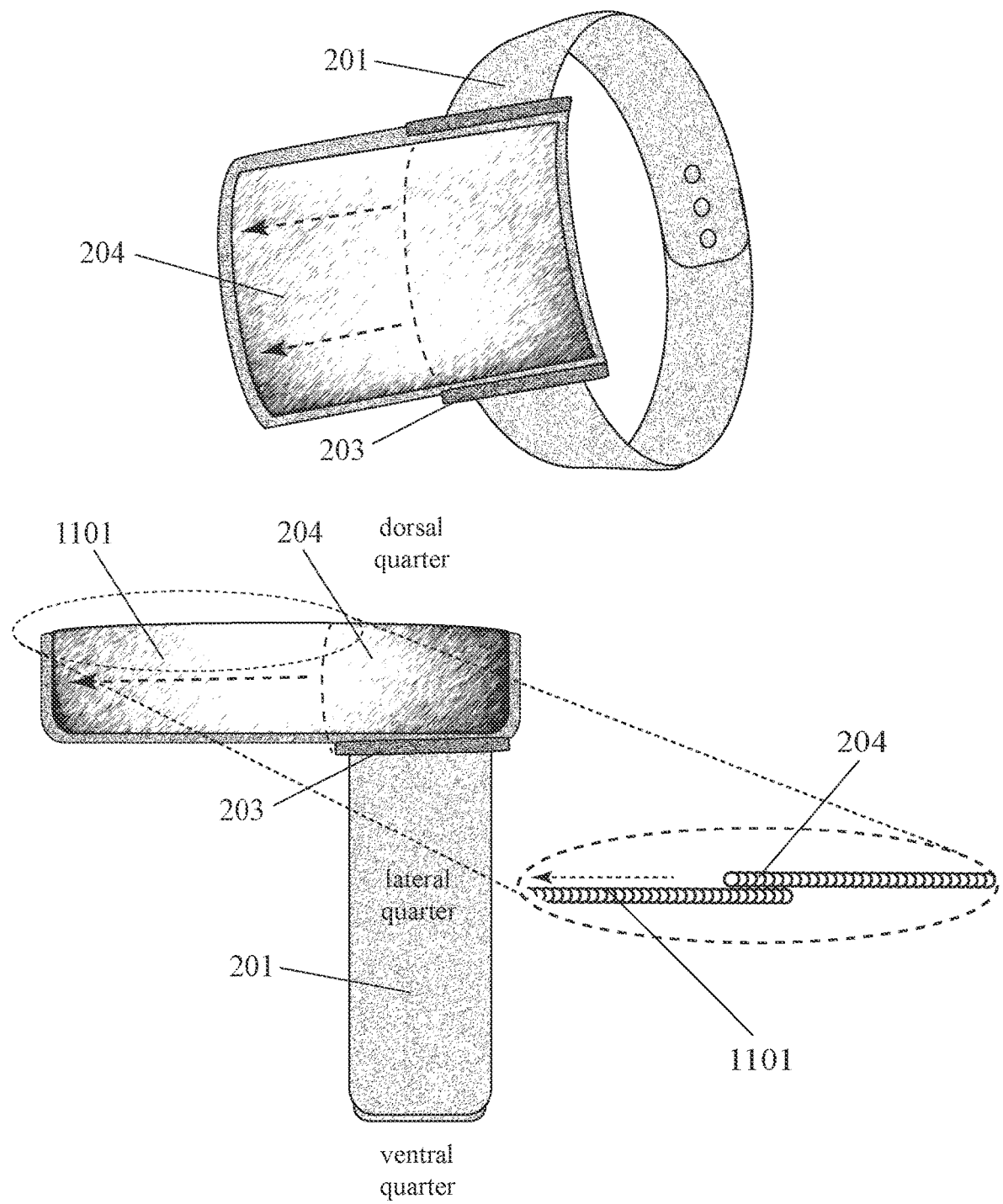

FIGS. 11 and 12 show details (and close-up cross-sectional views) concerning another mechanism by which the second device can be expanded. In this example, the expansion mechanism is sliding (or telescoping).

In this example, a second display comprises two or more sliding (or telescoping) sections, including upper section 204 and lower section 1101. When the lower section slides (or telescopes) out from under the upper display section, then the overall visible size of the second display increases.

The upper portions of FIGS. 11 and 12 repeat the views of this device which were introduced in FIGS. 3 and 4. The lower portions of FIGS. 11 and 12 provide additional side views of the device, including close-up cross-sectional views (in dotted line circles) of the two sliding (or telescoping) sections of the second display. In FIG. 11, the second display has been flipped, pivoted, and/or rotated around the hinge and/or joint, but it has not yet been expanded. In FIG. 11, the lower display section is entirely underneath the upper display section. In FIG. 12, the lower display section has slid out from underneath the upper display section, thereby expanding the overall visible size of the display.

In addition to the lower display section, FIGS. 11 and 12 show a wearable device with an expandable display in a first configuration comprising: (a) a wearable device 201 which is configured to be worn around at least three-quarters of the circumference of a person's wrist and/or lower arm, wherein a dorsal portion of the device is configured to be worn on a dorsal quarter of the circumference of the person's wrist and/or lower arm, wherein a ventral portion of the device is configured to be worn on at least part of the ventral quarter of the circumference of the person's wrist and/or lower arm, wherein a first lateral portion of the device is configured to be worn on a first lateral quarter of the circumference of the person's wrist and/or lower arm between the dorsal quarter and the ventral quarter, wherein a second lateral portion of the device is configured to be worn on a second lateral quarter of the circumference of the person's wrist and/or lower arm between the dorsal quarter and the ventral quarter, wherein the second lateral quarter is opposite the first lateral quarter; (b) a first light-emitting display 202 on the wearable device, wherein the portion of the device on which the greatest percentage of the first light-emitting display is located is the dorsal portion; and (c) a second light-emitting display 204 on the wearable device, wherein the second light-emitting display has a first configuration in which the portion of the device on which the greatest percentage of the second light-emitting display is located is the first lateral portion or the second lateral portion and the second light-emitting display is a first size, and wherein the second light-emitting display has a second configuration in which the portion of the device on which the greatest percentage of the second light-emitting display is located is the dorsal portion and the second light-emitting display is a second size, and wherein the second size is greater than the first size. This example also includes a hinge and/or movable joint 203 around which the second display is flipped, pivoted, and/or rotated from the first configuration to the second configuration. Relevant device variations discussed elsewhere in this disclosure or in priority-linked disclosures can be applied to the example shown in this figure.

Figure 13:
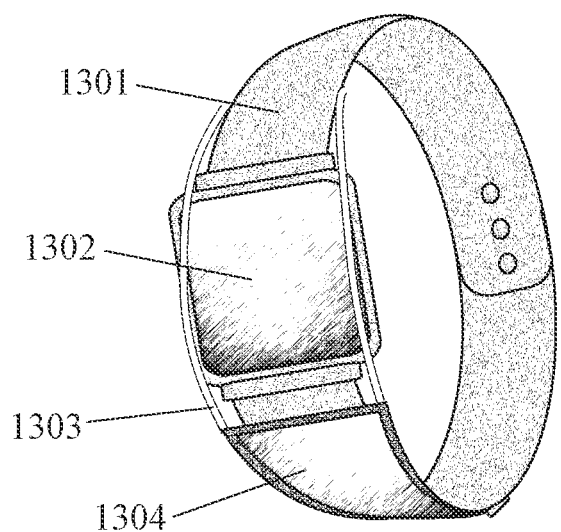
FIGS. 13 through 15 show three sequential views of a wearable device with a display which slides along tracks onto the dorsal portion of the device and is then expanded.
Figure 14:
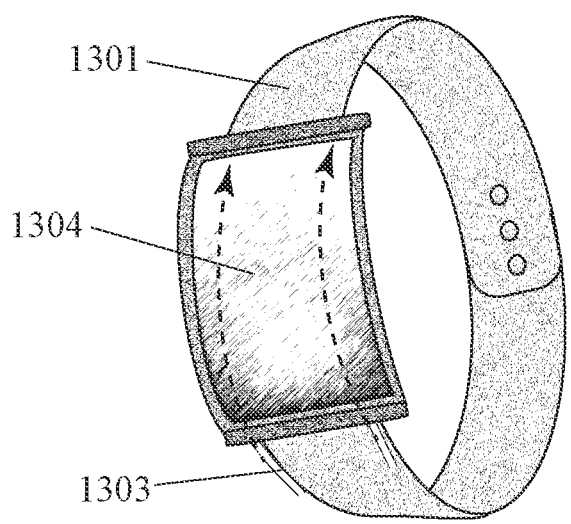
Figure 15:
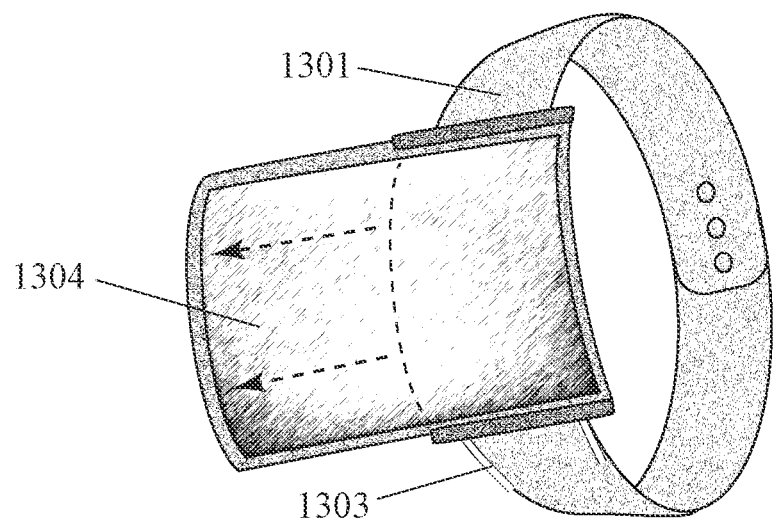

FIGS. 13 through 15 show another example of how this invention can be embodied in a wearable device with an expandable display. In this example, a second display slides around part of the circumference of the device, from a lateral portion to a dorsal portion, before being expanded. FIG. 13 shows the second display on a lateral portion of the device. FIG. 14 shows the second display sliding along tracks 1303 from the lateral portion to the dorsal portion of the device. FIG. 15 shows this second display being expanded.

FIGS. 13 through 15 show three oblique side views, at three different times, of an example of a wearable device with an expandable display comprising: (a) a wearable device which is configured to be worn around at least three-quarters of the circumference of a person's wrist and/or lower arm, wherein a dorsal portion of the device is configured to be worn on a dorsal quarter of the circumference of the person's wrist and/or lower arm, wherein a ventral portion of the device is configured to be worn on at least part of the ventral quarter of the circumference of the person's wrist and/or lower arm, wherein a first lateral portion of the device is configured to be worn on a first lateral quarter of the circumference of the person's wrist and/or lower arm between the dorsal quarter and the ventral quarter, wherein a second lateral portion of the device is configured to be worn on a second lateral quarter of the circumference of the person's wrist and/or lower arm between the dorsal quarter and the ventral quarter, wherein the second lateral quarter is opposite the first lateral quarter; (b) a first light-emitting display on the wearable device, wherein the portion of the device on which the greatest percentage of the first light-emitting display is located is the dorsal portion; and (c) a second light-emitting display on the wearable device, wherein the second light-emitting display has a first configuration in which the portion of the device on which the greatest percentage of the second light-emitting display is located is the first lateral portion or the second lateral portion and the second light-emitting display is a first size, and wherein the second light-emitting display has a second configuration in which the portion of the device on which the greatest percentage of the second light-emitting display is located is the dorsal portion and the second light-emitting display is a second size, and wherein the second size is greater than the first size.

With respect to specific components, FIGS. 13 through 15 show three oblique side views, at three different times, of a wearable device with an expandable display comprising: (a) a wearable device 1301 which is configured to be worn around at least three-quarters of the circumference of a person's wrist and/or lower arm, wherein a dorsal portion of the device is configured to be worn on a dorsal quarter of the circumference of the person's wrist and/or lower arm, wherein a ventral portion of the device is configured to be worn on at least part of the ventral quarter of the circumference of the person's wrist and/or lower arm, wherein a first lateral portion of the device is configured to be worn on a first lateral quarter of the circumference of the person's wrist and/or lower arm between the dorsal quarter and the ventral quarter, wherein a second lateral portion of the device is configured to be worn on a second lateral quarter of the circumference of the person's wrist and/or lower arm between the dorsal quarter and the ventral quarter, wherein the second lateral quarter is opposite the first lateral quarter; (b) a first light-emitting display 1302 on the wearable device, wherein the portion of the device on which the greatest percentage of the first light-emitting display is located is the dorsal portion; and (c) a second light-emitting display 1304 on the wearable device, wherein the second light-emitting display has a first configuration in which the portion of the device on which the greatest percentage of the second light-emitting display is located is the first lateral portion or the second lateral portion and the second light-emitting display is a first size, and wherein the second light-emitting display has a second configuration in which the portion of the device on which the greatest percentage of the second light-emitting display is located is the dorsal portion and the second light-emitting display is a second size, and wherein the second size is greater than the first size. This example also includes tracks 1303 along which the second display slides from the first configuration to the second configuration.

In an example, a second display slides around part of the circumference of a device along tracks (e.g. tracks, channels, or grooves). In an example, a device can have two parallel tracks along which a second display slides. In an example, a second display can have protrusions (e.g. prongs, knobs, bulbs, hooks, or balls) which protrude into the tracks (e.g. tracks, channels, or grooves), holding the second display snuggly on the device as the display slides around part of the circumference of the device. In an example, the display can be manually slid along the tracks. In another example, the display can be automatically slid along the tracks by an electromagnetic actuator. Relevant device variations discussed elsewhere in this disclosure or in priority-linked disclosures can be applied to the example shown in this figure.

Figure 16:
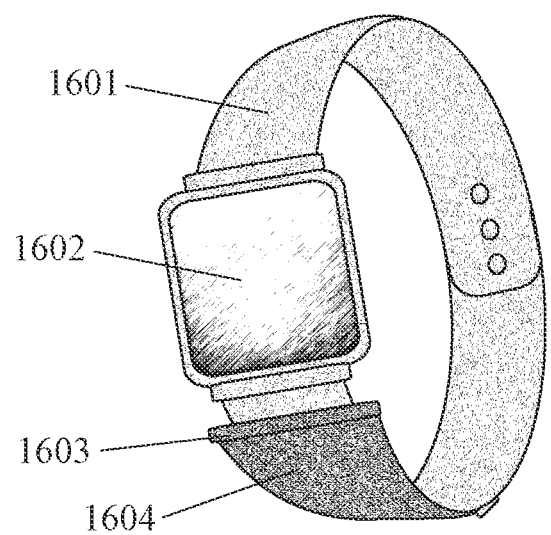
FIGS. 16 through 18 show three sequential views of a wearable device with a display which flips onto the dorsal portion of the device and is then expanded in two directions.
Figure 17:
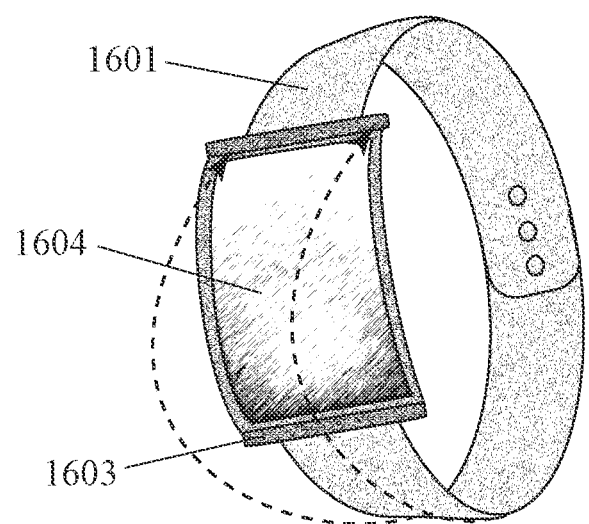
Figure 18:
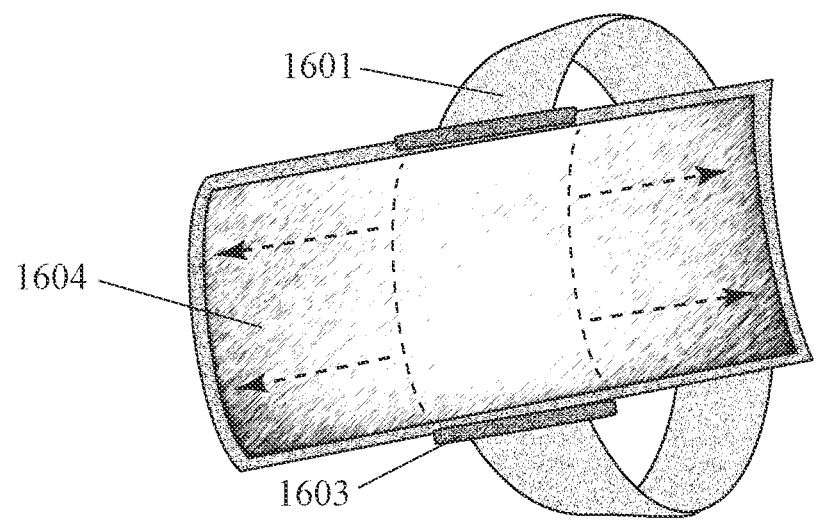

FIGS. 16 through 18 show another example of how this invention can be embodied in a wearable device with an expandable display. In this example, a second display is expanded in two directions. FIG. 16 shows the second display on a lateral portion of the device. FIG. 17 shows the second display being flipped, pivoted, and/or rotated from the lateral portion to the dorsal portion of the device. FIG. 18 shows this second display being expanded in two directions.

FIGS. 16 through 18 show three oblique side views, at three different times, of an example of a wearable device with an expandable display comprising: (a) a wearable device which is configured to be worn around at least three-quarters of the circumference of a person's wrist and/or lower arm, wherein a dorsal portion of the device is configured to be worn on a dorsal quarter of the circumference of the person's wrist and/or lower arm, wherein a ventral portion of the device is configured to be worn on at least part of the ventral quarter of the circumference of the person's wrist and/or lower arm, wherein a first lateral portion of the device is configured to be worn on a first lateral quarter of the circumference of the person's wrist and/or lower arm between the dorsal quarter and the ventral quarter, wherein a second lateral portion of the device is configured to be worn on a second lateral quarter of the circumference of the person's wrist and/or lower arm between the dorsal quarter and the ventral quarter, wherein the second lateral quarter is opposite the first lateral quarter; (b) a first light-emitting display on the wearable device, wherein the portion of the device on which the greatest percentage of the first light-emitting display is located is the dorsal portion; and (c) a second light-emitting display on the wearable device, wherein the second light-emitting display has a first configuration in which the portion of the device on which the greatest percentage of the second light-emitting display is located is the first lateral portion or the second lateral portion and the second light-emitting display is a first size, and wherein the second light-emitting display has a second configuration in which the portion of the device on which the greatest percentage of the second light-emitting display is located is the dorsal portion and the second light-emitting display is a second size, and wherein the second size is greater than the first size.

With respect to specific components, FIGS. 16 through 18 show three oblique side views, at three different times, of a wearable device with an expandable display comprising: (a) a wearable device 1601 which is configured to be worn around at least three-quarters of the circumference of a person's wrist and/or lower arm, wherein a dorsal portion of the device is configured to be worn on a dorsal quarter of the circumference of the person's wrist and/or lower arm, wherein a ventral portion of the device is configured to be worn on at least part of the ventral quarter of the circumference of the person's wrist and/or lower arm, wherein a first lateral portion of the device is configured to be worn on a first lateral quarter of the circumference of the person's wrist and/or lower arm between the dorsal quarter and the ventral quarter, wherein a second lateral portion of the device is configured to be worn on a second lateral quarter of the circumference of the person's wrist and/or lower arm between the dorsal quarter and the ventral quarter, wherein the second lateral quarter is opposite the first lateral quarter; (b) a first light-emitting display 1602 on the wearable device, wherein the portion of the device on which the greatest percentage of the first light-emitting display is located is the dorsal portion; and (c) a second light-emitting display 1604 on the wearable device, wherein the second light-emitting display has a first configuration in which the portion of the device on which the greatest percentage of the second light-emitting display is located is the first lateral portion or the second lateral portion and the second light-emitting display is a first size, and wherein the second light-emitting display has a second configuration in which the portion of the device on which the greatest percentage of the second light-emitting display is located is the dorsal portion and the second light-emitting display is a second size, and wherein the second size is greater than the first size. This example also includes a hinge and/or joint 1603 around which the second display is flipped, pivoted, and/or rotated from the first configuration to the second configuration.

In this example, a second display is expanded in two directions. In this example, a second display is expanded in two opposite directions. In an example, a second display can be expanded in a first direction (from a person's wrist toward their elbow) and also expanded in a second opposite direction (from the person's wrist toward their fingers). In an example, a second display can be expanded in two directions which are both orthogonal to the plane of the circumference of the device. In an example, a second display can be expanded in two opposite directions which are both orthogonal to the plane of the circumference of the device.

In an example, a device can have two rollers (e.g. rollers, spools, cylinders, or pins) around which a second display is rolled (e.g. rolled, coiled, or wound). In an example, a device can have two rollers (e.g. rollers, spools, cylinders, or pins) around which two sides of a second display are rolled (e.g. rolled, coiled, or wound). In an example, one side of the display can be rolled (e.g. rolled, coiled, or wound) around a first roller and the opposite side of the display can be rolled (e.g. rolled, coiled, or wound) around a second roller.

In an example, the second display can be expanded in a first direction by being unrolled (e.g. unrolled, uncoiled, or unwound) from the first roller and expanded in a second direction by being unrolled (e.g. unrolled, uncoiled, or unwound) from the second roller. In an example, the two rollers can be parallel to each other. In an example, the two rollers can be moved farther apart from each other when the second display is expanded in two opposite directions.

In an example, a second display can be comprise three sections which overlap each other to a first extent in a first configuration and overlap each other to a second extend in a second configuration, wherein the second extent is less than the first extent. In an example, a second display can be comprise three sections which overlap each other to a first extent in a first (unexpanded) configuration and overlap each other to a second extend in a second (expanded) configuration, wherein the second extent is less than the first extent. In an example, a second display can be comprise three sections, wherein a first section is on top of second and third sections in a first (unexpanded) configuration and wherein the second and third section slide out from under the first section in a second (expanded) configuration.

In an example, a second display can be comprise three sections, wherein the majority of the surface areas of second and third sections are underneath a first section in a first (unexpanded) configuration and wherein the majority of the surface areas of the second and third sections are not underneath the first section in a second (expanded) configuration. In an example, a second display can be comprise three sections, wherein at least 75% of the surface areas of second and third sections are underneath a first section in a first (unexpanded) configuration and wherein at least 75% of the surface areas of the second and third sections are not underneath the first section in a second (expanded) configuration.

In an example, a second display can be comprise three sections, wherein at least 75% of the surface areas of second and third sections are hidden under a first section in a first (unexpanded) configuration and wherein at least 75% of the surface areas of the second and third sections are not hidden under the first section in a second (expanded) configuration. In an example, a second display can be comprise three sections, wherein at least 75% of the surface areas of second and third sections are hidden under a first section in a first (unexpanded) configuration, wherein at least 75% of the surface areas of the second and third sections are not hidden under the first section in a second (expanded) configuration, wherein the second section is moved in a first direction from the first configuration to the second configuration, wherein the third section is moved in a second direction from the first configuration to the second configuration, and wherein the second direction is opposite the first direction.

In an example, a second display can comprise a plurality of telescoping sections, wherein the telescoping sections overlap to a first extent in a first (unexpanded) configuration, overlap to a second extent in a second (expanded) configuration, and wherein the second extent is less than the first extent. In an example, a second display can comprise a plurality of sections, wherein the sections are not coplanar in a first (unexpanded) configuration and are coplanar in a second (expanded) configuration. Relevant device variations discussed elsewhere in this disclosure or in priority-linked disclosures can be applied to the example shown in this figure.

Figure 19:
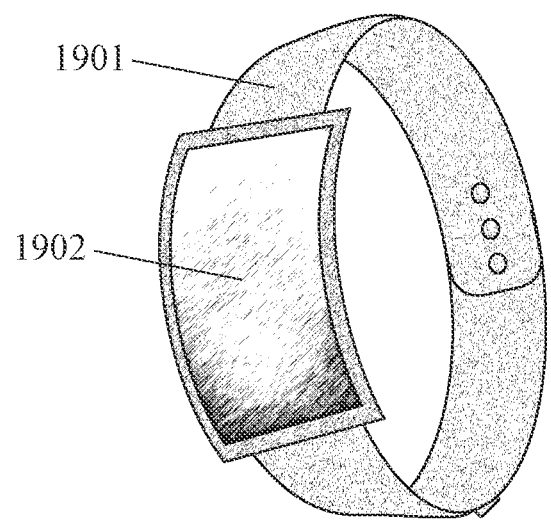
FIGS. 19 through 21 show three sequential views of a wearable device with a display on the dorsal portion of the device which is rotated and then expanded in two directions.
Figure 20:
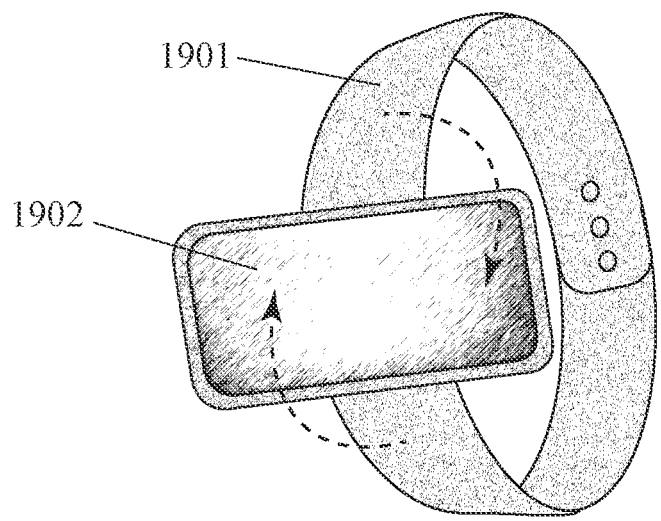
Figure 21:
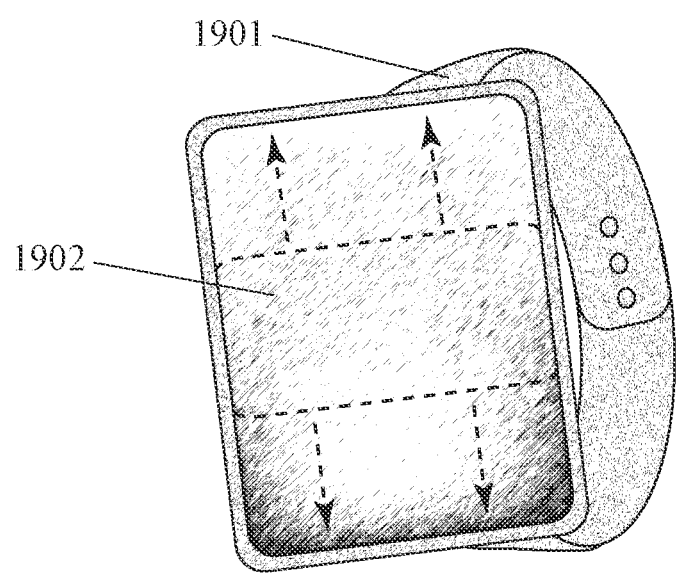

FIGS. 19 through 21 show another example of how this invention can be embodied in a wearable device with an expandable display. In this example, a display is rotated before being expanded. FIG. 19 shows a display in a first configuration with its longitudinal axis being parallel to the plane of the circumference of the device. FIG. 20 shows this display having been rotated so that its longitudinal axis is now orthogonal to the plane of the circumference of the device. FIG. 21 shows this display being expanded.

FIGS. 19 through 21 show three oblique side views, at three different times, of an example of a wearable device with an expandable display comprising: (a) a wearable device which is configured to be worn around at least three-quarters of the circumference of a person's wrist and/or lower arm, wherein a dorsal portion of the device is configured to be worn on a dorsal quarter of the circumference of the person's wrist and/or lower arm, wherein a ventral portion of the device is configured to be worn on at least part of the ventral quarter of the circumference of the person's wrist and/or lower arm, wherein a first lateral portion of the device is configured to be worn on a first lateral quarter of the circumference of the person's wrist and/or lower arm between the dorsal quarter and the ventral quarter, wherein a second lateral portion of the device is configured to be worn on a second lateral quarter of the circumference of the person's wrist and/or lower arm between the dorsal quarter and the ventral quarter, wherein the second lateral quarter is opposite the first lateral quarter; and (b) a light-emitting display, wherein the portion of the device on which the greatest percentage of the light-emitting display is located is the dorsal portion, wherein the light-emitting display has a longitudinal axis, wherein the light-emitting display has a first configuration in which the longitudinal axis is parallel to the plane of the circumference of the device and the light-emitting display is a first size, wherein the light-emitting display has a second configuration in which the which the longitudinal axis is orthogonal to the plane of the circumference of the device and the light-emitting display is a second size, and wherein the second size is greater than the first size.

With respect to specific components, FIGS. 19 through 21 show three oblique side views, at three different times, of an example of a wearable device with an expandable display comprising: (a) a wearable device 1901 which is configured to be worn around at least three-quarters of the circumference of a person's wrist and/or lower arm, wherein a dorsal portion of the device is configured to be worn on a dorsal quarter of the circumference of the person's wrist and/or lower arm, wherein a ventral portion of the device is configured to be worn on at least part of the ventral quarter of the circumference of the person's wrist and/or lower arm, wherein a first lateral portion of the device is configured to be worn on a first lateral quarter of the circumference of the person's wrist and/or lower arm between the dorsal quarter and the ventral quarter, wherein a second lateral portion of the device is configured to be worn on a second lateral quarter of the circumference of the person's wrist and/or lower arm between the dorsal quarter and the ventral quarter, wherein the second lateral quarter is opposite the first lateral quarter; and (b) a light-emitting display 1902 on the wearable device, wherein the portion of the device on which the greatest percentage of the light-emitting display is located is the dorsal portion, wherein the light-emitting display has a longitudinal axis, wherein the light-emitting display has a first configuration in which the longitudinal axis is parallel to the plane of the circumference of the device and the light-emitting display is a first size, wherein the light-emitting display has a second configuration in which the which the longitudinal axis is orthogonal to the plane of the circumference of the device and the light-emitting display is a second size, and wherein the second size is greater than the first size.

In this example, a display is rotated around its center before being expanded. In this example, a display is rotated around its central cross-sectional axis before being expanded. In another example, a display can be rotated around a non-central axis. In another example, a display can be rotated (e.g. rotated or pivoted) around an edge or vertex of the display. In this example, a display is rotated 90 degrees before being expanded. In an example, a display can be rotated between 40 and 140 degrees before being expanded. In another example, a display can be expanded before being rotated.

In an example, a display can have a longitudinal axis which is substantially orthogonal to the plane of the circumference of the device in a first configuration and can have a longitudinal axis which is substantially parallel to the plane of the circumference of the device in the second configuration. In another example, a display can have a longitudinal axis which is substantially parallel to the plane of the circumference of the device in a first configuration and can have a longitudinal axis which is substantially orthogonal to the plane of the circumference of the device in the second configuration.

In this example, a second display is expanded in two directions. In this example, a second display is expanded in two opposite directions. In an example, a second display can be expanded in two directions which are both parallel to the plane of the circumference of the device. In an example, a second display can be expanded in two opposite directions which are both parallel to the plane of the circumference of the device. In another example, a second display can be expanded in two directions which are both orthogonal to the plane of the circumference of the device. In another example, a second display can be expanded in two opposite directions which are both orthogonal to the plane of the circumference of the device. In an alternative example, a second display can be expanded in only one direction.

In this example, a display is on the dorsal portion of a device in both its first and second configurations. In another example, a display can be on a lateral portion of the device in both its first and second configurations. As yet another alternative, a display can be on a ventral portion of the device in both its first and second configurations. In another example, a display can be moved from one portion of a device to another portion of the device before being rotated and expanded. Relevant device variations discussed elsewhere in this disclosure or in priority-linked disclosures can be applied to the example shown in this figure.

Figure 22:
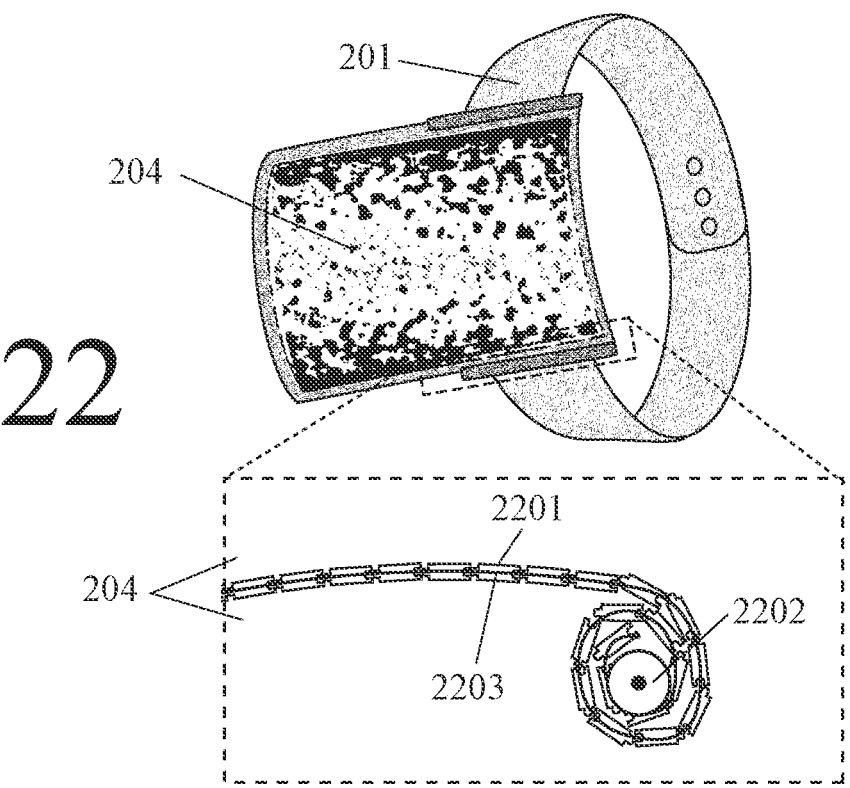
FIGS. 22 and 23 show two sequential views of a wearable device with a display comprising flexibly-connected segments, wherein the display is made less flexible (i.e. more rigid) by decreasing spacing between the segments.
Figure 23:
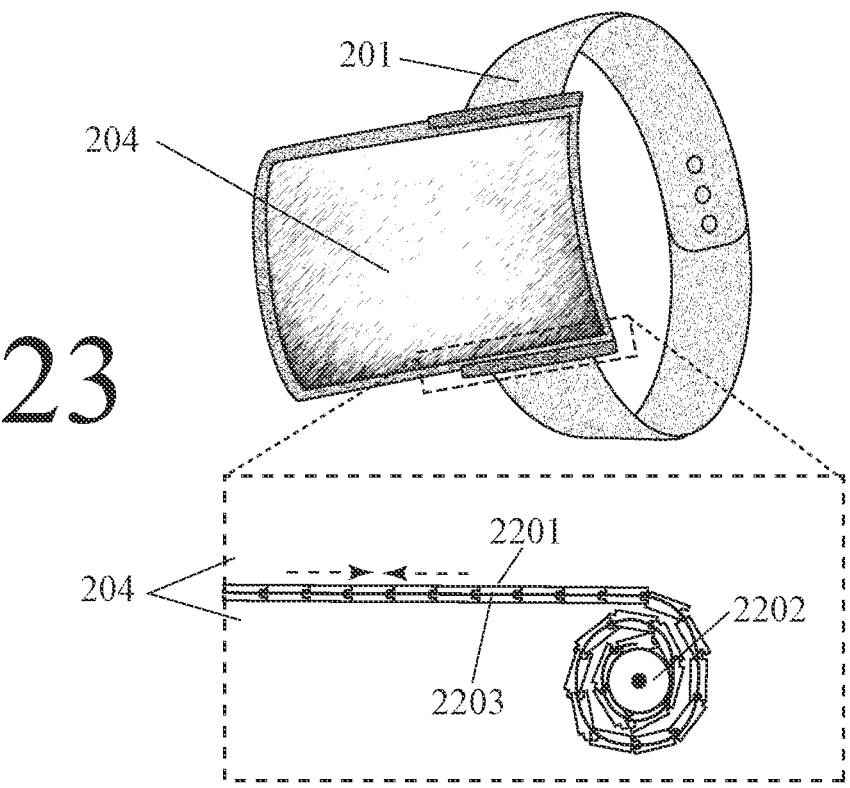

FIGS. 22 and 23 show an example of a wearable device 201 with a display 204 whose flexibility can be adjusted. In this example, the display 204 is comprised of a plurality of flexibly-connected segments 2201 which are connected by filaments, wires, or strings 2203. The flexibility of the display is adjusted by changing the tension (and/or length) of these filaments, wires, or strings and thereby changing the spacing between these segments. FIG. 22 shows the display in a first (flexible) configuration, wherein there is a larger average distance between flexibly-connected segments, thereby making the display more flexible. FIG. 23 shows the display in a second (rigid) configuration, wherein there is a shorter average distance between flexibly-connected segments, thereby making the display more rigid. In this example, the display is partially rolled (e.g. rolled, coiled, and/or wound) around a roller 2202.

The upper portion of FIG. 22 shows an oblique side view of the device in a first (flexible) configuration. The lower portion of FIG. 22 shows a dotted-line rectangle which contains a close-up cross-sectional view of the display, including a plurality of flexibly-connected segments and a roller around which one side of the display is rolled (e.g. rolled, coiled, and/or wound). The upper portion of FIG. 23 shows an oblique side view of this device in a second (rigid) configuration. The lower portion of FIG. 23 shows a dotted-line rectangle which contains a close-up cross-sectional view of the display, including a plurality of flexibly-connected segments and a roller around which one side of the display is rolled (e.g. rolled, coiled, and/or wound).

There are advantages and disadvantages to a having a wearable display be flexible. Advantages of having a wearable display be flexible include: being able to change the shape of the display so that it can be more easily moved from one location on the device to another location on the wearable device; and being able to roll or unroll the display. Disadvantages of having a wearable be flexible include: distortion of images on an uneven (e.g. uneven, wavy, non-flat) surface; and lack of uniform resistance for use of the display as a touch screen.

Having a display whose degree of flexibility can be selectively adjusted can provide the advantages of having a wearable display be flexible without the disadvantages thereof. In an example, a second display can be made (temporarily) flexible at a first time so that its shape can be changed, so that it can be moved from one location on a device to another location on the device, and/or so that it can be expanded. In an example, the flexibility of a second display can be adjusted so that it can be made more flexible (to transition from one shape to another). In an example, a second display can be made (temporarily) rigid at a second time so that its shape is fixed, so that it stays flat, and/or so that it can be used as a touch screen. In an example, a second display can be made less flexible (so that it can be stabilized in a selected shape for use as a touch screen).

In an example, a second display can comprise a plurality of flexibly-connected segments. When the segments are sufficiently small relative to the overall display, the overall display can be relatively flexible, bendable, and rollable. In an example, a display can comprise between 20 and 60 flexibly-connected segments. In an example, a display can comprise between 50 and 100 flexibly-connected segments. In an example, a second display can comprise a plurality of rectangular segments which are flexibly connected along their longitudinal (longer) sides. In an example, a second display can comprise a plurality of parallel rectangular segments which are flexibly connected along their longitudinal (longer) sides. In an example, a second display can comprise a plurality of flexibly-connected hexagonal segments.

In an example, the spacing between flexibly-connected segments comprising a display can be changed (e.g. adjusted) in order to change (e.g. adjust) the flexibility and/or rigidity of the display. In an example, a second display can comprise a plurality of adjustably-connected segments so that the flexibility of the second display can be adjusted. In an example, a second display can have a layer of adjustably-connected segments so that the flexibility of the second display can be adjusted. In an example, when flexibly-connected segments are farther apart from each other, then the display becomes more flexible, less rigid, more bendable, and/or more rollable, but when flexibly-connected segments are closer together, then the display becomes less flexible, more rigid, less bendable, and/or less rollable.

In an flexibly-connected segments can be connected to each other by filaments, wires, cables, chains, springs, strings, and/or threads. In an example, spacing between the segments can be adjusted by adjusting the tension of the filaments, wires, cables, chains, springs, strings, and/or threads. In an example, the flexibility of a display which comprises a plurality of flexibly-connected segments can be adjusted by adjusting the tension of filaments, wires, cables, chains, springs, strings, and/or threads which connect the flexibly-connected segments.

In an example, a second display can comprise a plurality of adjustably-connected segments with interdigitated protrusions and recesses so that the flexibility of the second display can be adjusted. In an example, a second display can comprise a plurality of adjustably-connected tongue-and-groove segments with interdigitated protrusions and recesses so that the flexibility of the second display can be adjusted. In an example, a second display can comprise a plurality of rectangular adjustably-connected tongue-and-groove segments with interdigitated protrusions and recesses so that the flexibility of the second display can be adjusted.

In an example, segments in a plurality of adjustably-connected segments can be shaped like tongue-and-groove floor boards, wherein a protrusion on a side of a first segment fits into a recess on a side of an adjacent second segment when the two segments are pushed (or pulled) close together. Unlike floor boards which are pushed together (e.g. by the lateral force of a hammer) into a permanently-interdigitated configuration, segments in a second display can be reversibly pulled (or pushed) closer together or father apart. When these segments are pulled (or pushed) closer together, they interlock and the display becomes more rigid. When these segments are pulled (or pushed) farther apart, they detach from each other and the display becomes more flexible. In an example, these segments can be connected by filaments, wires, and/or strings, wherein increasing the tension (and/or decreasing the length) of the filaments, wires, and/or strings pulls the segments closer together and decreasing the tension (and/or increasing the length) of the filaments, wires, and/or strings moves the segments farther apart.

In an example, a second display can comprise a plurality of adjustable-connected segments (e.g. tongue-and-groove segments) which enable the bendability of the second display to be adjusted. In an example, a second display can comprise a plurality of adjustable-connected segments (e.g. tongue-and-groove segments) with interdigitated protrusions and recesses so that the bendability of the second display can be adjusted. In an example, a second display can made with an electroactive polymer so that the bendability of the second display can be adjusted by application of electrical (and/or electromagnetic) energy.

In an example, a second display can comprise a plurality of adjustable-connected segments (e.g. tongue-and-groove segments) so that it can be rolled, coiled, and/or wound around a roller (e.g. roller, spool, cylinder, rod, or pin). In an example, the tension of longitudinal elements which connect the segments can be decreased so that the second display becomes more flexible in order to be rolled, coiled, and/or wound around a roller (e.g. roller, spool, cylinder, rod, or pin). In an example, the tension of longitudinal elements which connect the segments can be increased relaxed so that the second display becomes more rigid in order to display a flat image and serve as a touch screen.

In an example, the flexibility and/or rigidity of the second display can be changed. In an example, the second display can be made more flexible to facilitate moving it from its first configuration to its second configuration, but can then be made more rigid to facilitate a stable, flat image (and/or its use as a touch screen). In an example, a second display can further comprise (a layer of) a plurality of narrow rigid connected sections, wherein the second display becomes more flexible (less rigid) when the sections are more loosely connected to each other and the second display becomes more rigid (less flexible) when the sections are more tightly connected to each other. In an example, the degree to which sections are loosely or tightly connected to each other can be adjusted. In an example, the degree to which sections are loosely or tightly connected to each other can be adjusting the tension of one or more filaments, wires, or strings which connect the sections to each other. In an example, narrow rigid connected sections can have "tongue-and-grove" shapes, wherein a protrusion on an end of section fits into a recess on an end of a neighboring section when the sections are pulled close together. In this manner, the second display be flexible for changing configuration (including possibly changing curvature), but can be made into a relatively flat, rigid surface for use as a flat, rigid touch screen in its expanded configuration.

In an example, a (bottom) layer of a second display can comprise a plurality of connected "tongue-and-groove" segments which interlocking protrusions and recesses which fit into each other when they are pulled tightly together. In an example, the "tongue-and-groove" segments can be connected by filaments, wires, or strings. When the tension of the filaments, wires, or strings is decreased, then the layer (and the whole display) becomes less rigid, more flexible, and more arcuate. When the tension of the filaments, wires, or strings is increased, then the layer (and the whole display) becomes more rigid, less flexible, and more flat. Relevant device variations discussed elsewhere in this disclosure or in priority-linked disclosures can be applied to the example shown in this figure.

Figure 24:
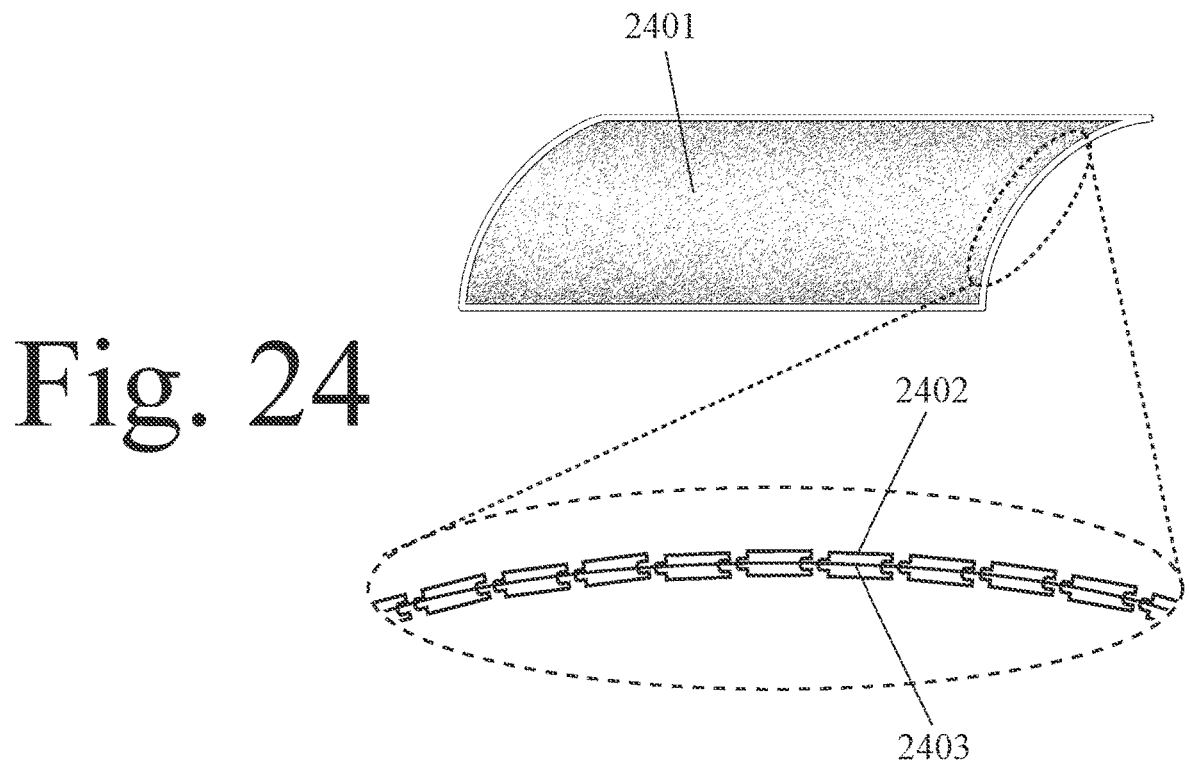
FIGS. 24 and 25 show a display comprising flexibly-connected segments, wherein the display is made flatter (and more rigid) by decreasing spacing between the segments.
Figure 25:
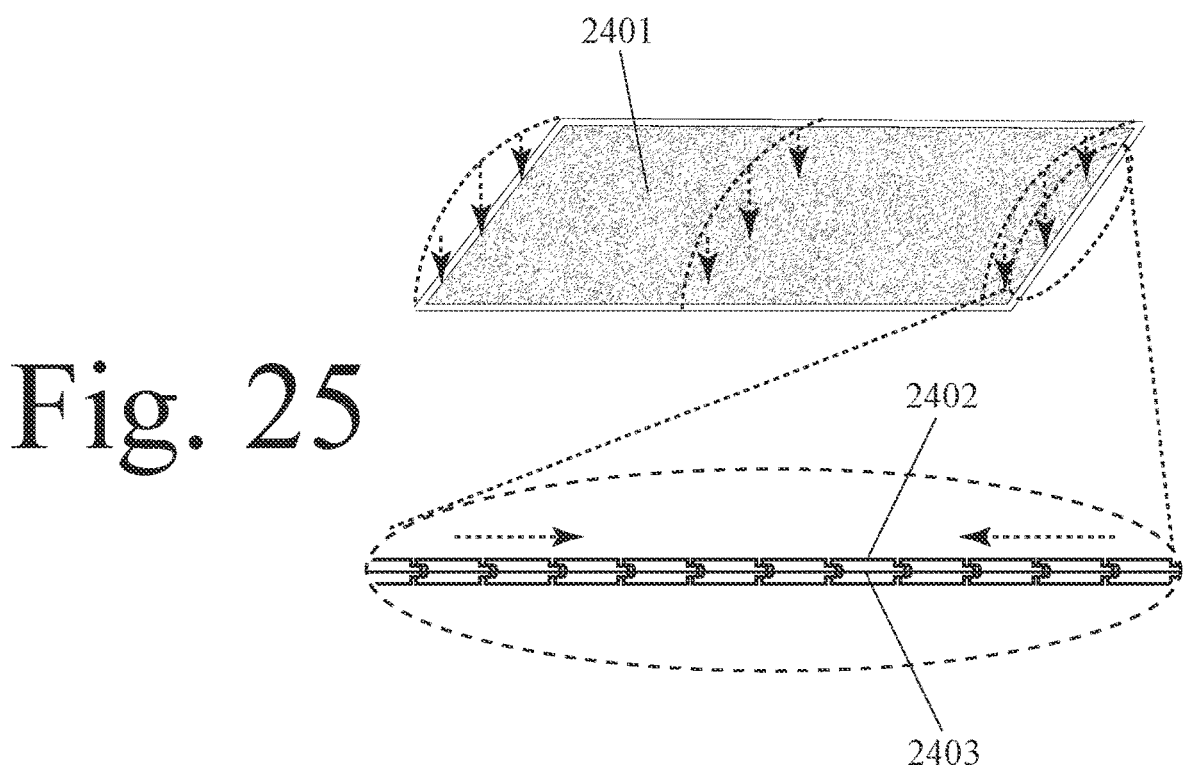

FIGS. 24 and 25 show an example of a display which can transition between a first configuration which is arcuate (and flexible) and a second configuration which is flat (and rigid). In this example, a display 2401 is comprised of a plurality of flexibly-connected interlocking segments 2402. These segments are connected by filaments, wires, or strings 2403. When the tension of the filaments, wires, or strings is increased (and/or they are shortened), then they pull the segments closer together and the display becomes flatter (and more rigid). FIG. 24 shows the display in a first configuration, wherein the tension between filaments, wires, or strings is lower (and/or they are longer), the segments are farther apart, and the display is more arcuate (and flexible). FIG. 25 shows the display in a second configuration, wherein the tension between filaments, wires, or strings is higher (and/or they are shorter), the segments are pulled closer together, and the display is more flat (and rigid).

The upper portion of FIG. 24 shows an oblique view of the display in its first configuration. The lower portion of FIG. 24 shows a dotted-line oval which contains a close-up cross-sectional view of the display in its first configuration. This close-up view shows that the segments which comprise the display are farther apart. This allows the display to be more flexible. The upper portion of FIG. 25 shows an oblique view of the display in its second configuration. The lower portion of FIG. 25 shows a dotted-line oval which contains a close-up cross-sectional view of the display in its second configuration. This close-up view shows that the segments which comprise the display are pulled together and interlock with each other. This makes the display more rigid.

There are advantages and disadvantages to a having a wearable display be flexible. Advantages of having a wearable display be flexible include: being able to change the shape of the display as it is moved from one location to another on a wearable device; and being able to expand the display by unrolling, unfolding, and/or unbending the display. Disadvantages of having a wearable be flexible include: distortion of images on an uneven (e.g. non-flat) surface; and lack of uniform resistance for use of the display as a touch screen.

In order to provide the advantages of having a wearable display be flexible without the disadvantages thereof, a wearable device can have a display whose flexibility can be changed (e.g. adjusted). In an example, the flexibility of a second display can be adjusted so that the display can be made more flexible (so that its shape can be changed) or can made be less flexible (so that it can serve as a touch screen). In an example, the flexibility of a second display can be adjusted so that it can be made more flexible (to transition from one shape to another) or can be made less flexible (so that it can be stabilized in a selected shape for use as a touch screen). In an example, the flexibility of a second display can be adjusted so that it can be made more flexible (to transition from an unexpanded size to an expanded size) and can be made less flexible (so that it can be stabilized in an expanded size for use as a touch screen).

In an example, a second display can comprise a plurality of flexibly-connected segments. When the segments are sufficiently small relative to the overall display, the overall display can be relatively flexible, bendable, and rollable. In an example, a display can comprise between 20 and 60 flexibly-connected segments. In an example, a display can comprise between 50 and 100 flexibly-connected segments. In an example, a second display can comprise a plurality of rectangular segments which are flexibly connected along their longitudinal (longer) sides. In an example, a second display can comprise a plurality of parallel rectangular segments which are flexibly connected along their longitudinal (longer) sides. In an example, a second display can comprise a plurality of flexibly-connected hexagonal segments.

In an example, the spacing between flexibly-connected segments comprising a display can be changed (e.g. adjusted) in order to change (e.g. adjust) the flexibility and/or rigidity of the display. In an example, a second display can comprise a plurality of adjustably-connected segments so that the flexibility of the second display can be adjusted. In an example, a second display can have a layer of adjustably-connected segments so that the flexibility of the second display can be adjusted. In an example, when flexibly-connected segments are farther apart from each other, then the display becomes more flexible, less rigid, more bendable, and/or more rollable, but when flexibly-connected segments are closer together, then the display becomes less flexible, more rigid, less bendable, and/or less rollable.

In an flexibly-connected segments can be connected to each other by filaments, wires, cables, chains, springs, strings, and/or threads. In an example, spacing between the segments can be adjusted by adjusting the tension of the filaments, wires, cables, chains, springs, strings, and/or threads. In an example, the flexibility of a display which comprises a plurality of flexibly-connected segments can be adjusted by adjusting the tension of filaments, wires, cables, chains, springs, strings, and/or threads which connect the flexibly-connected segments.

In an example, a second display can comprise a plurality of adjustably-connected segments with interdigitated protrusions and recesses so that the flexibility of the second display can be adjusted. In an example, a second display can comprise a plurality of adjustably-connected tongue-and-groove segments with interdigitated protrusions and recesses so that the flexibility of the second display can be adjusted.

In an example, a second display can comprise a plurality of rectangular adjustably-connected tongue-and-groove segments with interdigitated protrusions and recesses so that the flexibility of the second display can be adjusted.

In an example, segments in a plurality of adjustably-connected segments can be shaped like tongue-and-groove floor boards, wherein a protrusion on a side of a first segment fits into a recess on a side of an adjacent second segment when the two segments are pushed (or pulled) close together. Unlike floor boards which are pushed together (e.g. by the lateral force of a hammer) into a permanently-interdigitated configuration, segments in a second display can be reversibly pulled (or pushed) closer together or father apart. When these segments are pulled (or pushed) closer together, they interlock and the display becomes more rigid. When these segments are pulled (or pushed) farther apart, they detach from each other and the display becomes more flexible. In an example, these segments can be connected by filaments, wires, and/or strings, wherein increasing the tension (and/or decreasing the length) of the filaments, wires, and/or strings pulls the segments closer together and decreasing the tension (and/or increasing the length) of the filaments, wires, and/or strings moves the segments farther apart.

In an example, a second display can comprise a plurality of adjustable-connected segments (e.g. tongue-and-groove segments) which enable the bendability of the second display to be adjusted. In an example, a second display can comprise a plurality of adjustable-connected segments (e.g. tongue-and-groove segments) with interdigitated protrusions and recesses so that the bendability of the second display can be adjusted. In an example, a second display can made with an electroactive polymer so that the bendability of the second display can be adjusted by application of electrical (and/or electromagnetic) energy.

In an example, a second display can comprise a plurality of adjustable-connected segments (e.g. tongue-and-groove segments) so that it can be rolled, coiled, and/or wound around a roller (e.g. roller, spool, cylinder, rod, or pin). In an example, the tension of longitudinal elements which connect the segments can be decreased so that the second display becomes more flexible in order to be rolled, coiled, and/or wound around a roller (e.g. roller, spool, cylinder, rod, or pin). In an example, the tension of longitudinal elements which connect the segments can be increased relaxed so that the second display becomes more rigid in order to display a flat image and serve as a touch screen.

In an example, the flexibility and/or rigidity of the second display can be changed. In an example, the second display can be made more flexible to facilitate moving it from its first configuration to its second configuration, but can then be made more rigid to facilitate a stable, flat image (and/or its use as a touch screen). In an example, a second display can further comprise (a layer of) a plurality of narrow rigid connected sections, wherein the second display becomes more flexible (less rigid) when the sections are more loosely connected to each other and the second display becomes more rigid (less flexible) when the sections are more tightly connected to each other. In an example, the degree to which sections are loosely or tightly connected to each other can be adjusted. In an example, the degree to which sections are loosely or tightly connected to each other can be adjusting the tension of one or more filaments, wires, or strings which connect the sections to each other. In an example, narrow rigid connected sections can have "tongue-and-grove" shapes, wherein a protrusion on an end of section fits into a recess on an end of a neighboring section when the sections are pulled close together. In this manner, the second display be flexible for changing configuration (including possibly changing curvature), but can be made into a relatively flat, rigid surface for use as a flat, rigid touch screen in its expanded configuration.

In an example, a (bottom) fourth layer of a second display can comprise a plurality of connected "tongue-and-groove" segments which interlocking protrusions and recesses which fit into each other when they are pulled tightly together. In an example, the "tongue-and-groove" segments can be connected by filaments, wires, or strings. When the tension of the filaments, wires, or strings is decreased, then the fourth layer (and the whole display) becomes less rigid, more flexible, and more arcuate. When the tension of the filaments, wires, or strings is increased, then the fourth layer (and the whole display) becomes more rigid, less flexible, and more flat. Relevant device variations discussed elsewhere in this disclosure or in priority-linked disclosures can be applied to the example shown in this figure.

FIGS. 26 and 27 show another mechanism for adjusting the flexibility (and curvature) of a display. In this example, a display 2601 is made with an electroactive polymer and/or shape memory material which becomes rigid (and flat) when exposed to electrical energy 2602. FIG. 26 shows the display in a first configuration which is flexible and uneven, before exposure to electrical energy. FIG. 27 shows the display in a second configuration which is rigid and flat, after exposure to electrical energy.

The upper portion of FIG. 26 shows an oblique view of the display in its first configuration. The lower portion of FIG. 26 shows a dotted-line oval which contains a close-up cross-sectional view of the display in its first (uneven and flexible) configuration. The upper portion of FIG. 27 shows an oblique view of the display in its second configuration. The lower portion of FIG. 27 shows a dotted-line oval which contains a close-up cross-sectional view of the display in its second (flat and rigid) configuration. The second configuration can be better for displaying images and for using the display as a touch screen.

In an example, a display can made with an electroactive polymer. In an example, the flexibility of the display can be adjusted by application of electrical (and/or electromagnetic) energy to the polymer. In an example, a display can comprise a layer made with an electroactive polymer so that the flexibility of the display can be adjusted by application of electrical (and/or electromagnetic) energy to the polymer. In an example, this layer can become more flexible when electrical energy is applied to it. Alternatively, this layer can become more rigid when electrical energy is applied to it. In an example, a display can have a layer which is made with shape memory material. In an example, applying electrical energy to the shape memory material can make the display more flexible. Alternatively, applying electrical energy to the shape memory material can make the display more rigid.

In an example, a (layer of a) display can be made with a dielectric electroactive polymer, wherein applying electric energy and/or an electromagnetic field to the dielectric electroactive polymer changes the flexibility and/or shape of the display. In an example, a (layer of a) display can be made with a ferroelectric electroactive polymer, wherein applying electric energy and/or an electromagnetic field to the ferroelectric electroactive polymer changes the flexibility and/or shape of the display. In an example, a (layer of a) display can be made with a silicone or acrylic polymer, wherein applying electric energy and/or an electromagnetic field to the silicone or acrylic polymer changes the flexibility and/or shape of the display.

In an example, a (layer of a) display can be made with an ionic electroactive polymer, wherein applying electric energy and/or an electromagnetic field to the ionic electroactive polymer changes the flexibility and/or shape of the display. In an example, a (layer of a) display can be made with an ionic polymer-metal composite (IPMC), wherein applying electric energy and/or an electromagnetic field to the ionic polymer-metal composite (IPMC) changes the flexibility and/or shape of the display. In an example, a (layer of a) display can be made with polyvinylidene fluoride (PVDF), wherein applying electric energy and/or an electromagnetic field to the polyvinylidene fluoride (PVDF) changes the flexibility and/or shape of the display. Relevant device variations discussed elsewhere in this disclosure or in priority-linked disclosures can be applied to the example shown in this figure.

Figure 28:
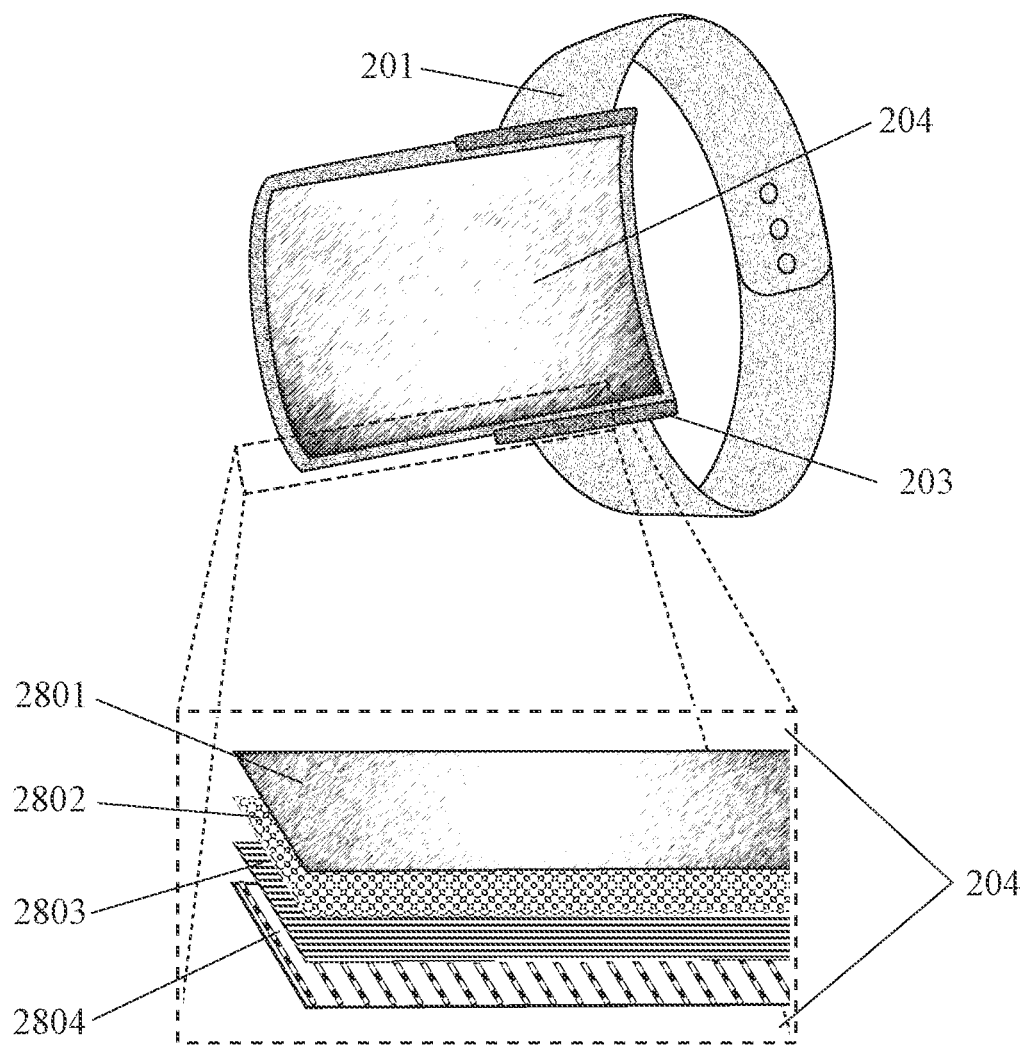
FIG. 28 shows a display with four layers: a protective layer; a light-emitting layer; an electroconductive layer; and a layer comprising flexibly-connected segments.

FIG. 28 shows an example of a display with a plurality of layers. The upper portion of FIG. 28 shows an oblique side view of a wearable device with an extended display. The lower portion of FIG. 28 shows a dotted-line rectangle which contains a close-up cross-sectional view of the display. In this example, a display 204 on a wearable device 201 has four layers. In this example, the (top) first layer 2801 is a flexible protective layer. The second layer 2802 comprises an array and/or matrix of light-emitters. The third layer 2803 comprises a plurality of electroconductive pathways which provide power to the light-emitters. The (bottom) fourth layer 2804 comprises a plurality of flexibly-connected segments.

In an example, the first layer can be a flexible but scratch-resistant polymer layer. In an example, this layer can be made with acrylonitrile butadiene styrene or high-density polyethylene. In an example, the second layer can comprise an array of light-emitting elements selected from the group consisting of: Light Emitting Diode (LED), Direct-Lit LED, Edge-Lit LED (ELED), Encapsulated LED, Micro-LED, Mini-LED, Monochromatic LED (MLED), Organic Light Emitting Diode (OLED), Quantum Dot LED (QLED), Resonant Cavity Light Emitting Diode (RCLED), Super-Luminescent Light Emitting Diode (SLED), and Tunable LED. In an example, the third layer can comprise flexible electroconductive pathways and/or circuits. In an example, these pathways and/or circuits can be made with a flexible polymer which has been doped and/or impregnated with electroconductive material.

In an example, the fourth layer can comprise a plurality of flexibly-connected segments. In an example, changing the spacing between segments in the fourth layer changes the overall flexibility and/or rigidity of the display. The fourth layer can be made less rigid, more flexible, and more arcuate to facilitate changing the configuration of the display, but can also be made more rigid, less flexible, and more flat to facilitate use of the display as a touch screen.

In an example, a fourth layer of a display can comprise a plurality of connected "tongue-and-groove" segments which interlocking protrusions and recesses which fit into each other when they are pulled tightly together. In an example, the "tongue-and-groove" segments can be connected by filaments, wires, or strings. When the tension of the filaments, wires, or strings is decreased, then the fourth layer (and the whole display) becomes less rigid, more flexible, and more arcuate. When the tension of the filaments, wires, or strings is increased, then the fourth layer (and the whole display) becomes more rigid, less flexible, and more flat.

In another example, a display can comprise at least three layers. A (top) first layer can be a flexible protective layer. A second layer can comprise an array and/or matrix of light-emitters and electroconductive pathways which provide power to the light-emitters. A third layer can comprise a plurality of flexibly-connected segments, wherein changing the spacing between the segments changes the overall flexibility and/or rigidity of the display. The third layer can be made less rigid, more flexible, and more arcuate to facilitate changing the configuration of the display, but can also be made more rigid, less flexible, and more flat to facilitate use of the display as a touch screen. Relevant device variations discussed elsewhere in this disclosure or in priority-linked disclosures can be applied to the example shown in this figure.

Figure 29:
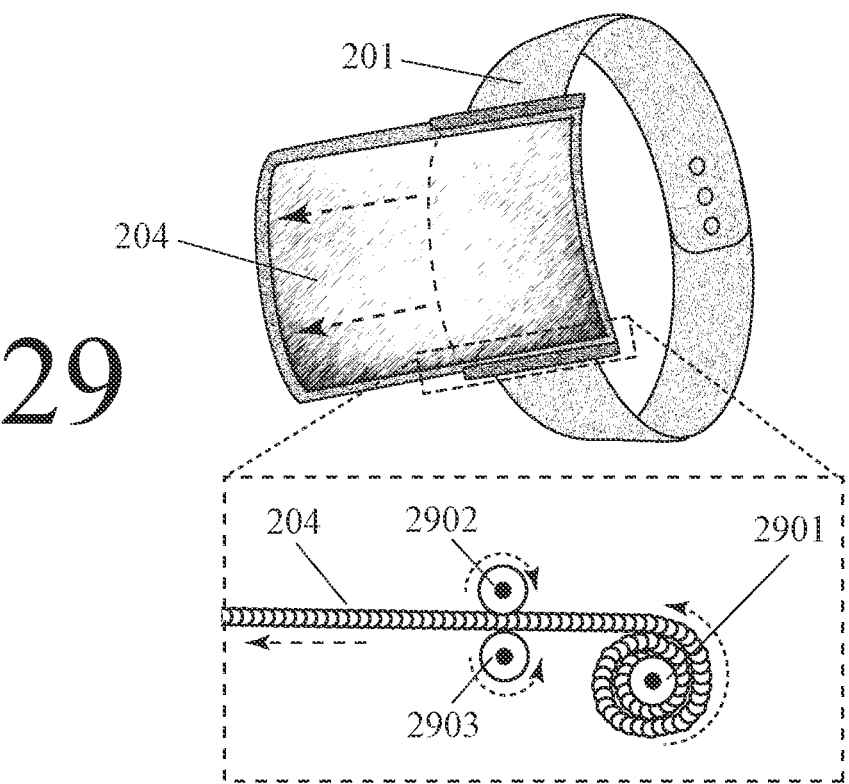
FIG. 29 shows a cross-sectional close-up view of an expandable display mechanism with guide rollers in addition to a primary roller.

FIG. 29 shows an example of how a display 204 on a wearable device 201 can be expanded by a roller mechanism. In this example, a roller mechanism includes more than one roller. In this example, a roller mechanism includes two guide rollers 2902 and 2903 (between which a flexible display passes) in addition to a primary roller 2901 (around which the display is rolled or from which the display is unrolled). The upper portion of FIG. 29 shows an oblique side view of the wearable device with the display. The lower portion of FIG. 29 shows a dotted-line rectangle which contains a close-up cross-sectional view of the roller mechanism.

In this example, one side of a flexible display is rolled (e.g. rolled, coiled, and/or wound) around a primary roller (e.g. roller, spool, cylinder, rod, or pin) to decrease the visible size of the display and is unrolled (e.g. unrolled, uncoiled, and/or unwound) from the primary roller (e.g. roller, spool, cylinder, rod, or pin) to increase the visible size of the display. FIG. 29 shows the display being unrolled from the primary roller. In this example, one side of a flexible display is rolled (e.g. rolled, coiled, and/or wound) around a primary roller to make the visible size of the display smaller (in an unexpanded first configuration) and is unrolled (e.g. unrolled, uncoiled, and/or unwound) from the primary roller to make the visible size of the display larger (in an expanded second configuration).

In this example, the flexible display passes (e.g. is threaded, slid, and/or compressed) between two guide rollers. In this example, the flexible display passes between two guide rollers before it is rolled (e.g. rolled, coiled, and/or wound) around the primary roller and after it has been unrolled (e.g. unrolled, uncoiled, and/or unwound) from the primary roller. In this example, two guide rollers rotate in opposite directions (e.g. one clockwise and the other counter-clockwise) as the display passes between them. In an example, guide rollers can help the display to roll evenly onto (or off from) the primary roller. In an example, guide rollers can help to maintain proper tension on the display. In an example, guide rollers can help to flatten the display. In an example, guide rollers can push together connected segments which comprise the display so that these segments interlock with each other.

In an example, guide rollers can have teeth (e.g. teeth, notches, and/or protrusions) which engage the display as the display passes between them. In an example, guide rollers can be rotated automatically by one or more electromagnetic actuators to actively pull the display as it passes between them. In an example, guide rollers can be gears. This example shows one roller mechanism on one side of a display. In an example, there can be two roller mechanisms, one on each side of the display. In an example, primary rollers in these two roller mechanisms can rotate in opposite (e.g. clockwise vs. counter-clockwise) directions as a flexible display is expanded. Relevant device variations discussed elsewhere in this disclosure or in priority-linked disclosures can be applied to the example shown in this figure.

Figure 30:
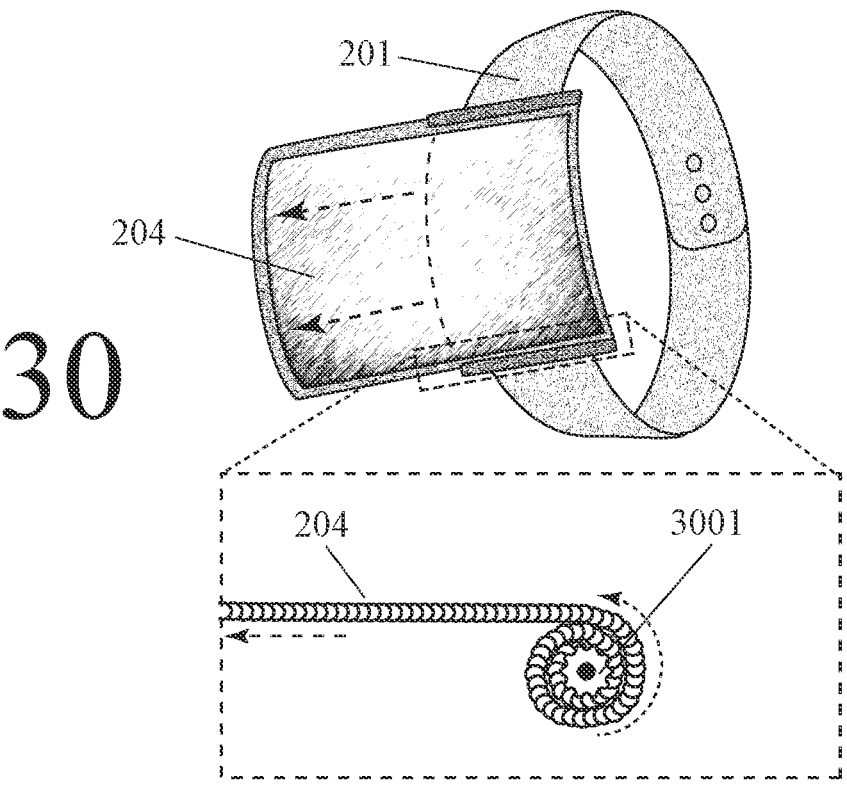
FIG. 30 shows a cross-sectional close-up view of an expandable display mechanism with a gear-type roller (e.g. with teeth and/or cogs).

FIG. 30 shows another example of how a display 204 on a wearable device 201 can be expanded by a roller mechanism. In this example, a roller 3001 has radial protrusions (e.g. like teeth on a gear) which engage the display. The upper portion of FIG. 30 shows an oblique side view of the wearable device with the display. The lower portion of FIG. 30 shows a dotted-line rectangle which contains a close-up cross-sectional view of the roller. FIG. 30 shows the display being unrolled (e.g. unrolled, uncoiled, and/or unwound) from the roller.

In this example, the roller has teeth (e.g. teeth, notches, and/or protrusions) which engage the display as the display is rolled around or unrolled from the roller. In an example, the roller can be rotated automatically by one or more electromagnetic actuators to actively engage (e.g. push or pull) the display. In an example, a roller can be embodied in one or more gears. This example shows one roller on one side of a display. In an example, there can be two rollers, one on each side of the display. In an example, these two rollers can rotate in opposite (e.g. clockwise vs. counter-clockwise) directions as a flexible display is expanded.

In an example, the lower surface and/or the lateral sides of a display can have protrusions or recesses (e.g. teeth, ridges, notches, or undulations) and a roller (e.g. roller, spool, cylinder, rod, or pin) around which the display is rolled, coiled, and/or wound can have recesses or protrusions (e.g. teeth, ridges, notches, or undulations) which are geometrically complementary to those of the display. In an example, the protrusions or recesses on the display can interdigitate (e.g. interdigitate, engage, and/or mesh) with the recesses or protrusions on the roller. In an example, a roller (e.g. roller, spool, cylinder, rod, or pin) can comprise a gear which engages protrusions or recesses (e.g. teeth, ridges, notches, or undulations) on the lower surface of a display. Relevant device variations discussed elsewhere in this disclosure or in priority-linked disclosures can be applied to the example shown in this figure.

Figure 31:
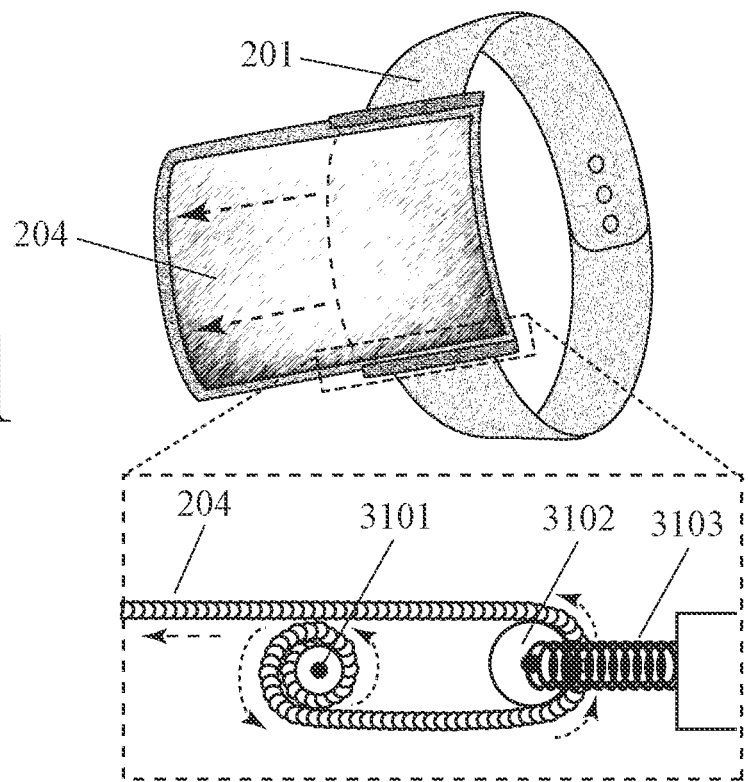
FIG. 31 shows a cross-sectional close-up view of an expandable display mechanism with a spring-bound roller to maintain tension on the display.

FIG. 31 shows another example of how a display 204 on a wearable device 201 can be expanded by a roller mechanism. This roller mechanism includes a spring to maintain tension on the display. In this example, a roller mechanism includes a spring 3103 attached to a guide roller 3102 in addition to a primary roller 3101. The spring-bound guide roller maintains tension on the display as the display is rolled or unrolled. The upper portion of FIG. 31 shows an oblique side view of the wearable device with the display. The lower portion of FIG. 31 shows a dotted-line rectangle which contains a close-up cross-sectional view of the roller mechanism. FIG. 31 shows the display being unrolled (e.g. unrolled, uncoiled, and/or unwound) from the roller. Relevant device variations discussed elsewhere in this disclosure or in priority-linked disclosures can be applied to the example shown in this figure.

Figure 32:
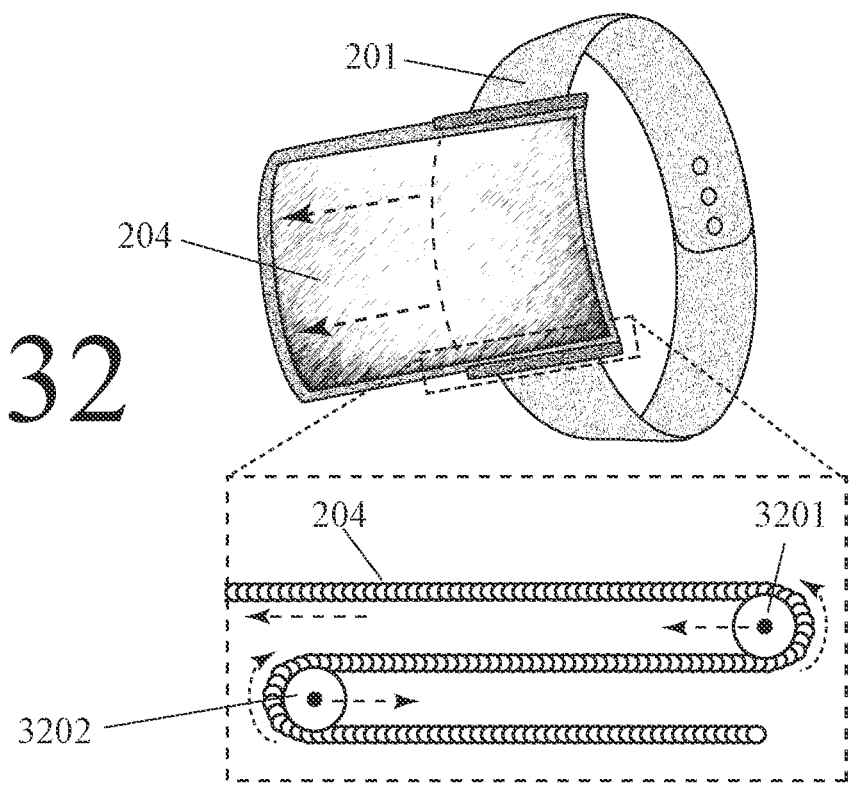
FIG. 32 shows a cross-sectional close-up view of an expandable display mechanism with a plurality of rollers around which the display loops.

FIG. 32 shows another example of how a display 204 on a wearable device 201 can be expanded by a roller mechanism. This roller mechanism includes a plurality of rollers 3201 and 3202 around which a flexible display is looped back and forth. The upper portion of FIG. 32 shows an oblique side view of the wearable device with the display. The lower portion of FIG. 32 shows a dotted-line rectangle which contains a close-up cross-sectional view of the roller mechanism. FIG. 32 shows the display being expanded (e.g. being extended out from the roller mechanism).

In this example, a display is looped between two or more rollers (e.g. rollers, spools, cylinders, rods, or pins). In an example, a display is looped back and forth between two or more rollers (e.g. rollers, spools, cylinders, rods, or pins). In an example, the distance between the two or more rollers (e.g. rollers, spools, cylinders, rods, or pins) can be changed. In an example, when the distance the two or more rollers is decreased, then the portion of the display which is looped between them decreases and the display extends outward from the roller mechanism. In an example, when the distance the two or more rollers is increased, then the portion of the display which is looped between them increases and the display is drawn into the roller mechanism.

In this example, a display is looped partially around a roller, but not coiled or wound entirely around the roller. In this example, a display overlaps itself to a first extent in a non-expanded configuration and overlaps itself to a second extent in an expanded configuration, wherein the second extent is less than the first extent. In this example, a display is looped back and forth twice between two rollers. In this example, a display is looped back and forth twice between two rollers, forming three portions: a first (upper) portion which extends out from a first (upper) roller 3201, a second (middle) portion which spans between the first (upper) roller and the second (lower) roller 3202, and a third (lower) portion which spans extends out from the third (lower) roller. In an example, these three portions of the display can be parallel to each other. In an example, as the two rollers are moved closer together, the first (upper) portion is increased and the second (middle) portion is decreased. Relevant device variations discussed elsewhere in this disclosure or in priority-linked disclosures can be applied to the example shown in this figure.

Figure 33:
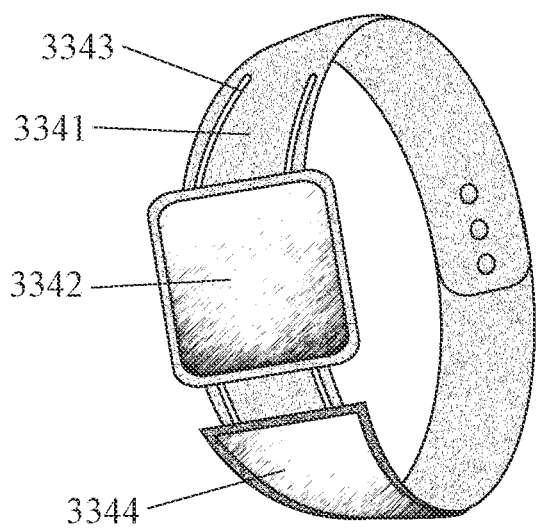
FIGS. 33 through 35 show three sequential views of a wearable device with two displays which slide along tracks.
Figure 34:
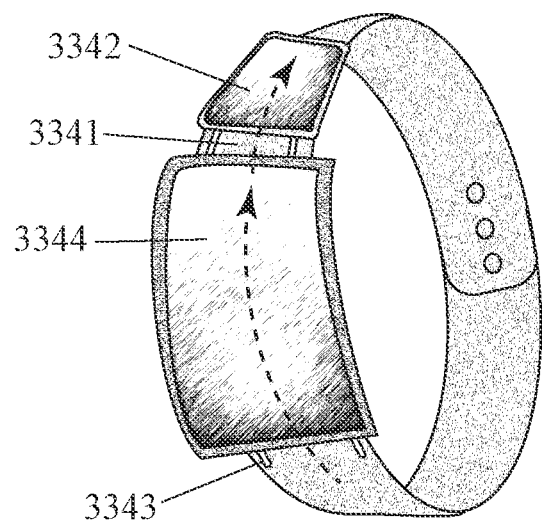
Figure 35:
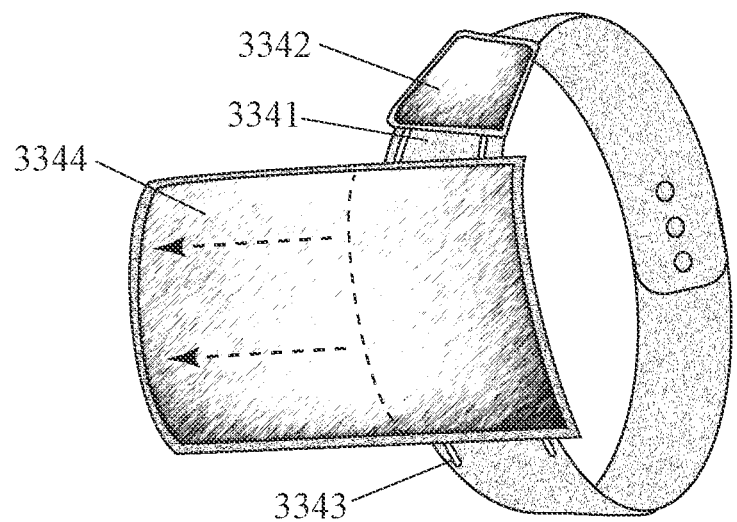

FIGS. 33 through 35 show another example of how this invention can be embodied in a wearable device with an expandable display. In this example, two displays slide around part of the circumference of the device and one of them is expanded. FIG. 33 shows this device 3341 when a first display 3342 is on a dorsal portion of the device and a second display 3344 is on a lateral portion of the device. FIG. 34 shows this device when the first display has been slid along tracks 3343 to a lateral portion of the device and the second display has been slid along these tracks to the dorsal portion of the display. FIG. 35 shows this device when the second display has been expanded.

In an example, the displays can slide around part of the circumference of a device along tracks (e.g. tracks, channels, or grooves). In an example, a device can have two parallel tracks along which the displays slide. In an example, the displays can have protrusions (e.g. prongs, knobs, bulbs, hooks, or balls) which protrude into the tracks (e.g. tracks, channels, or grooves), holding the displays snuggly on the device as they slide around part of the circumference of the device. In an example, the displays can be manually slid along the tracks. In another example, the displays can be automatically slid along the tracks by an electromagnetic actuator. Relevant device variations discussed elsewhere in this disclosure or in priority-linked disclosures can be applied to the example shown in this figure.

Figure 36:
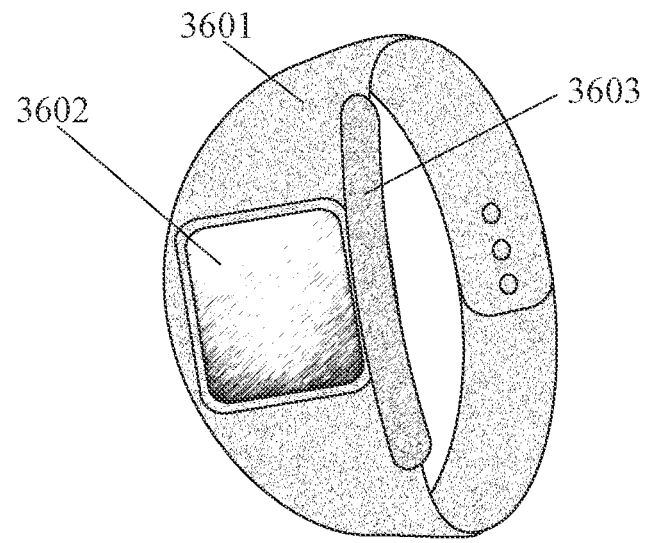
FIGS. 36 and 37 show two sequential views of a wearable device with a dorsal first display which does not expand and a dorsal second display which does expand, wherein the second display expands out over the first display.
Figure 37:
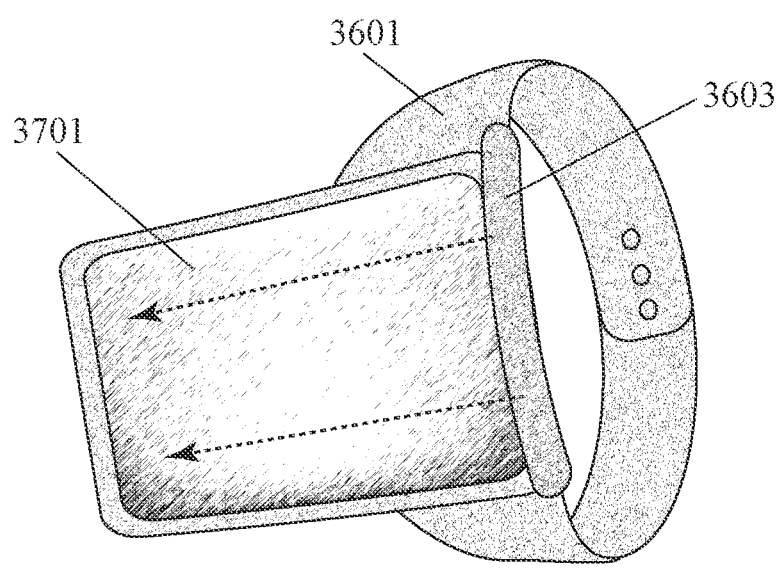

FIGS. 36 and 37 show another example of how this invention can be embodied in a wearable device with an expandable display. In this example, a second display extends out over a first display. FIG. 36 shows this device 3601 in a first configuration when a first display 3602 is visible and a second display 3701 is retracted within a housing 3603 which is next to (e.g. to one side of) the first display. FIG. 37 shows this device in a second configuration when the second display has been extended out from the housing and covers the first display.

In an example, the second display can be rolled (e.g. rolled, coiled, and/or wound) around a roller in the housing in a first configuration and unrolled (e.g. unrolled, uncoiled, and/or unwound) from that roller in a second configuration. In an example, the second display can be rolled (e.g. rolled, coiled, and/or wound) around a roller and contained in the housing in a first configuration. In an example, the second display can be unrolled (e.g. unrolled, uncoiled, and/or unwound) from that roller and extend out from the housing in a second configuration.

In an example, both the first and second displays can be primarily on the dorsal portion of the device. In an example, the housing that contains the second display can be on one side of the first device. In an example, the housing can have a longitudinal axis which is parallel to the plane of the circumference of the device. In an example, the housing can be larger than the closest side of the first display. In an example, the second display can be larger than the first display. Relevant device variations discussed elsewhere in this disclosure or in priority-linked disclosures can be applied to the example shown in this figure.

Figure 38:
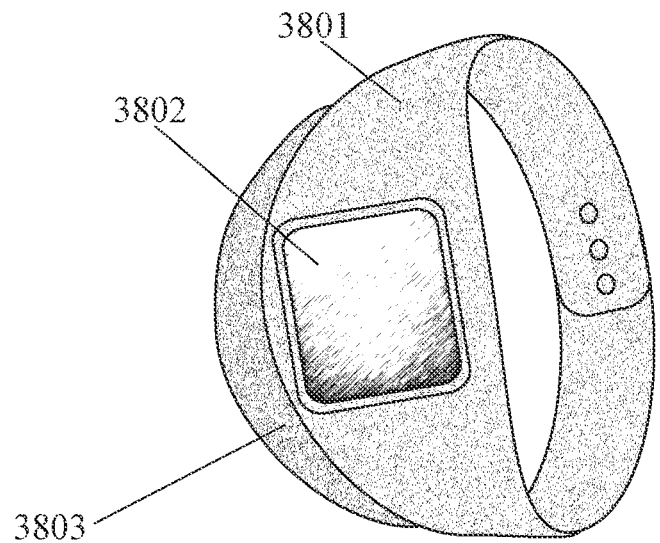
FIGS. 38 and 39 show two sequential views of a wearable device with a dorsal first display which does not expand and a dorsal second display which does expand, wherein the second display does not expand out over the first display.
Figure 39:
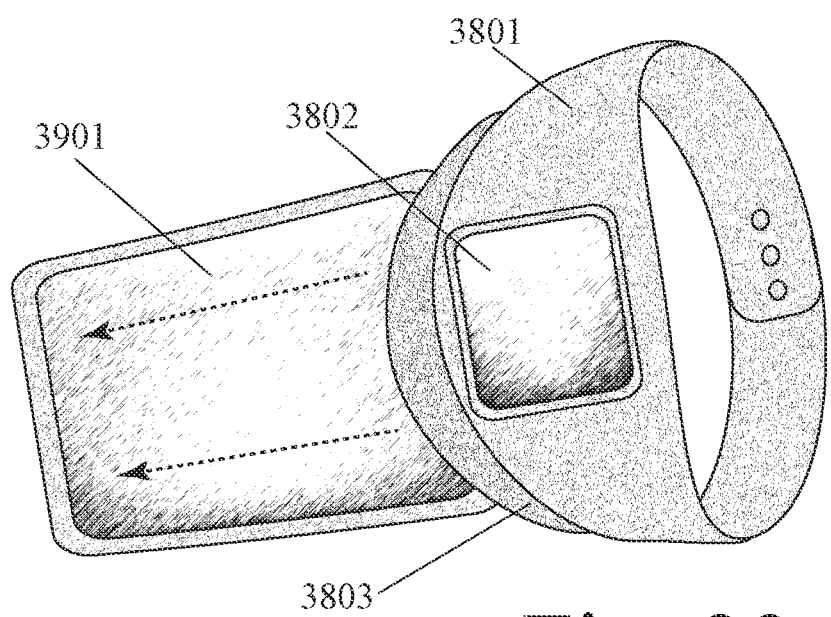

FIGS. 38 and 39 show another example of how this invention can be embodied in a wearable device with an expandable display. In this example, a second display extends out from the side of a first display, but does not cover the first display. FIG. 38 shows this device 3801 in a first configuration when a second display 3901 is retracted within a housing 3803. FIG. 39 shows this device in a second configuration when the second display has been extended out from the housing.

In an example, the second display can be rolled (e.g. rolled, coiled, and/or wound) around a roller in the housing in a first configuration and unrolled (e.g. unrolled, uncoiled, and/or unwound) from that roller in a second configuration. In an example, the second display can be rolled (e.g. rolled, coiled, and/or wound) around a roller and contained in the housing in a first configuration. In an example, the second display can be unrolled (e.g. unrolled, uncoiled, and/or unwound) from that roller and extend out from the housing in a second configuration.

In an example, both the first and second displays can be primarily on the dorsal portion of the device. In an example, the housing that contains the second display can be on one side of the first device. In an example, the housing can have a longitudinal axis which is parallel to the plane of the circumference of the device. In an example, the housing can be larger than the closest side of the first display. In an example, the second display can be larger than the first display. Relevant device variations discussed elsewhere in this disclosure or in priority-linked disclosures can be applied to the example shown in this figure.

Figure 40:
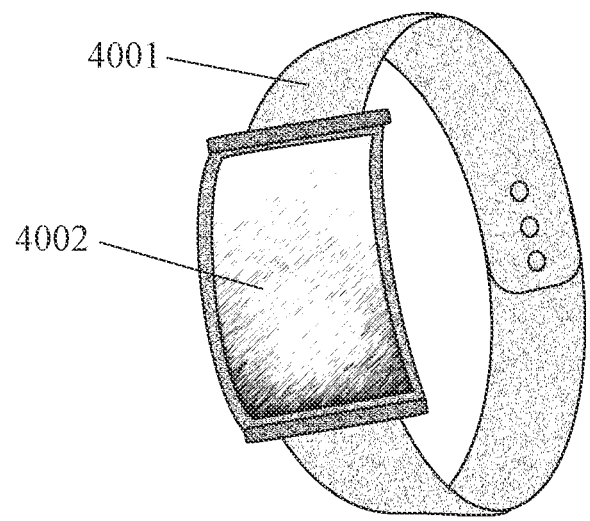
FIGS. 40 and 41 show two sequential views of a wearable device with only one display, wherein this display expands out from a dorsal portion of the device.
Figure 41:
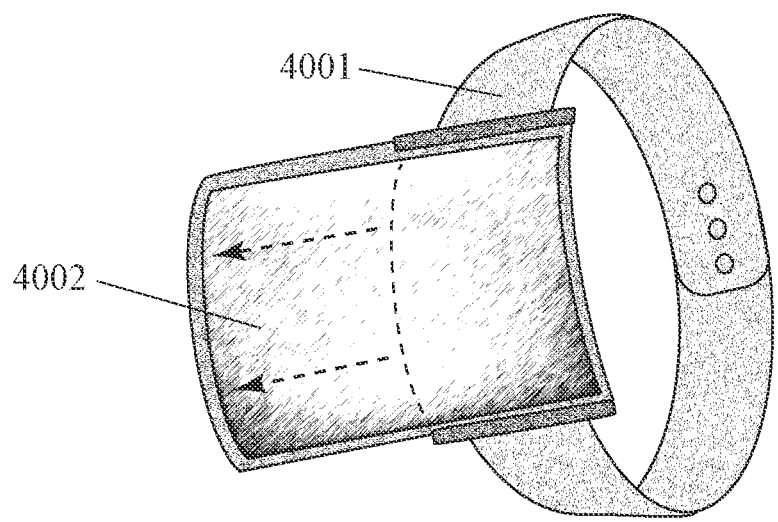

FIGS. 40 and 41 show another example of how this invention can be embodied in a wearable device with an expandable display. FIG. 40 shows this device 4001 when a display 4002 is in a first (unexpanded) configuration. FIG. 41 shows this device when the display is in a second (expanded) configuration.

FIGS. 40 and 41 show two oblique side views, at two different times, of an example of a wearable device with an expandable display comprising: (a) a wearable device which is configured to be worn around at least three-quarters of the circumference of a person's wrist and/or lower arm, wherein a dorsal portion of the device is configured to be worn on a dorsal quarter of the circumference of the person's wrist and/or lower arm, wherein a ventral portion of the device is configured to be worn on at least part of the ventral quarter of the circumference of the person's wrist and/or lower arm, wherein a first lateral portion of the device is configured to be worn on a first lateral quarter of the circumference of the person's wrist and/or lower arm between the dorsal quarter and the ventral quarter, wherein a second lateral portion of the device is configured to be worn on a second lateral quarter of the circumference of the person's wrist and/or lower arm between the dorsal quarter and the ventral quarter, wherein the second lateral quarter is opposite the first lateral quarter; and (b) a light-emitting display on the wearable device, wherein the portion of the device on which the greatest percentage of the display is located is the dorsal portion, wherein the display has a first configuration with a first visible size, wherein the display has a second configuration with a second visible size, and wherein the second size is greater than the first size.

In this example, a wearable device with an expandable display is embodied in the form of a smart watch. In various examples, a wearable device with an expandable display can be embodied in a form selected from the group consisting of: smart watch, fitness band, wristband, sleeve or cuff, bracelet or bangle, arm band, glucose monitor, identification band, and wearable phone.

In an example, a display can be flexible, bendable, and/or rollable. In an example, a display can be flexible, bendable, and/or rollable so that it can transition between unexpanded and expanded configurations without the display being damaged. In an example, a display can be flexible so that it can change between being flat (e.g. planar) and arcuate (e.g. curved) without the display being damaged. In an example, a display can be flexible so that it can change between flat, concave, and convex shapes. In an example, a display can be flexible so that it can change between flat, concave, or convex configurations.

In an example, a display can be manually moved from its first configuration to its second configuration. In an example, a display can be manually flipped, pulled, pushed, pressed, and/or slid from, its first configuration to its second configuration by the person wearing the device. Alternatively, a display can be automatically moved from its first configuration to its second configuration by one or more actuators. Alternatively, a display can be automatically moved from its first configuration to its second configuration by one or more electromagnetic actuators. In an example, a display can be selectively and reversibly locked into its first configuration or its second configuration by the person wearing the device.

There are advantages and disadvantages to a having a wearable display be flexible. Advantages of having a wearable display be flexible include: being able to change the shape of the display as it is moved from one location to another on a wearable device; and being able to expand the display by unrolling, unfolding, and/or unbending the display. Disadvantages of having a wearable be flexible include: distortion of images on an uneven (e.g. non-flat) surface; and lack of uniform resistance for use of the display as a touch screen.

In order to provide the advantages of having a wearable display be flexible without the disadvantages thereof, a wearable device can have a display whose flexibility can be changed (e.g. adjusted). In an example, the flexibility of a display can be adjusted so that the display can be made more flexible (so that its shape can be changed) or can made be less flexible (so that it can serve as a touch screen). In an example, the flexibility of a display can be adjusted so that it can be made more flexible (to transition from one shape to another) or can be made less flexible (so that it can be stabilized in a selected shape for use as a touch screen). In an example, the flexibility of a display can be adjusted so that it can be made more flexible (to transition from an unexpanded size to an expanded size) and can be made less flexible (so that it can be stabilized in an expanded size for use as a touch screen).

In an example, a display can comprise a plurality of flexibly-connected segments. When the segments are sufficiently small relative to the overall display, the overall display can be relatively flexible, bendable, and rollable. In an example, a display can comprise between 20 and 60 flexibly-connected segments. In an example, a display can comprise between 50 and 100 flexibly-connected segments. In an example, a display can comprise a plurality of rectangular segments which are flexibly connected along their longitudinal (longer) sides. In an example, a display can comprise a plurality of parallel rectangular segments which are flexibly connected along their longitudinal (longer) sides. In an example, a display can comprise a plurality of flexibly-connected hexagonal segments.

In an example, the spacing between flexibly-connected segments comprising a display can be changed (e.g. adjusted) in order to change (e.g. adjust) the flexibility and/or rigidity of the display. In an example, a display can comprise a plurality of adjustably-connected segments so that the flexibility of the display can be adjusted. In an example, a display can have a layer of adjustably-connected segments so that the flexibility of the display can be adjusted. In an example, when flexibly-connected segments are farther apart from each other, then the display becomes more flexible, less rigid, more bendable, and/or more rollable, but when flexibly-connected segments are closer together, then the display becomes less flexible, more rigid, less bendable, and/or less rollable.

In an flexibly-connected segments can be connected to each other by filaments, wires, cables, chains, springs, strings, and/or threads. In an example, spacing between the segments can be adjusted by adjusting the tension of the filaments, wires, cables, chains, springs, strings, and/or threads. In an example, the flexibility of a display which comprises a plurality of flexibly-connected segments can be adjusted by adjusting the tension of filaments, wires, cables, chains, springs, strings, and/or threads which connect the flexibly-connected segments.

In an example, a display can comprise a plurality of adjustably-connected segments with interdigitated protrusions and recesses so that the flexibility of the display can be adjusted. In an example, a display can comprise a plurality of adjustably-connected tongue-and-groove segments with interdigitated protrusions and recesses so that the flexibility of the display can be adjusted. In an example, a display can comprise a plurality of rectangular adjustably-connected tongue-and-groove segments with interdigitated protrusions and recesses so that the flexibility of the display can be adjusted.

In an example, segments in a plurality of adjustably-connected segments can be shaped like tongue-and-groove floor boards, wherein a protrusion on a side of a first segment fits into a recess on a side of an adjacent second segment when the two segments are pushed (or pulled) close together. Unlike floor boards which are pushed together (e.g. by the lateral force of a hammer) into a permanently-interdigitated configuration, segments in a display can be reversibly pulled (or pushed) closer together or father apart. When these segments are pulled (or pushed) closer together, they interlock and the display becomes more rigid. When these segments are pulled (or pushed) farther apart, they detach from each other and the display becomes more flexible. In an example, these segments can be connected by filaments, wires, and/or strings, wherein increasing the tension (and/or decreasing the length) of the filaments, wires, and/or strings pulls the segments closer together and decreasing the tension (and/or increasing the length) of the filaments, wires, and/or strings moves the segments farther apart.

In an example, a display can made with an electroactive polymer. In an example, the flexibility of the display can be adjusted by application of electrical (and/or electromagnetic) energy to the polymer. In an example, a display can comprise a layer made with an electroactive polymer so that the flexibility of the display can be adjusted by application of electrical (and/or electromagnetic) energy to the polymer. In an example, this layer can become more flexible when electrical energy is applied to it. Alternatively, this layer can become more rigid when electrical energy is applied to it. In an example, a display can have a layer which is made with shape memory material. In an example, applying electrical energy to the shape memory material can make the display more flexible. Alternatively, applying electrical energy to the shape memory material can make the display more rigid.

In an example, a display can be flexible. In an example, a display can be bent and unbent without damage to the display. In an example, a display can be bendable so that it can be folded or unfolded without damage to the display. In an example, a display can be bendable so that it can be rolled or unrolled without damage to the display. In an example, the bendability of a display can be adjusted so that it becomes more bendable (so that its shape can be changed) or less bendable (so that it can serve as a touch screen). In an example, the bendability of a display can be adjusted so that it becomes more bendable (to transition from one shape to another) or less bendable (so that it can be stabilized in a selected shape).

In an example, a display can comprise a plurality of adjustable-connected segments (e.g. tongue-and-groove segments) which enable the bendability of the display to be adjusted. In an example, a display can comprise a plurality of adjustable-connected segments (e.g. tongue-and-groove segments) with interdigitated protrusions and recesses so that the bendability of the display can be adjusted. In an example, a display can made with an electroactive polymer so that the bendability of the display can be adjusted by application of electrical (and/or electromagnetic) energy.

In an example, a display can be rollable. In an example, a display can be rolled, coiled, and/or wound without damage to the display. In an example, a display can be wound or unwound around a roller (e.g. roller, spool, cylinder, rod, or pin) without damage to the display. In an example, a display can be rolled, coiled, and/or wound around a roller (e.g. roller, spool, cylinder, rod, or pin) (and also unrolled, uncoiled, and/or unwound from the roller (e.g. roller, spool, cylinder, rod, or pin) without damage to the display. In an example, a display can be rolled, coiled, and/or wound (e.g. around a roller (e.g. roller, spool, cylinder, rod, or pin) into an unexpanded configuration and unrolled, uncoiled, and/or unwound (e.g. from the roller (e.g. roller, spool, cylinder, rod, or pin) into an expanded configuration.

In an example, a device can have a single roller mechanism comprising a roller (e.g. roller, spool, cylinder, rod, or pin) on one side of a flexible display. In an example, this side of the display can be rolled (e.g. rolled, coiled, and/or wound) around this roller or unrolled (e.g. unrolled, uncoiled, and/or unwound) from this roller. In an example, a device can have two roller mechanisms on opposite sides of a flexible display. In an example, each side of the display can be rolled (e.g. rolled, coiled, and/or wound) around one of the two rollers roller or unrolled (e.g. unrolled, uncoiled, and/or unwound) from that roller. In an example, rollers in two different roller mechanisms can rotate in opposite directions (e.g. one clockwise and one counter-clockwise) as a flexible display is expanded.

In an example, a display can comprise a plurality of adjustable-connected segments (e.g. tongue-and-groove segments) so that it can be rolled, coiled, and/or wound around a roller (e.g. roller, spool, cylinder, rod, or pin). In an example, the tension of longitudinal elements which connect the segments can be decreased so that the display becomes more flexible in order to be rolled, coiled, and/or wound around a roller (e.g. roller, spool, cylinder, rod, or pin). In an example, the tension of longitudinal elements which connect the segments can be increased relaxed so that the display becomes more rigid in order to display a flat image and serve as a touch screen.

In an example, the (outward-facing) size of a display can be reduced by rolling, coiling, and/or winding (e.g. one side of) the display around a roller (e.g. roller, spool, cylinder, rod, or pin). In an example, the (outward-facing) size of the display can be increased by unrolling, uncoiling, and/or unwinding (e.g. one side of) the display from around the roller (e.g. roller, spool, cylinder, rod, or pin). In an example, the visible surface area of a display can be reduced by rolling, coiling, and/or winding (e.g. one side of) the display around a roller (e.g. roller, spool, cylinder, rod, or pin). In an example, the visible surface area of the display can be increased by unrolling, uncoiling, and/or unwinding (e.g. one side of) the display from around the roller (e.g. roller, spool, cylinder, rod, or pin).

In an example, the lower surface and/or the lateral sides of the display can have protrusions or recesses (e.g. teeth, ridges, notches, or undulations) and a roller (e.g. roller, spool, cylinder, rod, or pin) around which the display is rolled, coiled, and/or wound can have recesses or protrusions (e.g. teeth, ridges, notches, or undulations) which are geometrically complementary to those of the display. In an example, the protrusions or recesses on the display can interdigitate (e.g. interdigitate, engage, and/or mesh) with the recesses or protrusions on the roller. In an example, a roller (e.g. roller, spool, cylinder, rod, or pin) can comprise a gear which engages protrusions or recesses (e.g. teeth, ridges, notches, or undulations) on the lower surface of a display.

In an example, a display can be rolled, coiled, and/or wound around a single roller (e.g. roller, spool, cylinder, rod, or pin). In an example, a display can be rolled, coiled, and/or wound around two or more rollers (e.g. rollers, spools, cylinders, rods, or pins). In an example, the distance between the two rollers (e.g. rollers, spools, cylinders, rods, or pins) can be changed. In an example, the (outward-facing) size of a display can be increased by decreasing the distance between the two rollers (e.g. rollers, spools, cylinders, rods, or pins) around which a display is looped. In an example, a display can be rolled, coiled, and/or wound around a first roller (e.g. roller, spool, cylinder, rod, or pin) and looped around (e.g. bent around part of the circumference of) a second roller (e.g. roller, spool, cylinder, rod, or pin).

In an example, a display can display an image (e.g. text, picture, or other visual content). In an example, a display can comprise a plurality (e.g. an array or matrix) of light-emitting elements which collectively display an image (e.g. text, picture, or other visual content). In an example, a display can display a digital image. In an example, a display can be a computer display and/or screen. In an example, a display can be a holographic display. In an example, a display can be a touch screen (e.g. a touch and/or gesture responsive display). In an example, a display can comprise light-sensing elements as well as light-emitting elements.

In an example, a display can display an image (e.g. text, picture, or other visual content) via a plurality (e.g. an array or matrix) of light-emitting elements. In an example, light-emitting elements in a plurality of light-emitting elements can be selected from the group consisting of: Light Emitting Diode (LED), Direct-Lit LED, Edge-Lit LED (ELED), Encapsulated LED, Micro-LED, Mini-LED, Monochromatic LED (MLED), Organic Light Emitting Diode (OLED), Light Emitting Diode Zep Elin (LED Zep Elin), Quantum Dot LED (QLED), Resonant Cavity Light Emitting Diode (RCLED), Super-Luminescent Light Emitting Diode (SLED), and Tunable LED.

In an example, a display can be flexible, bendable, and/or rollable. In an example, a display can be expandable. In an example, a display can have a variable size which changes over time. In an example, a display can be expanded from a first configuration with a first size to a second configuration with a second size, wherein the second size is greater than the first size. In an example, the second size can be at least twice the first size. In an example, a display can have two configurations. In an example, a display can be expanded in its second configuration relative to its first configuration. In an example, the size of a display in its second configuration can be between 150% and 300% of the size of the display in its first configuration. In an example, the size of a display in its second configuration can be at least twice the size of the display in its first configuration.

In an example, a display can have a square (or square with rounded vertexes) shape in its first (unexpanded) configuration and a rectangular (or rectangular with rounded vertexes) shape in its second (expanded) configuration. In an example, a display can have a square (or square with rounded vertexes) shape in its first (unexpanded) configuration and a rectangular (or rectangular with rounded vertexes) shape in its second (expanded) configuration, wherein a narrow side of the rectangle is equal in length to a side of the square. In an example, a display can have a square (or square with rounded vertexes) shape with a first size in its first (unexpanded) configuration and a square (or square with rounded vertexes) shape with a second size in its second (expanded) configuration, wherein the second size is at least twice as large as the first size.

In an example, a display can have a plurality of axes and be expanded (from its first configuration to its second configuration) in the direction of just one of its axes. In an example, a display can have a plurality of axes and be expanded only in a direction which is parallel to its shortest axis. Alternatively, a display can have a plurality of axes and be expanded only in the direction which is parallel to its longest axis. In an example, a display can be expanded (from its first configuration to its second configuration) in a direction which is orthogonal to the plane of the circumference of the device and/or the person's wrist. Alternatively, a display can be expanded (from its first configuration to its second configuration) in a direction which is parallel to the plane of the circumference of the device. In an example, a display can be expanded (from its first configuration to its second configuration) in a direction which is parallel to the plane of the circumference of the device and tangential to the circumference of the device.

In this example, a display is expanded in one direction. If this device were to be worn on a person's left wrist and/or lower arm, then the direction of expansion of the display would be: away from the plane of the circumference of the device, toward the person's elbow, and onto the dorsal surface of the person's lower arm. In an alternative example, the direction of expansion of the display can be in the opposite direction: away from the plane of the circumference of the device, away from the person's elbow, and onto the back of the person's hand. In another example, a display could be expanded in two opposite directions: (1) expansion away from the plane of the circumference of the device, toward the person's elbow, and onto the dorsal surface of the person's lower arm; and also (2) expansion away from the plane of the circumference of the device, away from the person's elbow, and onto the back of the person's hand.

In an example, a flexible display can be expanded (e.g. expanded, extended, lengthened, and/or widened) being unrolled (e.g. unrolled, unwound, and/or uncoiled) from a roller (e.g. roller, spool, cylinder, rod, or pin). In an example, a flexible display can be expanded from its (unexpanded) first configuration to its second (expanded) configuration as it is unrolled (e.g. unrolled, unwound, and/or uncoiled) from a roller (e.g. roller, spool, cylinder, rod, or pin). In an example, a flexible display can be manually expanded when user pulls a side (or end) of the display which is opposite to a roller (e.g. roller, spool, cylinder, rod, or pin) around which the display is rolled, wound, and/or coiled. In an example, a flexible display can be automatically expanded when an actuator rotates a roller (e.g. roller, spool, cylinder, rod, or pin) around which the display is rolled, wound, and/or coiled, thereby unrolling, unwinding, and/or uncoiling the display.

In an example, a display can be expanded (e.g. expanded, extended, lengthened, and/or widened) by reducing the degree of overlap between two or more display sections which together comprise the display. In an example, one display section can be slid outward from underneath another display section. In an example, two display sections can be non-coplanar and overlapping in a first configuration and can be coplanar and non-overlapping in a second configuration. In an example, two or more display sections can be rigid and separate from each other, wherein the display is expanded by sliding one rigid section out from underneath the other rigid section. Alternatively, two or more display sections can be flexible, continuous with each other around a rotating roller (e.g. roller, spool, cylinder, rod, or pin), wherein the size of the upper (visible) section is increased and the size of the lower (non-visible) section is decreased by rotating the roller (e.g. roller, spool, cylinder, rod, or pin).

In an example, the flexibility and/or rigidity of the display can be changed. In an example, the display can be made more flexible to facilitate moving it from its first configuration to its second configuration, but can then be made more rigid to facilitate a stable, flat image (and/or its use as a touch screen). In an example, a display can further comprise (a layer of) a plurality of narrow rigid connected sections, wherein the display becomes more flexible (less rigid) when the sections are more loosely connected to each other and the display becomes more rigid (less flexible) when the sections are more tightly connected to each other. In an example, the degree to which sections are loosely or tightly connected to each other can be adjusted. In an example, the degree to which sections are loosely or tightly connected to each other can be adjusting the tension of one or more filaments, wires, or strings which connect the sections to each other. In an example, narrow rigid connected sections can have "tongue-and-grove" shapes, wherein a protrusion on an end of section fits into a recess on an end of a neighboring section when the sections are pulled close together. In this manner, the display be flexible for changing configuration (including possibly changing curvature), but can be made into a relatively flat, rigid surface for use as a flat, rigid touch screen in its expanded configuration.

In an example, a display can comprise at least four layers. A (top) first layer can be a flexible protective layer. A second layer can comprise an array and/or matrix of light-emitters. A third layer can comprise a plurality of electroconductive pathways which provide power to the light-emitters. A (bottom) fourth layer can comprise a plurality of flexibly-connected segments, wherein changing the spacing between the segments changes the overall flexibility and/or rigidity of the display. The fourth layer can be made less rigid, more flexible, and more arcuate to facilitate changing the configuration of the display, but can also be made more rigid, less flexible, and more flat to facilitate use of the display as a touch screen.

In an example, a (bottom) fourth layer of a display can comprise a plurality of connected "tongue-and-groove" segments which interlocking protrusions and recesses which fit into each other when they are pulled tightly together. In an example, the "tongue-and-groove" segments can be connected by filaments, wires, or strings. When the tension of the filaments, wires, or strings is decreased, then the fourth layer (and the whole display) becomes less rigid, more flexible, and more arcuate. When the tension of the filaments, wires, or strings is increased, then the fourth layer (and the whole display) becomes more rigid, less flexible, and more flat.

In another example, a (bottom) fourth layer of a display can comprise material whose rigidity, flexibility, and/or shape is affected by the application of electrical energy. In an example, a fourth layer can become more rigid, less flexible, and/or more flat when electrical energy is applied to it. Alternative, a fourth layer can become less rigid, more flexible, and/or more arcuate when electrical energy is applied to it. In an example, a fourth layer can be made from an electroactive polymer (EAP). In an example, a fourth layer can be made from shape-memory material.

In an example, a display can comprise at least three layers. A (top) first layer can be a flexible protective layer. A second layer can comprise an array and/or matrix of light-emitters and electroconductive pathways which provide power to the light-emitters. A third layer can comprise a plurality of flexibly-connected segments, wherein changing the spacing between the segments changes the overall flexibility and/or rigidity of the display. The third layer can be made less rigid, more flexible, and more arcuate to facilitate changing the configuration of the display, but can also be made more rigid, less flexible, and more flat to facilitate use of the display as a touch screen.

In an example, this device can further comprise a battery, a data processor, and a wireless data transmitter and/or receiver. In an example, this device can further comprise other components selected from the group consisting of: battery, data processor, electromagnetic actuator, infrared light sensor, laser, microphone, motion sensor, one or more buttons, speaker, spectroscopy sensor, visible light sensor, watch crown, wireless data receiver, and wireless data transmitter. Relevant device variations discussed elsewhere in this disclosure or in priority-linked disclosures can be applied to the example shown in this figure.

Figure 42:
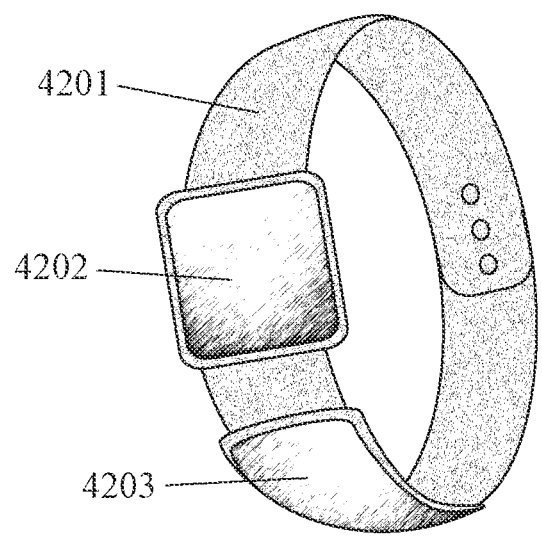
FIGS. 42 and 43 show two sequential views of a wearable device with a dorsal first display and a lateral second display, wherein the lateral display expands out from the lateral portion of the device.
Figure 43:
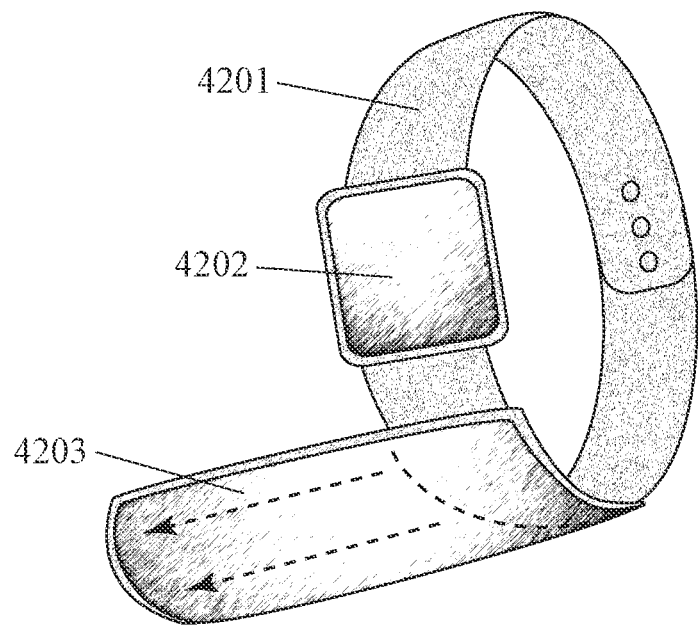

FIGS. 42 and 43 show another example of how this invention can be embodied in a wearable device with an expandable display. In this example, a first display 4202 is on a dorsal portion of the device 4201 and a second display 4203 is expanded from a lateral portion of the device. FIG. 42 shows this device in a first configuration before a second display is expanded. FIG. 43 shows this device in a second configuration when after the second display has been expanded. Relevant device variations discussed elsewhere in this disclosure or in priority-linked disclosures can be applied to the example shown in this figure.

Figure 44:
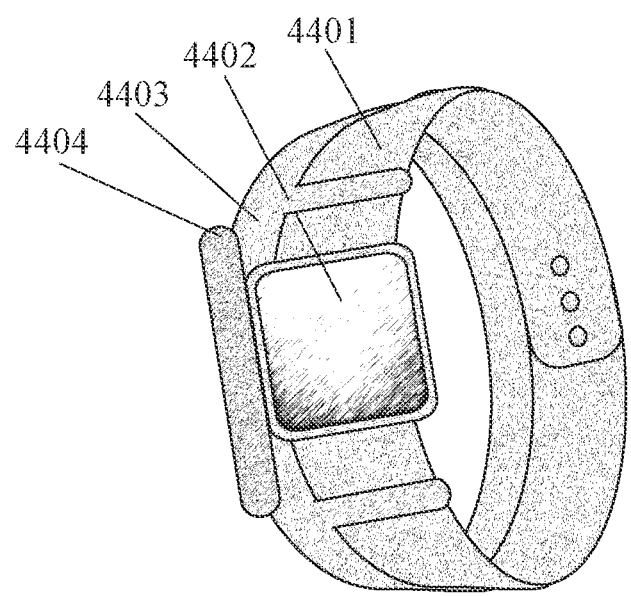
FIGS. 44 and 45 show two sequential views of an expandable display which is attached (e.g. as an accessory) to a smart watch or other wrist-worn device.
Figure 45:
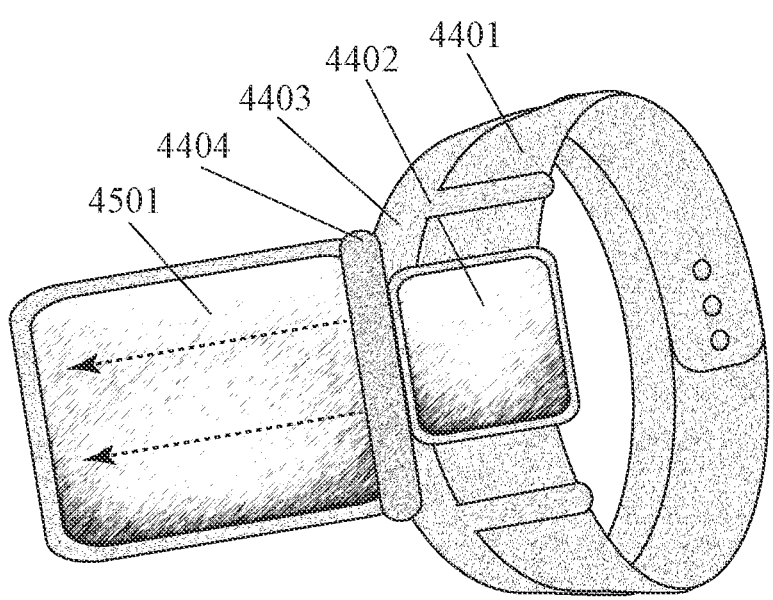

FIGS. 44 and 45 show another example of how this invention can be embodied in a wearable device with an expandable display. In this example, an expandable display is an accessory to a conventional smart watch (or other wrist-worn device). In this example, an expandable display can be a modular attachment to a conventional smart watch. In this example, the invention is embodied in a separate device with an expandable display which is removably-attached to a conventional smart watch which already has a display. This provides an expandable second display for a conventional smart watch, without having to entirely replace the conventional smart watch.

FIGS. 44 through 45 show two oblique side views, at two different times, of an example of an expandable display device which is removably-attached to an existing smart watch (or other wrist-worn technology) comprising: an expandable display 4501; a housing 4404; and an attachment mechanism 4403; wherein the expandable display is retracted into the housing in a first (unexpanded) configuration and is extended out from the housing in a second (expanded) configuration, wherein the attachment mechanism removably-attaches the housing to a smart watch (or other wrist-worn technology) 4401 which has a non-expandable display 4402. FIG. 44 shows this device having been attached to a existing smart watch before and when the expandable display is in its first (unexpanded) configuration. FIG. 45 shows this device having been attached to a existing smart watch and when the expandable display is in its second (expanded) configuration.

In the example, this device can further comprise a roller (e.g. roller, spool, cylinder, rod, and/or pin) around which the expandable display is rolled (e.g. rolled, coiled, and/or wound) or from which the expandable display is unrolled (e.g. unrolled, uncoiled, and/or unwound). In an example, this roller can be inside the housing. In the example, this device can further comprise a roller (e.g. roller, spool, cylinder, rod, and/or pin) in the housing around which the expandable display is rolled (e.g. rolled, coiled, and/or wound) or from which the expandable display is unrolled (e.g. unrolled, uncoiled, and/or unwound). In an example, and expandable display can be a flexible display which is unrolled (e.g. unrolled, uncoiled, and/or unwound) from its first (unexpanded) configuration to its second (expanded) configuration.

In another embodiment, an expandable display can comprise a plurality of sliding and/or telescoping sections. In an example, in a first (unexpanded) configuration, the sections of an expandable display can be substantially parallel to each other and non-coplanar. In an example, in a second (expanded) configuration, the sections of this expandable display can be coplanar. In an example, one or more sections can slide out from under one or more other sections to change a display from its first (unexpanded) configuration to its second (expanded) configuration.

In an example, an attachment mechanism can attach a housing to the band of a conventional smart watch. In an example, there can be two or more openings in an attachment mechanism through which the band of a conventional smart watch is inserted, pulled, and/or threaded, thereby attaching this device to the conventional smart watch. In an example an attachment mechanism can be a band which encircles some or all of a person's wrist. In an example, the plane of the circumference of this band can be substantially parallel to the plane of the circumference of the band of the smart watch. In the example shown in FIGS. 44 and 45, the attachment mechanism is a band which encircles a person's wrist, wherein the band has two openings through which the band of the smart watch is inserted, pulled, and/or threaded.

In another example, an attachment mechanism which attaches a housing to a conventional smart watch can be selected from the group consisting of: buckle, clamp, clasp, clip, hook, hook and loop fabric, magnet, pin, plug, and strap. In another example, this device can be a modular attachment which is attached to the band of a conventional smart watch by an attachment mechanism selected from the group consisting of: buckle, clamp, clasp, clip, hook, hook and loop fabric, magnet, opening through which smart watch band is inserted, pin, plug, and strap.

In an example, a expandable display can be flexible, bendable, and/or rollable. In an example, a expandable display can be flexible, bendable, and/or rollable so that it can transition between unexpanded and expanded configurations without the expandable display being damaged. In an example, a expandable display can be flexible so that it can change between being flat (e.g. planar) and arcuate (e.g. curved) without the expandable display being damaged. In an example, a expandable display can be flexible so that it can change between flat, concave, and convex shapes. In an example, a expandable display can be flexible so that it can change between flat, concave, or convex configurations.

In an example, a expandable display can be manually moved from its first configuration to its second configuration. Alternatively, a expandable display can be automatically moved from its first configuration to its second configuration by one or more actuators. An expandable display can be automatically moved from its first configuration to its second configuration by one or more electromagnetic actuators. In an example, a expandable display can be selectively and reversibly locked into its first configuration or its second configuration by the person wearing the device.

There are advantages and disadvantages to a having a wearable expandable display be flexible. Advantages of having a wearable expandable display be flexible include: being able to change the shape of the expandable display as it is moved from one location to another on a wearable device; and being able to expand the expandable display by unrolling, unfolding, and/or unbending the expandable display. Disadvantages of having a wearable be flexible include: distortion of images on an uneven (e.g. non-flat) surface; and lack of uniform resistance for use of the expandable display as a touch screen.

In order to provide the advantages of having a wearable expandable display be flexible without the disadvantages thereof, a wearable device can have a expandable display whose flexibility can be changed (e.g. adjusted). In an example, the flexibility of a expandable display can be adjusted so that the expandable display can be made more flexible (so that its shape can be changed) or can made be less flexible (so that it can serve as a touch screen). In an example, the flexibility of a expandable display can be adjusted so that it can be made more flexible (to transition from one shape to another) or can be made less flexible (so that it can be stabilized in a selected shape for use as a touch screen). In an example, the flexibility of a expandable display can be adjusted so that it can be made more flexible (to transition from an unexpanded size to an expanded size) and can be made less flexible (so that it can be stabilized in an expanded size for use as a touch screen).

In an example, a expandable display can comprise a plurality of flexibly-connected segments. When the segments are sufficiently small relative to the overall expandable display, the overall expandable display can be relatively flexible, bendable, and rollable. In an example, a expandable display can comprise between 20 and 60 flexibly-connected segments. In an example, a expandable display can comprise between 50 and 100 flexibly-connected segments. In an example, a expandable display can comprise a plurality of rectangular segments which are flexibly connected along their longitudinal (longer) sides. In an example, a expandable display can comprise a plurality of parallel rectangular segments which are flexibly connected along their longitudinal (longer) sides. In an example, a expandable display can comprise a plurality of flexibly-connected hexagonal segments.

In an example, the spacing between flexibly-connected segments comprising a expandable display can be changed (e.g. adjusted) in order to change (e.g. adjust) the flexibility and/or rigidity of the expandable display. In an example, a expandable display can comprise a plurality of adjustably-connected segments so that the flexibility of the expandable display can be adjusted. In an example, a expandable display can have a layer of adjustably-connected segments so that the flexibility of the expandable display can be adjusted. In an example, when flexibly-connected segments are farther apart from each other, then the expandable display becomes more flexible, less rigid, more bendable, and/or more rollable, but when flexibly-connected segments are closer together, then the expandable display becomes less flexible, more rigid, less bendable, and/or less rollable.

In an flexibly-connected segments can be connected to each other by filaments, wires, cables, chains, springs, strings, and/or threads. In an example, spacing between the segments can be adjusted by adjusting the tension of the filaments, wires, cables, chains, springs, strings, and/or threads. In an example, the flexibility of a expandable display which comprises a plurality of flexibly-connected segments can be adjusted by adjusting the tension of filaments, wires, cables, chains, springs, strings, and/or threads which connect the flexibly-connected segments.

In an example, a expandable display can comprise a plurality of adjustably-connected segments with interdigitated protrusions and recesses so that the flexibility of the expandable display can be adjusted. In an example, a expandable display can comprise a plurality of adjustably-connected tongue-and-groove segments with interdigitated protrusions and recesses so that the flexibility of the expandable display can be adjusted. In an example, a expandable display can comprise a plurality of rectangular adjustably-connected tongue-and-groove segments with interdigitated protrusions and recesses so that the flexibility of the expandable display can be adjusted.

In an example, segments in a plurality of adjustably-connected segments can be shaped like tongue-and-groove floor boards, wherein a protrusion on a side of a first segment fits into a recess on a side of an adjacent second segment when the two segments are pushed (or pulled) close together. Unlike floor boards which are pushed together (e.g. by the lateral force of a hammer) into a permanently-interdigitated configuration, segments in a expandable display can be reversibly pulled (or pushed) closer together or father apart. When these segments are pulled (or pushed) closer together, they interlock and the expandable display becomes more rigid. When these segments are pulled (or pushed) farther apart, they detach from each other and the expandable display becomes more flexible. In an example, these segments can be connected by filaments, wires, and/or strings, wherein increasing the tension (and/or decreasing the length) of the filaments, wires, and/or strings pulls the segments closer together and decreasing the tension (and/or increasing the length) of the filaments, wires, and/or strings moves the segments farther apart.

In an example, a expandable display can made with an electroactive polymer. In an example, the flexibility of the expandable display can be adjusted by application of electrical (and/or electromagnetic) energy to the polymer. In an example, a expandable display can comprise a layer made with an electroactive polymer so that the flexibility of the expandable display can be adjusted by application of electrical (and/or electromagnetic) energy to the polymer. In an example, this layer can become more flexible when electrical energy is applied to it. Alternatively, this layer can become more rigid when electrical energy is applied to it. In an example, a expandable display can have a layer which is made with shape memory material. In an example, applying electrical energy to the shape memory material can make the expandable display more flexible. Alternatively, applying electrical energy to the shape memory material can make the expandable display more rigid.

In an example, a expandable display can be flexible. In an example, a expandable display can be bent and unbent without damage to the expandable display. In an example, a expandable display can be bendable so that it can be folded or unfolded without damage to the expandable display. In an example, a expandable display can be bendable so that it can be rolled or unrolled without damage to the expandable display. In an example, the bendability of a expandable display can be adjusted so that it becomes more bendable (so that its shape can be changed) or less bendable (so that it can serve as a touch screen). In an example, the bendability of a expandable display can be adjusted so that it becomes more bendable (to transition from one shape to another) or less bendable (so that it can be stabilized in a selected shape).

In an example, a expandable display can comprise a plurality of adjustable-connected segments (e.g. tongue-and-groove segments) which enable the bendability of the expandable display to be adjusted. In an example, a expandable display can comprise a plurality of adjustable-connected segments (e.g. tongue-and-groove segments) with interdigitated protrusions and recesses so that the bendability of the expandable display can be adjusted. In an example, a expandable display can made with an electroactive polymer so that the bendability of the expandable display can be adjusted by application of electrical (and/or electromagnetic) energy.

In an example, a expandable display can be rollable. In an example, a expandable display can be rolled, coiled, and/or wound without damage to the expandable display. In an example, a expandable display can be wound or unwound around a roller (e.g. roller, spool, cylinder, rod, or pin) without damage to the expandable display. In an example, a expandable display can be rolled, coiled, and/or wound around a roller (e.g. roller, spool, cylinder, rod, or pin) (and also unrolled, uncoiled, and/or unwound from the roller (e.g. roller, spool, cylinder, rod, or pin) without damage to the expandable display. In an example, a expandable display can be rolled, coiled, and/or wound (e.g. around a roller (e.g. roller, spool, cylinder, rod, or pin) into an unexpanded configuration and unrolled, uncoiled, and/or unwound (e.g. from the roller (e.g. roller, spool, cylinder, rod, or pin) into an expanded configuration.

In an example, a device can have a single roller mechanism comprising a roller (e.g. roller, spool, cylinder, rod, or pin) on one side of a flexible expandable display. In an example, this side of the expandable display can be rolled (e.g. rolled, coiled, and/or wound) around this roller or unrolled (e.g. unrolled, uncoiled, and/or unwound) from this roller. In an example, a device can have two roller mechanisms on opposite sides of a flexible expandable display. In an example, each side of the expandable display can be rolled (e.g. rolled, coiled, and/or wound) around one of the two rollers roller or unrolled (e.g. unrolled, uncoiled, and/or unwound) from that roller. In an example, rollers in two different roller mechanisms can rotate in opposite directions (e.g. one clockwise and one counter-clockwise) as a flexible expandable display is expanded.

In an example, a expandable display can comprise a plurality of adjustable-connected segments (e.g. tongue-and-groove segments) so that it can be rolled, coiled, and/or wound around a roller (e.g. roller, spool, cylinder, rod, or pin). In an example, the tension of longitudinal elements which connect the segments can be decreased so that the expandable display becomes more flexible in order to be rolled, coiled, and/or wound around a roller (e.g. roller, spool, cylinder, rod, or pin). In an example, the tension of longitudinal elements which connect the segments can be increased relaxed so that the expandable display becomes more rigid in order to expandable display a flat image and serve as a touch screen.

In an example, the (outward-facing) size of a expandable display can be reduced by rolling, coiling, and/or winding (e.g. one side of) the expandable display around a roller (e.g. roller, spool, cylinder, rod, or pin). In an example, the (outward-facing) size of the expandable display can be increased by unrolling, uncoiling, and/or unwinding (e.g. one side of) the expandable display from around the roller (e.g. roller, spool, cylinder, rod, or pin). In an example, the visible surface area of a expandable display can be reduced by rolling, coiling, and/or winding (e.g. one side of) the expandable display around a roller (e.g. roller, spool, cylinder, rod, or pin). In an example, the visible surface area of the expandable display can be increased by unrolling, uncoiling, and/or unwinding (e.g. one side of) the expandable display from around the roller (e.g. roller, spool, cylinder, rod, or pin).

In an example, the lower surface and/or the lateral sides of the expandable display can have protrusions or recesses (e.g. teeth, ridges, notches, or undulations) and a roller (e.g. roller, spool, cylinder, rod, or pin) around which the expandable display is rolled, coiled, and/or wound can have recesses or protrusions (e.g. teeth, ridges, notches, or undulations) which are geometrically complementary to those of the expandable display. In an example, the protrusions or recesses on the expandable display can interdigitate (e.g. interdigitate, engage, and/or mesh) with the recesses or protrusions on the roller. In an example, a roller (e.g. roller, spool, cylinder, rod, or pin) can comprise a gear which engages protrusions or recesses (e.g. teeth, ridges, notches, or undulations) on the lower surface of a expandable display.

In an example, a expandable display can be rolled, coiled, and/or wound around a single roller (e.g. roller, spool, cylinder, rod, or pin). In an example, a expandable display can be rolled, coiled, and/or wound around two or more rollers (e.g. rollers, spools, cylinders, rods, or pins). In an example, the distance between the two rollers (e.g. rollers, spools, cylinders, rods, or pins) can be changed. In an example, the (outward-facing) size of a expandable display can be increased by decreasing the distance between the two rollers (e.g. rollers, spools, cylinders, rods, or pins) around which a expandable display is looped. In an example, a expandable display can be rolled, coiled, and/or wound around a first roller (e.g. roller, spool, cylinder, rod, or pin) and looped around (e.g. bent around part of the circumference of) a second roller (e.g. roller, spool, cylinder, rod, or pin).

In an example, a expandable display can expandable display an image (e.g. text, picture, or other visual content). In an example, a expandable display can comprise a plurality (e.g. an array or matrix) of light-emitting elements which collectively expandable display an image (e.g. text, picture, or other visual content). In an example, a expandable display can expandable display a digital image. In an example, a expandable display can be a computer expandable display and/or screen. In an example, a expandable display can be a holographic expandable display. In an example, a expandable display can be a touch screen (e.g. a touch and/or gesture responsive expandable display). In an example, a expandable display can comprise light-sensing elements as well as light-emitting elements.

In an example, a expandable display can expandable display an image (e.g. text, picture, or other visual content) via a plurality (e.g. an array or matrix) of light-emitting elements. In an example, light-emitting elements in a plurality of light-emitting elements can be selected from the group consisting of: Light Emitting Diode (LED), Direct-Lit LED, Edge-Lit LED (ELED), Encapsulated LED, Micro-LED, Mini-LED, Monochromatic LED (MLED), Organic Light Emitting Diode (OLED), Light Emitting Diode Zep Elin (LED Zep Elin), Quantum Dot LED (QLED), Resonant Cavity Light Emitting Diode (RCLED), Super-Luminescent Light Emitting Diode (SLED), and Tunable LED.

In an example, a expandable display can be flexible, bendable, and/or rollable. In an example, a expandable display can be expandable. In an example, a expandable display can have a variable size which changes over time. In an example, a expandable display can be expanded from a first configuration with a first size to a second configuration with a second size, wherein the second size is greater than the first size. In an example, the second size can be at least twice the first size. In an example, a expandable display can have two configurations. In an example, a expandable display can be expanded in its second configuration relative to its first configuration. In an example, the size of a expandable display in its second configuration can be between 150% and 300% of the size of the expandable display in its first configuration. In an example, the size of a expandable display in its second configuration can be at least twice the size of the expandable display in its first configuration.

In an example, a expandable display can have a square (or square with rounded vertexes) shape in its first (unexpanded) configuration and a rectangular (or rectangular with rounded vertexes) shape in its second (expanded) configuration. In an example, a expandable display can have a square (or square with rounded vertexes) shape in its first (unexpanded) configuration and a rectangular (or rectangular with rounded vertexes) shape in its second (expanded) configuration, wherein a narrow side of the rectangle is equal in length to a side of the square. In an example, a expandable display can have a square (or square with rounded vertexes) shape with a first size in its first (unexpanded) configuration and a square (or square with rounded vertexes) shape with a second size in its second (expanded) configuration, wherein the second size is at least twice as large as the first size.

In an example, a expandable display can have an arcuate shape which is substantially parallel to the arcuate shape of a lateral portion of the device when the expandable display is in its first configuration. In an example, the shape of a expandable display in its first configuration can be a section of cylinder which is substantially parallel to the surface of a person's wrist. In an example, a expandable display can be longitudinally-concave in its first configuration and longitudinally-flat in its second configuration. In an example, a expandable display can be longitudinally-convex in its first configuration and longitudinally-flat in its second configuration.

In an example, a expandable display can have a plurality of axes and be expanded (from its first configuration to its second configuration) in the direction of just one of its axes. In an example, a expandable display can have a plurality of axes and be expanded only in a direction which is parallel to its shortest axis. Alternatively, a expandable display can have a plurality of axes and be expanded only in the direction which is parallel to its longest axis. In an example, a expandable display can be expanded (from its first configuration to its second configuration) in a direction which is orthogonal to the plane of the circumference of the device and/or the person's wrist. Alternatively, a expandable display can be expanded (from its first configuration to its second configuration) in a direction which is parallel to the plane of the circumference of the device. In an example, a expandable display can be expanded (from its first configuration to its second configuration) in a direction which is parallel to the plane of the circumference of the device and tangential to the circumference of the device.

In an example, a flexible expandable display can be expanded (e.g. expanded, extended, lengthened, and/or widened) being unrolled (e.g. unrolled, unwound, and/or uncoiled) from a roller (e.g. roller, spool, cylinder, rod, or pin). In an example, a flexible expandable display can be expanded from its (unexpanded) first configuration to its second (expanded) configuration as it is unrolled (e.g. unrolled, unwound, and/or uncoiled) from a roller (e.g. roller, spool, cylinder, rod, or pin). In an example, a flexible expandable display can be manually expanded when user pulls a side (or end) of the expandable display which is opposite to a roller (e.g. roller, spool, cylinder, rod, or pin) around which the expandable display is rolled, wound, and/or coiled. In an example, a flexible expandable display can be automatically expanded when an actuator rotates a roller (e.g. roller, spool, cylinder, rod, or pin) around which the expandable display is rolled, wound, and/or coiled, thereby unrolling, unwinding, and/or uncoiling the expandable display.

In an example, a expandable display can be expanded (e.g. expanded, extended, lengthened, and/or widened) by reducing the degree of overlap between two or more expandable display sections which together comprise the expandable display. In an example, one expandable display section can be slid outward from underneath another expandable display section. In an example, two expandable display sections can be non-coplanar and overlapping in a first configuration and can be coplanar and non-overlapping in a second configuration. In an example, two or more expandable display sections can be rigid and separate from each other, wherein the expandable display is expanded by sliding one rigid section out from underneath the other rigid section. Alternatively, two or more expandable display sections can be flexible, continuous with each other around a rotating roller (e.g. roller, spool, cylinder, rod, or pin), wherein the size of the upper (visible) section is increased and the size of the lower (non-visible) section is decreased by rotating the roller (e.g. roller, spool, cylinder, rod, or pin).

In an example, the flexibility and/or rigidity of the expandable display can be changed. In an example, the expandable display can be made more flexible to facilitate moving it from its first configuration to its second configuration, but can then be made more rigid to facilitate a stable, flat image (and/or its use as a touch screen). In an example, a expandable display can further comprise (a layer of) a plurality of narrow rigid connected sections, wherein the expandable display becomes more flexible (less rigid) when the sections are more loosely connected to each other and the expandable display becomes more rigid (less flexible) when the sections are more tightly connected to each other. In an example, the degree to which sections are loosely or tightly connected to each other can be adjusted. In an example, the degree to which sections are loosely or tightly connected to each other can be adjusting the tension of one or more filaments, wires, or strings which connect the sections to each other. In an example, narrow rigid connected sections can have "tongue-and-grove" shapes, wherein a protrusion on an end of section fits into a recess on an end of a neighboring section when the sections are pulled close together. In this manner, the expandable display be flexible for changing configuration (including possibly changing curvature), but can be made into a relatively flat, rigid surface for use as a flat, rigid touch screen in its expanded configuration.

In an example, a expandable display can comprise at least four layers. A (top) first layer can be a flexible protective layer. A second layer can comprise an array and/or matrix of light-emitters. A third layer can comprise a plurality of electroconductive pathways which provide power to the light-emitters. A (bottom) fourth layer can comprise a plurality of flexibly-connected segments, wherein changing the spacing between the segments changes the overall flexibility and/or rigidity of the expandable display. The fourth layer can be made less rigid, more flexible, and more arcuate to facilitate changing the configuration of the expandable display, but can also be made more rigid, less flexible, and more flat to facilitate use of the expandable display as a touch screen.

In an example, a (bottom) fourth layer of a expandable display can comprise a plurality of connected "tongue-and-groove" segments which interlocking protrusions and recesses which fit into each other when they are pulled tightly together. In an example, the "tongue-and-groove" segments can be connected by filaments, wires, or strings. When the tension of the filaments, wires, or strings is decreased, then the fourth layer (and the whole expandable display) becomes less rigid, more flexible, and more arcuate. When the tension of the filaments, wires, or strings is increased, then the fourth layer (and the whole expandable display) becomes more rigid, less flexible, and more flat.

In another example, a (bottom) fourth layer of a expandable display can comprise material whose rigidity, flexibility, and/or shape is affected by the application of electrical energy. In an example, a fourth layer can become more rigid, less flexible, and/or more flat when electrical energy is applied to it. Alternative, a fourth layer can become less rigid, more flexible, and/or more arcuate when electrical energy is applied to it. In an example, a fourth layer can be made from an electroactive polymer (EAP). In an example, a fourth layer can be made from shape-memory material.

In an example, a expandable display can comprise at least three layers. A (top) first layer can be a flexible protective layer. A second layer can comprise an array and/or matrix of light-emitters and electroconductive pathways which provide power to the light-emitters. A third layer can comprise a plurality of flexibly-connected segments, wherein changing the spacing between the segments changes the overall flexibility and/or rigidity of the expandable display. The third layer can be made less rigid, more flexible, and more arcuate to facilitate changing the configuration of the expandable display, but can also be made more rigid, less flexible, and more flat to facilitate use of the expandable display as a touch screen.

In an example, this device can further comprise a battery, a data processor, and a wireless data transmitter and/or receiver. In an example, this device can further comprise other components selected from the group consisting of: battery, data processor, electromagnetic actuator, infrared light sensor, laser, microphone, motion sensor, one or more buttons, speaker, spectroscopy sensor, visible light sensor, watch crown, wireless data receiver, and wireless data transmitter. Relevant device variations discussed elsewhere in this disclosure or in priority-linked disclosures can be applied to the example shown in this figure.

I claim:

1. A wearable device with first and second light-emitting displays comprising:
   a smart watch and/or wrist band which is configured to be worn around at least three-quarters of the circumference of a person's wrist and/or lower arm, wherein a dorsal portion of the smart watch and/or wrist band is configured to be worn on a dorsal quarter of the circumference of the person's wrist, wherein a ventral portion of the smart watch and/or wrist band is configured to be worn on at least part of the ventral quarter of the circumference of the person's wrist, wherein a first lateral portion of the smart watch and/or wrist band is configured to be worn on a first lateral quarter of the circumference of the person's wrist between the dorsal quarter and the ventral quarter, wherein a second lateral portion of the smart watch and/or wrist band is configured to be worn on a second lateral quarter of the circumference of the person's wrist between the dorsal quarter and the ventral quarter, wherein the second lateral quarter is opposite the first lateral quarter;
   the first light-emitting display on the wearable smart watch and/or wrist band, wherein the portion of the smart watch and/or wrist band on which the greatest percentage of the first light-emitting display is located is the dorsal portion; and
   the second light-emitting display on the wearable smart watch and/or wrist band, wherein the second light-emitting display has a first configuration in which the portion of the smart watch and/or wrist band on which the greatest percentage of the second light-emitting display is located is the first lateral portion or the second lateral portion and the second light-emitting display is a first size, wherein the second light-emitting display has a second configuration in which the portion of the smart watch and/or wrist band on which the greatest percentage of the second light-emitting display is located is the dorsal portion and the second light-emitting display is a second size, wherein the second size is greater than the first size, and wherein the second light-emitting display further comprises a plurality of flexibly-connected segments.

2. A wearable device with first and second light-emitting displays comprising:
   a smart watch and/or wrist band which is configured to be worn around at least three-quarters of the circumference of a person's wrist and/or lower arm, wherein a dorsal portion of the smart watch and/or wrist band is configured to be worn on a dorsal quarter of the circumference of the person's wrist, wherein a ventral portion of the smart watch and/or wrist band is configured to be worn on at least part of the ventral quarter of the circumference of the person's wrist, wherein a first lateral portion of the smart watch and/or wrist band is configured to be worn on a first lateral quarter of the circumference of the person's wrist between the dorsal quarter and the ventral quarter, wherein a second lateral portion of the smart watch and/or wrist band is configured to be worn on a second lateral quarter of the circumference of the person's wrist between the dorsal quarter and the ventral quarter, wherein the second lateral quarter is opposite the first lateral quarter;
   the first light-emitting display on the wearable smart watch and/or wrist band, wherein the portion of the smart watch and/or wrist band on which the greatest percentage of the first light-emitting display is located is the dorsal portion; and
   the second light-emitting display on the wearable smart watch and/or wrist band, wherein the second light-emitting display has a first configuration in which the portion of the smart watch and/or wrist band on which the greatest percentage of the second light-emitting display is located is the first lateral portion or the second lateral portion and the second light-emitting display is a first size, wherein the second light-emitting display has a second configuration in which the portion of the smart watch and/or wrist band on which the greatest percentage of the second light-emitting display is located is the dorsal portion and the second light-emitting display is a second size, wherein the second size is greater than the first size, and wherein the second light-emitting display is made with an electroactive polymer.

* * * * *